(12) United States Patent
Friend et al.

(10) Patent No.: US 10,744,488 B2
(45) Date of Patent: Aug. 18, 2020

(54) OZONE-ACTIVATED NANOPOROUS GOLD AND METHODS OF ITS USE

(71) Applicants: President and Fellows of Harvard College, Cambridge, MA (US); Lawrence Livermore National Security, LLC, Livermore, CA (US)

(72) Inventors: Cynthia M. Friend, Belmont, MA (US); Robert J. Madix, Belmont, MA (US); Branko Zugic, Somerville, MA (US); Lucun Wang, Malden, MA (US); Michelle L. Personick, Cambridge, MA (US); Juergen Biener, San Leandro, CA (US); Monika Margarete Biener, San Leandro, CA (US)

(73) Assignees: President and Fellows of Harvard College, Cambridge, MA (US); Lawrence Livermore National Security, LLC, Livermore, CA (US)

( * ) Notice: Subject to any disclaimer, the term of this patent is extended or adjusted under 35 U.S.C. 154(b) by 0 days.

(21) Appl. No.: 16/070,943

(22) PCT Filed: Jan. 20, 2017

(86) PCT No.: PCT/US2017/014407
§ 371 (c)(1),
(2) Date: Jul. 18, 2018

(87) PCT Pub. No.: WO2017/127728
PCT Pub. Date: Jul. 27, 2017

(65) Prior Publication Data
US 2019/0022627 A1    Jan. 24, 2019

Related U.S. Application Data

(60) Provisional application No. 62/280,997, filed on Jan. 20, 2016.

(51) Int. Cl.
*B01J 23/52*    (2006.01)
*C07C 67/39*    (2006.01)
(Continued)

(52) U.S. Cl.
CPC .......... *B01J 23/52* (2013.01); *B01J 35/0013* (2013.01); *B01J 35/023* (2013.01); *B01J 35/026* (2013.01);
(Continued)

(58) Field of Classification Search
CPC .. B01J 23/48; B01J 23/50; B01J 23/52; C22C 5/02
(Continued)

(56) References Cited

U.S. PATENT DOCUMENTS 8,937,197 B2    1/2015  Friend et al.
2003/0212283 A1*  11/2003  Parker ............... B01J 23/50
                                              549/534
(Continued)

OTHER PUBLICATIONS

Rohe ("CO oxidation on nanoporous gold: A combined TPD and XPS study of active catalysts" Surface Science, 609, 2013, p. 106-112) (Year: 2013).*

(Continued)

*Primary Examiner* — Patricia L. Hailey
(74) *Attorney, Agent, or Firm* — Clark & Elbing LLP

(57) ABSTRACT

The invention relates to nanoporous gold nanoparticle catalysts formed by exposure of nanoporous gold to ozone at elevated temperatures, as well as methods for production of esters and other compounds.

8 Claims, 49 Drawing Sheets

(51) Int. Cl.
| | |
|---|---|
| B01J 35/00 | (2006.01) |
| B01J 35/02 | (2006.01) |
| B01J 35/10 | (2006.01) |
| C07C 67/40 | (2006.01) |
| C07C 45/29 | (2006.01) |
| B01J 37/16 | (2006.01) |
| B01J 37/02 | (2006.01) |
| B01J 37/00 | (2006.01) |
| B01J 37/06 | (2006.01) |
| B01J 37/14 | (2006.01) |

(52) U.S. Cl.
CPC ........... *B01J 35/10* (2013.01); *B01J 35/1009* (2013.01); *B01J 35/1061* (2013.01); *B01J 35/1066* (2013.01); *B01J 37/0018* (2013.01); *B01J 37/0215* (2013.01); *B01J 37/06* (2013.01); *B01J 37/14* (2013.01); *B01J 37/16* (2013.01); *C07C 45/29* (2013.01); *C07C 67/39* (2013.01); *C07C 67/40* (2013.01); *B01J 35/002* (2013.01)

(58) Field of Classification Search
USPC .......................................... 502/344; 420/511
See application file for complete search history.

(56) References Cited

U.S. PATENT DOCUMENTS

| | | | |
|---|---|---|---|
| 2007/0134144 A1* | 6/2007 | Fajardie ............... | A24B 15/288 423/210 |
| 2009/0101241 A1 | 4/2009 | Biener et al. | |

OTHER PUBLICATIONS

Daisuke Yamashita et al., "In situ measurements of change in work function of Pt, Pd and Au surfaces during desorption of oxygen using photoemission yield spectrometer in air." Applied Surface Science 343, pp. 240-244. (Year: 2016).*
Baker et al., "The mystery of gold's chemical activity: local bonding, morphology and reactivity of atomic oxygen," Phys Chem Chem Phys. 13(1):34-46 (2011).
Biener et al., "Effect of surface chemistry on the stability of gold nanostructures," Langmuir. 26(17):13736-40 (2010).
Boronin et al., "XPS and UPS study of oxygen states on silver," J Electron Spectrosc Relat Phenom. 96(1-3):43-51 (1998).
Bowker et al., "Oxygen adsorption on Ag powder," J Chem Soc Faraday Trans. 85(8):2635-40 (1989).
Bowker et al., "Oxygen induced adsorption and reaction of $H_2$, $H_2O$, CO and $CO_2$ on single crystal Ag(110)," Surf Sci. 92(2-3):528-48 (1980).
Bull et al., "Absolute electron impact ionization cross-sections and polarisability volumes for $C_2$ to $C_4$ aldehydes, $C_4$ and $C_6$ symmetric ethers and $C_3$ to $C_6$ ketones," Int J Mass Spectrom. 273(1-2):53-7 (2008).
Campbell et al., "The effect of size-dependent nanoparticle energetics on catalyst sintering," Science. 298(5594):811-4 (2002).
Campbell, "Atomic and molecular oxygen adsorption on Ag (111)," Surf Sci. 157(1):43-60 (1985).
Chen et al., "Geometrically controlled nanoporous PdAu bimetallic catalysts with tunable Pd/Au ratio for direct ethanol fuel cells," ACS Catal. 3(6):1220-30 (2013).
Dean et al., "Adsorption studies on catalysts under UHV/HV conditions: I. Oxygen adsorption on alumina supported silver," Appl Surf Sci. 35(1):27-40 (1988).
Deng et al., "A pathway for NH addition to styrene promoted by gold," Angew Chem Int Ed. 45(42):7075-8 (2006).
Deng et al., "Selective oxidation of styrene on an oxygen-covered Au(111)," J Am Chem Soc. 127(49):17178-9 (2005).
Deng et al., "Selectivity switch for nitrogen functionalization of styrene on Au (1 1 1)," Surf Sci. 602(5):1066-71 (2008).
Ding et al., "Nanoporous gold leaf: 'Ancient technology'/advanced material," Adv Mater. 16(21):1897-1900 (2004).
Déronzier et al., "Catalysis on nanoporous gold-silver systems: Synergistic effects toward oxidation reactions and influence of the surface composition," J Catal. 311:221-9 (2014).
Déronzier et al., "Pure nanoporous gold powder: synthesis and catalytic properties," Chem Mater. 23(24):5287-9 (2011).
Erlebacher et al., "Evolution of nanoporosity in dealloying," Nature. 410(6827):450-3 (2001).
Fujita et al., "Atomic observation of catalysis-induced nanopore coarsening of nanoporous gold," Nano Lett. 14(3):1172-7 (2014).
Gottfried et al., "Oxygen chemisorption on Au(110)-(1×2) I. Thermal desorption measurements," Surf Sci. 525(1-3):184-96 (2003).
Hammond et al., "X-ray photoelectron spectroscopic studies of cadmium- and silver-oxygen surfaces," Anal Chem. 47(13):2193-9 (1975).
Haruta et al., "Novel gold catalysts for the oxidation of carbon monoxide at a temperature far below 0° C.," Chem Lett. 16(2):405-8 (1987).
Hemminger, "From quanta to the continuum: opportunities for mesoscale science," (2012) (84 pages).
Hoflund et al., "Surface characterization study of Ag, AgO, and $Ag_2O$ using x-ray photoelectron spectroscopy and electron energy-loss spectroscopy," Phys Rev B. 62(16):11126-33 (2000).
Hudson et al., "Absolute electron impact ionization cross-sections and polarizability volumes for the $C_2$ to $C_6$ methanoates and $C_3$ to $C_7$ ethanoates," Int J Mass Spectrom. 248(1-2):42-6 (2006).
Hudson et al., "Absolute electron impact ionization cross-sections for CO, $CO_2$, OCS and $CS_2$," J Phys B: At Mol Opt Phys. 37(2):445-55 (2003).
International Search Report and Written Opinion for International Application No. PCT/US17/14407, dated Apr. 10, 2017 (18 pages).
Jaffey et al., "Reactivity of sulfur-containing molecules on noble metal surfaces. 2. tert-Butyl Thioalcohol on Au(110)." J Am Chem Soc. 116(7):3012-9 (1994).
Jaffey et al., "Reactivity of sulfur-containing molecules on noble metal surfaces. 4. Benzenethiol on Au (110)," J Am Chem Soc. 116(7):3020-7 (1994).
Jaffey et al., "The reactivity of sulfur-containing molecules on noble metal surfaces: III. Ethanethiol on Au(110) and Ag(110)," Surf Sci. 311(1-2):159-71 (1994).
Jones et al., "Gold(III) oxide," Acta Crystallogr B. 35(6):1435-7 (1979).
Karakalos et al., "Catalytic production of methyl acrylates by gold-mediated cross coupling of unsaturated aldehydes with methanol," Surf Sci. (2016) (9 pages).
Kibis et al., "The investigation of oxidized silver nanoparticles prepared by thermal evaporation and radio-frequency sputtering of metallic silver under oxygen," Appl Surf Sci. 257(2):404-13 (2010).
Kim et al., "Oxygen adsorption and oxidation reactions on Au(2 1 1) surfaces: exposures using $O_2$ at high pressures and ozone ($O_3$) in UHV," Surf Sci. 600(19):4622-32 (2006).
Kolmakov et al., "Imaging gold clusters on $TiO_2$(110) at elevated pressures and temperatures," Catal Lett. 70(3-4):93-7 (2000).
Kosuda et al., "Oxygen-mediated coupling of alcohols over nanoporous gold catalysts at ambient pressures," Angew Chem Int Ed. 51(7):1698-1701 (2012).
Krozer et al., "X-ray photoemission spectroscopy study of UV/ozone oxidation of Au under ultrahigh vacuum conditions," J Vac Sci Technol A. 15(3):1704-9 (1997).
Lang et al., "Novel nanoporous Au-Pd alloy with high catalytic activity and excellent electrochemical stability," J Phys Chem C. 114(6):2600-3 (2010).
Lee et al., "Developing monolithic nanoporous gold with hierarchical bicontinuity using colloidal bijels," J Phys Chem Lett. 5(5):809-12 (2014).
Lee et al., "Synthesis of hollow and nanoporous gold/platinum alloy nanoparticles and their electrocatalytic activity for formic acid oxidation," J Colloid Interface Sci. 388(1):74-9 (2012).
Legare et al., "Interaction of oxygen with Au surfaces: A LEED, AES and ELS study," Surf Sci. 91(1):175-86 (1980).

(56) References Cited

OTHER PUBLICATIONS

Liu et al., "Effect of molecular structure on epoxidation of allylic olefins by atomic oxygen on Au," Dalton Trans. 39(36):8521-6 (2010).
Liu et al., "Selective oxidation of cyclohexanol and 2-cyclohexen-1-ol on O/Au (111): The effect of molecular structure," Langmuir. 26(21):16552-7 (2010).
Liu et al., "Surface-mediated self-coupling of ethanol on gold," J Am Chem Soc. 131(16):5757-9 (2009).
Ma et al., "Interfacial nanodroplets guided construction of hierarchical Au, Au—Pt, and Au—Pd particles as excellent catalysts," Sci Rep. 4:4849 (2014) (7 pages).
Marsden et al., "Aerobic oxidation of aldehydes under ambient conditions using supported gold nanoparticle catalysts," Green Chem. 10(2):168-70 (2008).
Min et al., "Tuning reactivity and selectivity for olefin oxidation through local O bonding on Au," ChemCatChem. 1(1):116-21 (2009).
Moskaleva et al., "Silver residues as a possible key to a remarkable oxidative catalytic activity of nanoporous gold," Phys Chem Chem Phys. 13(10):4529-39 (2011).
Nyce et al., "Synthesis and characterization of hierarchical porous gold materials," Chem Mater. 19(3):344-6 (2007).
Outka et al., "Acid-base and nucleophilic chemistry of atomic oxygen on the Au(110) surface: reactions with formic acid and formaldehyde," Surf Sci. 179(2-3):361-76 (1987).
Outka et al., "Broensted basicity of atomic oxygen on the gold(110) surface: reactions with methanol, acetylene, water, and ethylene," J Am Chem Soc. 109(6):1708-14 (1987).
Pan et al., "Low-temperature chemoselective gold-surface-mediated hydrogenation of acetone and propionaldehyde," ChemCatChem. 4(9):1241-4 (2012).
Pan et al., "Low-temperature hydrogenation of acetaldehyde to ethanol on H-precovered Au (111)," J Phys Chem Lett. 2(12):1363-7 (2011).
Personick et al., "Catalyst design for enhanced sustainability through fundamental surface chemistry," Philos Trans a Math Phys Eng Sci. 374(2061) (2016) (18 pages).
Personick et al., "Making sense of the mayhem behind shape control in the synthesis of gold nanoparticles," J Am Chem Soc. 135(49):18238-47 (2013).
Personick et al., "Ozone-activated nanoporous gold: a stable and storable material for catalytic oxidation," ACS Catal. 5(7):4237-41 (2015) (Supporting information included) (11 pages).
Personick et al., "Tailored mesoscale gold alloy materials for energy- and resource-efficient catalysis," presentation at American Chemical Society Spring Meeting, Mar. 25, 2015.
Qian et al., "Ultrafine nanoporous gold by low-temperature dealloying and kinetics of nanopore formation," Appl Phys Lett. 91(8):083105-1-3 (2007) (3 pages).
Rodriguez-Reyes et al., "Origin of the selectivity in the gold-mediated oxidation of benzyl alcohol," Surf Sci. 606(15-16):1129-34 (2012).
Rodriguez-Reyes et al., "van der Waals interactions determine selectivity in catalysis by metallic gold," J Am Chem Soc. 136(38):13333-40 (2014).
Sault et al., "Adsorption of oxygen and hydrogen on Au(110)-(1×2)," Surf Sci. 169(2-3):347-56 (1986).
Stowers, "From model studies on Au (1 1 1) to working conditions with unsupported nanoporous gold catalysts: Oxygen-assisted coupling reactions," J Catal. 308:131-41 (2013).
Suzuki et al., "Aerobic oxidative esterification of aldehydes with alcohols by gold-nickel oxide nanoparticle catalysts with a core-shell structure," ACS Catal. 3(8):1845-9 (2013).
Sykes et al., "Nucleation, growth, sintering, mobility, and adsorption properties of small gold particles on polycrystalline titania," J Phys Chem B. 106(21):5390-4 (2002).
Tanuma et al., "Calculations of electron inelastic mean free paths. V. Data for 14 organic compounds over the 50-2000 eV range," Surf Interface Anal. 21(3):165-76 (1994).
Tyson et al., "Charge redistribution in Au—Ag alloys from a local perspective," Phys Rev B. 45(16):8924-8 (1992).
Wang et al., "Active site densities, oxygen activation and adsorbed reactive oxygen in alcohol activation on npAu catalysts," Faraday Discuss. 188:57-67 (2016).
Wang et al., "Active sites for methanol partial oxidation on nanoporous gold catalysts," J Catal. 344:778-83 (2016).
Wang et al., "Catalytic activity of nanostructured Au: Scale effects versus bimetallic/bifunctional effects in low-temperature CO oxidation on nanoporous Au," Beilstein J Nanotechnol. 4:111-28 (2013) (19 pages).
Wang et al., "Exploiting basic principles to control the selectivity of the vapor phase catalytic oxidative cross-coupling of primary alcohols over nanoporous gold catalysts," J Catal. 329:78-86 (2015).
Wang et al., "Facile Fabrication of Porous Pd—Au Bimetallic Nanostructures for Electrocatalysis," Electroanalysis. 24(4):911-6 (2012).
Wang et al., "Pd—Pb/SDB bimetallic catalysts for the direct oxidative esterification of methacrolein to methyl methacrylate," Ind Eng Chem Res. 51(46):15004-10 (2012).
Wittstock et al., "Nanoporous Au: an unsupported pure gold catalyst?," J Phys Chem C. 113(14):5593-600 (2009).
Wittstock et al., "Nanoporous gold catalysts for selective gas-phase oxidative coupling of methanol at low temperature," Science. 327(5963):319-22 (2010).
Wittstock et al., "Nanoporous gold: a new gold catalyst with tunable properties," Farad Discuss. 152:87-98 (2011).
Wittstock et al., "Nanoporous gold: a new material for catalytic and sensor applications," Phys Chem Chem Phys. 12(40):12919-30 (2010).
Xia et al., "Shape-controlled synthesis of metal nanocrystals: simple chemistry meets complex physics?," Angew Chem Int Ed. 48(1):60-103 (2009).
Xu et al., "A paradigm for predicting selective oxidation on noble metals: oxidative catalytic coupling of amines and aldehydes on metallic gold," Faraday Discuss. 152:241-52 (2011).
Xu et al., "Achieving optimum selectivity in oxygen assisted alcohol cross-coupling on gold," J Am Chem Soc. 132(46):16571-80 (2010).
Xu et al., "Activated metallic gold as an agent for direct methoxycarbonylation," J Am Chem Soc. 133(50):20378-83 (2011).
Xu et al., "Ag/Au mixed sites promote oxidative coupling of methanol on the alloy surface," Chem Eur J. 20(16):4646-52 (2014).
Xu et al., "Alkyl groups as synthetic vehicles in gold-mediated oxidative coupling reactions," Phys Chem Chem Phys. 15(9):3179-85 (2013).
Xu et al., "Dual-function of alcohols in gold-mediated selective coupling of amines and alcohols," Chem Eur J. 18(8):2313-8 (2012).
Xu et al., "Low temperature CO oxidation over unsupported nanoporous gold," J Am Chem Soc. 129(1):42-3 (2007).
Xu et al., "Oxygen-assisted cross-coupling of methanol with alkyl alcohols on metallic gold," Chem Sci. 1(3):310-4 (2010).
Xu et al., "Selectivity control in gold-mediated esterification of methanol," Angew Chem Int Ed. 48(23):4206-9 (2009).
Xu et al., "Vapour-phase gold-surface-mediated coupling of aldehydes with methanol," Nat Chem. 2(1):61-65 (2010).
Zhang et al., "Mesoscale spherical and planar organizations of gold nanoparticles," Functional Materials Letters 1(1):43-53 (2008).
Zielasek et al., "Gold catalysts: nanoporous gold foams," Angew Chem Int Ed. 45(48):8241-4 (2006).
Zugic et al., "Continuous catalytic production of methyl acrylates from unsaturated alcohols by gold: the strong effect of C=C unsaturation on reaction selectivity," ACS Catal. 6(3):1833-9 (2016).
Zugic et al. "Dynamic restructuring drives catalytic activity on nanoporous gold-silver alloy catalysts," Nat Mater. 16(5):558-64 (2017) (8 pages).

* cited by examiner

12K gold foil

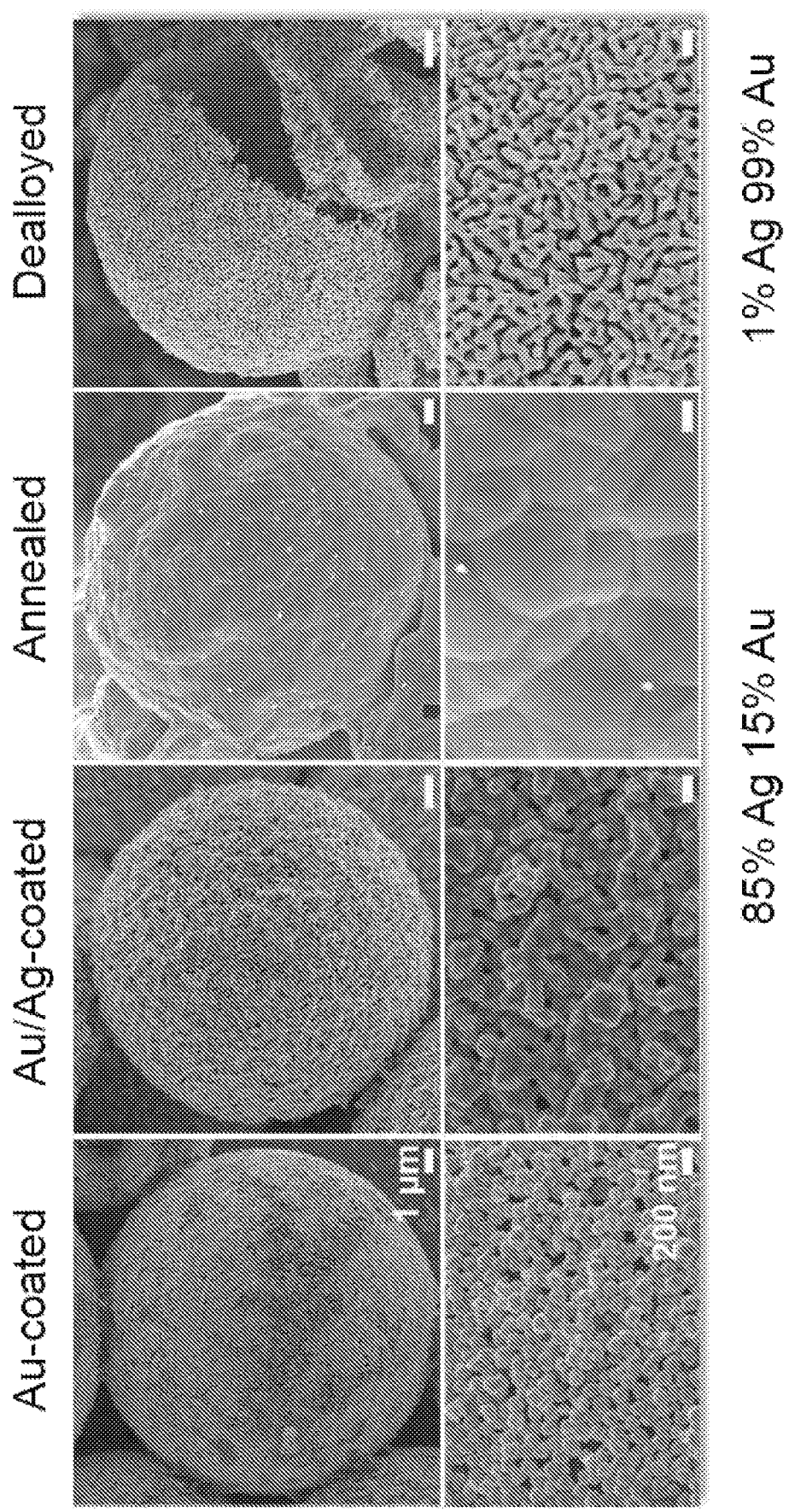

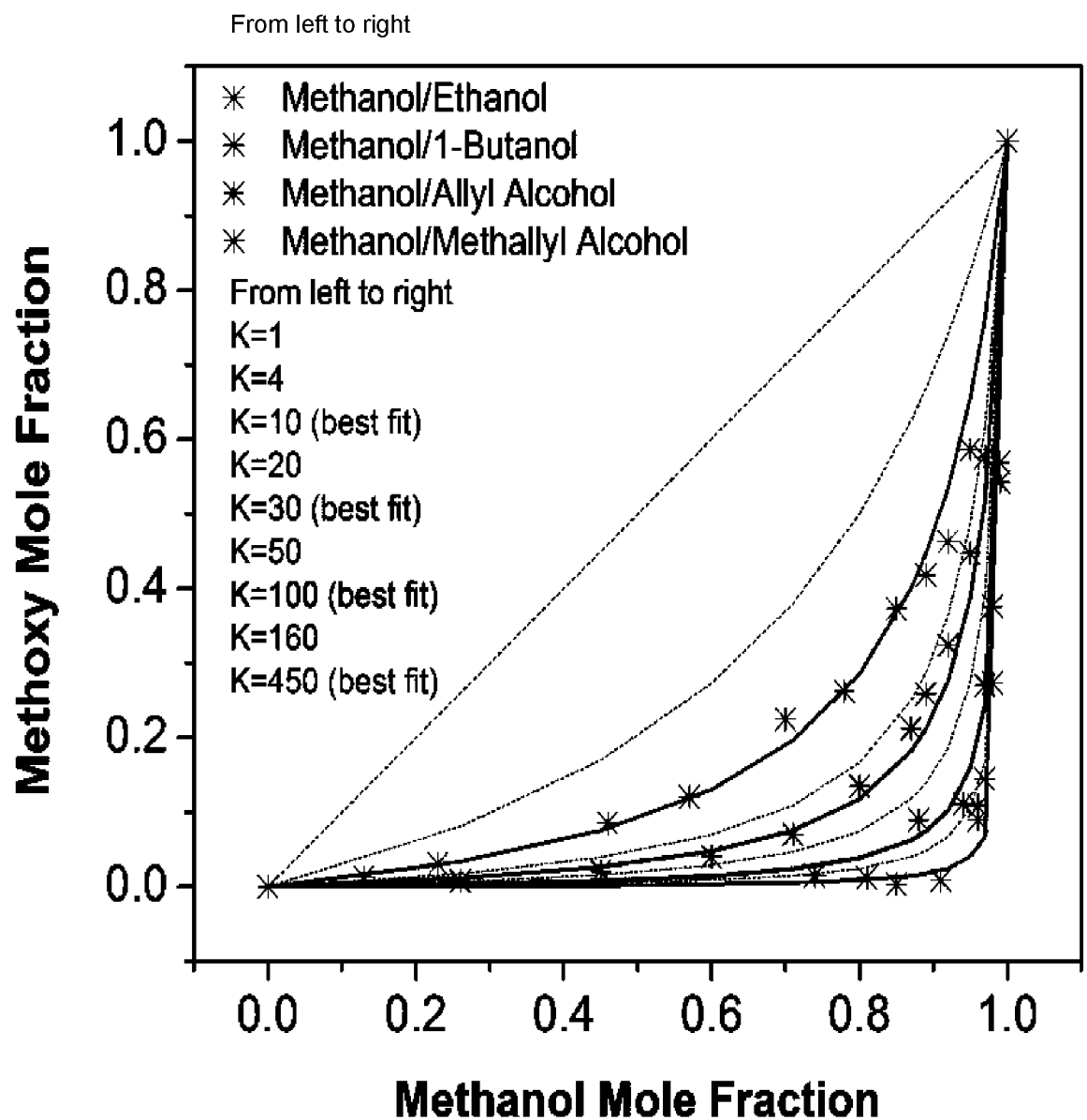

FIG. 20A
FIG. 20B
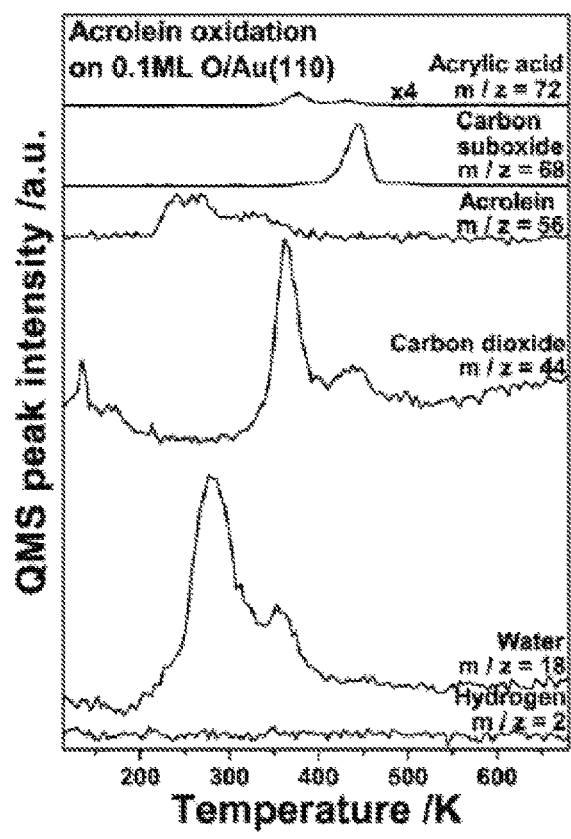
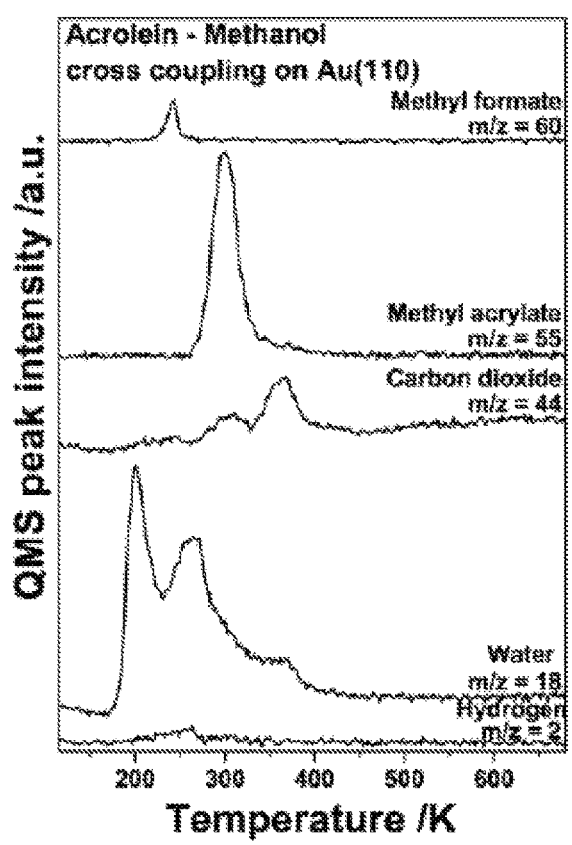

FIG. 20C
FIG. 20D
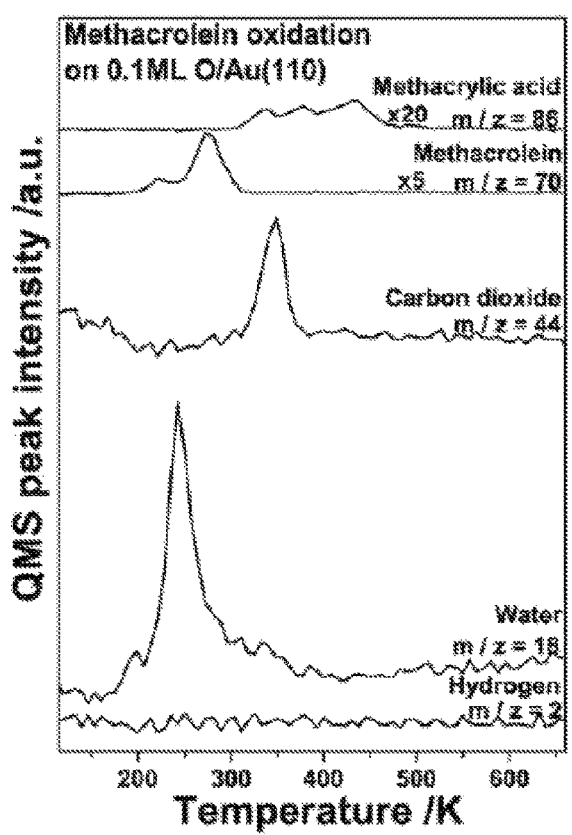
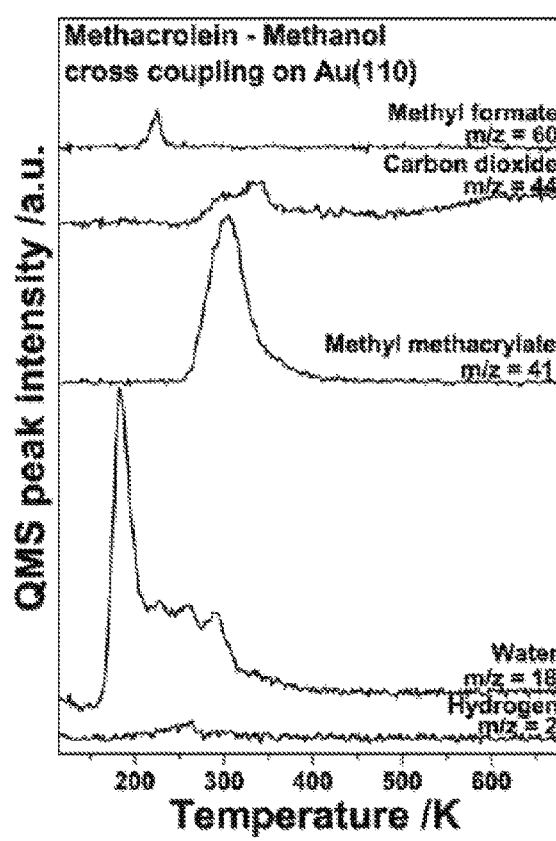

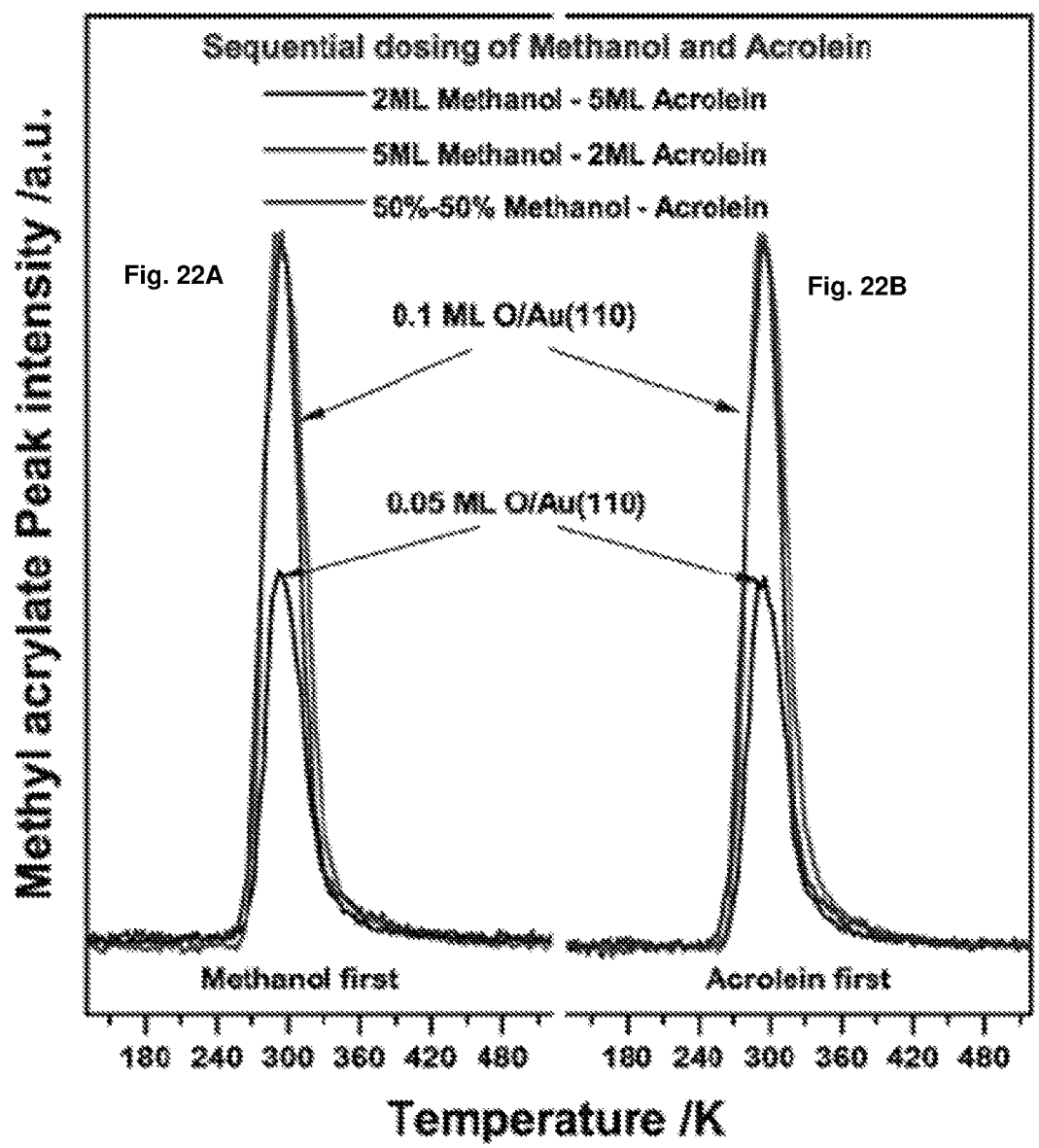

OZONE-ACTIVATED NANOPOROUS GOLD AND METHODS OF ITS USE

STATEMENT REGARDING FEDERALLY SPONSORED RESEARCH

This invention was made with government support under grant number DE-SC0012573 from the U.S. Department of Energy. The government has certain rights to the invention.

BACKGROUND OF THE INVENTION

There is widespread interest in developing new catalytic materials for large-scale chemical transformations, such as selective oxidation processes, in order to meet the global challenge of reducing energy use. The overall objective is to design materials that continuously function as catalysts at moderate operating temperature and that have high reaction selectivity for desired products. A major objective in catalysis science is to create materials that can be reproducibly prepared and that have catalytic activity and selectivity sustained over time. Although considerable advances have been made in the synthesis of exotic nanomaterials with tailored shapes, sizes and compositions, (Xia, Y. et al. *Angew. Chem. Int. Ed.* 2009, 48, 60; Personick, M. L. et al. *J. Am. Chem. Soc.* 2013, 135, 18238) there is an ongoing need to determine how to reproducibly control their catalytic behavior and enhance their longevity. Materials that blend metal compositions and bridge multiple length scales open up a wealth of opportunities to design more energy-efficient catalysts that also maximize the economical use of resources such as precious metals (Hemminger, J. et al. From Quanta to the Continuum: Opportunities for Mesoscale Science. http://science.energy.gov/bes/news-and-resources/reports). However, new materials raise fresh challenges, especially in activating these materials for catalytic process and maintaining their activity and selectivity (Hemminger, J. et al. From Quanta to the Continuum: Opportunities for Mesoscale Science. http://science.energy.gov/bes/news-and-resources/reports).

Nanoscale gold supported on metal oxides has been widely investigated as a catalyst material for selective oxidation because the relative inertness of the gold can render high selectivity (Wittstock, A. et al. *Science* 2010, 327, 319; Baker, T. A. et al. *Phys. Chem. Chem. Phys.* 2011, 13, 34; Wittstock, A. et al. *Phys. Chem. Chem. Phys.* 2010, 12, 12919; Haruta, M. et al. *Chem. Lett.* 1987, 16, 405). One important factor impeding the use of supported nanoscale gold catalysts is their propensity to agglomerate and to rapidly lose activity (Kolmakov, A. et al. *Catal. Lett.* 2000, 70, 93; Sykes, E. C. H. et al. *J. Phys. Chem. B* 2002, 106, 5390; Campbell, C. T. et al. *Science* 2002, 298, 811). Recently, nanoporous metal materials have been prepared using a wide variety of methods, including dealloying of bulk alloys as well as bottom-up synthetic approaches (Ding, Y. et al. *Adv. Mater.* 2004, 16, 1897; Erlebacher, J. et al. *Nature* 2001, 410, 450; Chen, L. Y. et al. *ACS Catal.* 2013, 3, 1220; Ma, A. et al. *Sci. Rep.* 2014, 4, 4849; Lee, M. N. et al. *J. Phys. Chem. Lett.* 2014, 5, 809; Déronzier, T. et al. *J. Catal.* 2014, 311, 221; Déronzier, T. et al. *Chem. Mater.* 2011, 23, 5287; Xu, C. et al. *J. Am. Chem. Soc.* 2007, 129, 42; Zielasek, V. et al. *Angew. Chem. Int. Ed.* 2006, 45, 8241; Lang, X. Y. et al. *J. Phys. Chem. C* 2010, 114, 2600; Wang, H. et al. *Electroanalysis* 2012, 24, 911; Lee, D. et al. *J. Colloid Interface Sci.* 2012, 388, 74). In particular, free-standing nanoporous Au etched from bulk Ag—Au alloys via a method that results in a dilute Ag—Au alloy (~1-3% Ag) has been investigated as a catalyst for oxidative processes, including the selective partial oxidation of alcohols (Wittstock, A. et al. *Science* 2010, 327, 319; Wittstock, A. et al. *Phys. Chem. Chem. Phys.* 2010, 12, 12919; Xu, C. et al. *J. Am. Chem. Soc.* 2007, 129, 42; Zielasek, V. et al. *Angew. Chem. Int. Ed.* 2006, 45, 8241). Nanoporous gold sustains activity over a relatively extended period, (Xu, C. et al. *J. Am. Chem. Soc.* 2007, 129, 42; Zielasek, V. et al. *Angew. Chem. Int. Ed.* 2006, 45, 8241) most likely due to the nanoporous morphology which does not readily agglomerate at moderate temperatures. The 1-3% Ag that remains in the material after this particular etching procedure is key to the activity of nanoporous gold for oxidative catalysis. The residual Ag dissociates molecular oxygen ($O_2$) to form adsorbed O, and the amount of Ag regulates the oxidative strength of the material (Wittstock, A. et al. *Science* 2010, 327, 319; Déronzier, T. et al. *Chem. Mater.* 2011, 23, 5287; Zielasek, V. et al. *Angew. Chem. Int. Ed.* 2006, 45, 8241; Moskaleva, L. V. et al. *Phys. Chem. Chem. Phys.* 2011, 13, 4529; Wittstock, A. et al. *J. Phys. Chem. C* 2009, 113, 5593). Challenges that have hindered the use of these nanoporous materials for catalysis include (1) activating them readily and (2) sustaining their activity. Current methods for activating nanoporous gold materials for catalytic partial oxidation involve flowing a mixture of reactant gases, such as CO and $O_2$, over the catalyst at approximately 75° C. until the material becomes active for CO oxidation. This activation procedure is highly inconsistent and irreproducible (Stowers, K. J. et al. *J. Catal.* 2013, 308, 131); for example, some ingots of nanoporous gold activate easily, while others do not activate at all, even if kept under a steady flow of reactants for many days. In addition, nanoporous gold materials which have been activated for methanol self-coupling using this method deactivate for that same reaction after exposure to higher alcohols, such as ethanol and 1-butanol. It is of key importance to develop a reliable procedure for reproducibly activating nanoporous gold materials (Wittstock, A. at al. *Science* 2010, 327, 319). Accordingly, there is a need for new methods of activating gold catalysts.

SUMMARY OF THE INVENTION

The invention provides gold catalysts and method of their use in the synthesis of esters and other compounds.

In a first aspect, the invention provides a method of synthesizing a nanoporous gold catalyst. The method includes the steps of providing nanoporous gold comprising 0.1 to 10% silver by atom; and contacting the nanoporous gold with ozone at a temperature of at least 100° C., e.g., about 150° C., to form the activated nanoporous gold catalyst. For instance, the nanoporous gold may be contacted with the ozone at a temperature of at least 100° C., 105° C., 110° C., 115° C., 120° C., 125° C., 130° C., 135° C., 140° C., 145° C., 150° C., 155° C., 160° C., 165° C., 170° C., 175° C., 180° C., 185° C., 190° C., 195° C., or 200° C.

In some embodiments, the nanoporous gold is formed by diminishing the quantity of silver present within an alloy containing gold and silver. In some embodiments, the alloy contains from 70 to 85% silver by atom. In some embodiments, the quantity of silver is diminished, e.g., by mixing the alloy with a solution containing nitric acid. In some embodiments, the nanoporous gold catalyst contains from 1 to 3% silver by atom, such as about 1% silver by atom.

In some embodiments, the contacting is performed by flowing the ozone over the nanoporous gold, e.g., at a rate of 10-100 mL/min, such as about 50 mL/min. The ozone may be present within a mixture containing one or more other gases. In some embodiments, the ozone has a concentration of from 10 to 50 g/Nm$^3$ within the mixture. In some embodiments, the one or more gases are $O_2$ and/or He, e.g., in a ratio of from 10:1 to 1:10 by volume, such as about 1:1 by volume.

In some embodiments, the nanoporous gold has a pore size of 1-250 nm, e.g., 30-75 nm. In other embodiments, the nanoporous gold has a ligament dimension of 10-500 nm. In some embodiments, the nanoporous gold is a foil. The foil may have a thickness of from 50 to 150 nm, such as 100 nm. In some embodiments, the foil has a pore depth of from 25 to 75 nm, such as 50 nm. The foil may have a ligament width of from 15 to 45 nm, such as about 30 nm. In some embodiments, the nanoporous gold is an ingot. The ingot may have a thickness of from 100 to 500 μm (e.g., from 200 to 300 μm, such as about 200, 205, 210, 215, 220, 225, 230, 235, 240, 245, 250, 255, 260, 265, 270, 275, 280, 285, 290, or 300 μm). In some embodiments, the ingot has a ligament width of 10 to 100 nm, e.g., about 50 nm. In some embodiments, the ingot has a surface area of from 1 to 6 m$^2$/g. In some embodiments, the nanoporous gold is a shell. The shell may have a diameter of from 1 to 100 μm, e.g., 4 to 12 μm. The shell may have a thickness of from 50 to 500 nm (e.g., from 250 to 500 nm or 350 to 450 nm, such as about 350, 355, 360, 365, 370, 375, 380, 385, 390, 395, 400, 405, 410, 415, 420, 425, 430, 435, 440, 445, or 450 nm). In some embodiments, the shell has a pore depth of from 100 to 300 nm, such as about 200 nm. The shell may be characterized by a ligament width of from 35 to 115 nm, such as about 75 nm. In some embodiments, the shell has a surface area of from 0.1 to 10 m$^2$/g, e.g., 4 to 10 m$^2$/g.

The invention also provides a method of producing a nanoporous gold catalyst shell by mixing gold or silver nanoparticles with one or more core particles (styrene-divinylbenzene copolymer, $SiO_2$, or $TiO_2$); reducing a source of gold or silver ions (e.g., a gold or silver salt) onto the particles formed with a reducing agent optionally in the presence of a stabilizing agent, wherein the source is gold when gold nanoparticles are employed and silver when silver nanoparticles are employed; reducing a source of gold or silver ions (e.g., a gold or silver salt) onto the particles with a reducing agent optionally in the presence of a stabilizing agent, wherein gold is employed when silver nanoparticles are employed and silver is employed when gold nanoparticles are employed; alloying the silver and gold in the particles; and diminishing the silver content (e.g., by reaction with acid or base) to produce the nanoporous gold catalyst shell. In one embodiment, the core particle is removed during the alloying. In certain embodiments, the method includes mixing one or more gold or silver nanoparticles with one or more core particles; adding a source of gold ions to the particles formed; adding a source of silver ions to the particles formed; and diminishing the silver content in the particles. In some embodiments, the shell is produced by a process including the steps of mixing a gold nanoparticle with one or more particles containing a styrene-divinylbenzene copolymer; adding polyvinylpyrrolidone, hydroxylamine hydrochloride, and gold (III) chloride trihydrate to the particles; adding polyvinylpyrrolidone, silver nitrate, and ascorbic acid to the particles; and diminishing the silver content e.g., by contacting the particles with nitric acid.

Shells may be produced by evaporating gold and silver metal onto a core particle, alloying the gold and silver, and diminishing the silver content.

In another aspect, the invention provides a nanoporous gold catalyst produced by any of the methods of the invention.

In an additional aspect, the invention provides a nanoporous gold catalyst containing from 0.1 to 10% silver by atom and treated with ozone at a temperature of at least 100° C., e.g., at about 150° C. The nanoporous gold catalyst may have a ligament size of 1-500 nm, e.g., 10-100 nm. The nanoporous gold catalyst may be further treated with a mixture of oxygen and an alcohol, e.g., a primary C1-10 alcohol, or aldehyde, a C2-10 aldehyde, at a temperature of at least 100° C., e.g., at about 150° C. The nanoporous gold catalyst treated with an alcohol and oxygen may have a ligament size of 100-500 nm.

The invention further provides a nanoporous gold catalyst including 0.1 to 10% silver by atom, wherein the catalyst is active for selective oxidation of alcohols and inactive for oxidation of CO. In other aspects, the invention provides a nanoporous gold catalyst including 0.1 to 10% silver by atom, wherein the surface layer of the catalyst has a higher Ag/Au atomic ratio relative to the bulk material. In other aspects, the invention provides a nanoporous gold catalyst including 0.1 to 10% silver by atom, wherein comprises an oxygen species with a binding energy of 531.5 eV. The invention further provides a nanoporous gold catalyst comprising 0.1 to 10% silver by atom wherein at least 80% of the surface silver is oxidized and at least 60% of the surface gold is oxidized.

In another aspect, the invention features a method of synthesizing an ester or aldehyde by reacting an alcohol on a nanoporous gold catalyst comprising from 0.1 to 10% silver by atom and treated with ozone at a temperature of at least 100° C. under conditions to synthesize the ester or aldehyde. In certain embodiments, the alcohol is reacted with an aldehyde to produce the ester, e.g., wherein the aldehyde is a C1-C10 alkyl aldehyde or a C2-C10 alkenyl aldehyde (such as propenal or 2-methylprop-2-enal). In other embodiments, the alcohol is reacted with a second alcohol to produce the ester. The alcohol and second alcohol may be the same (for self-coupling) or different (for cross coupling). The alcohol may be a primary C1-10 alkyl alcohol or a primary C2-C10 alkenyl alcohol, such as methanol, ethanol, 1-butanol, 3-propenol, or 2-methylprop-2-en-1-ol. In certain embodiments, the alcohol is methanol, and the second alcohol is ethanol, 1-butanol, 3-propenol, or 2-methylprop-2-en-1-ol. Exemplary esters include methyl formate, ethyl acetate, methyl propionate, methyl butyrate, n-propyl propionate, n-butyl butyrate, methyl acrylate, and methyl methacrylate. In other embodiments, the alcohol is oxidized to the aldehyde.

In some embodiments, the alcohol is present within a gaseous mixture that contains $O_2$. The gaseous mixture may additionally contain He, e.g., at a ratio of from 10:1 to 1:10 $O_2$::He by volume, such as about 1:5 $O_2$:He by volume. In some embodiments, the gaseous mixture contains the alcohol at a concentration of from 1 to 25% by volume, such as 10% by volume. In some embodiments, the reacting is performed at a temperature of from 100 to 200° C. (e.g., about 100° C., 105° C., 110° C., 115° C., 120° C., 125° C., 130° C., 135° C., 140° C., 145° C., 150° C., 155° C., 160° C., 165° C., 170° C., 175° C., 180° C., 185° C., 190° C., 195° C., or 200° C.). In some embodiments, the reacting is performed at a temperature of about 150° C. In some embodiments, the method includes flowing the gaseous mixture including the alcohol over the nanoporous gold catalyst, e.g., at a rate of from 10 to 100 mL/min, such as about 50 mL/min.

In another aspect, the invention provides a method of oxidizing reactants by contacting at least one reactant with a nanoporous gold catalyst of the invention under conditions for the reactant to be oxidized to produce a product. In certain embodiments, this method specifically excludes the formation of esters from primary alcohols or primary alcohols and esters. In other embodiments, the at least one reactant and product are as shown in the following table:

| Product | Reactant(s) |
|---|---|
| Amide | Amine and aldehyde |
| Amide | Amine and alcohol |
| Epoxide | Alkene |
| Ether | Halide and optional alcohol |
| Aziridine | Amine and alkene |
| Nitrile | Amine and alkene |
| Carbonate | Alcohol and CO |
| Aldehyde | Primary Alcohol |
| Ketone | Secondary Alcohol or alkene |
| Carboxylic Acid | Alkene or aldehyde |
| Carbon suboxide | Aldehyde |
| Alkene | Thiol or ketone |
| Sulfide | Thiol |
| Ester | Alcohol |
| Ester | Alcohol and aldehyde |
| Carbon dioxide | Carboxylic acid, alkyne, or aldehyde. |

By "alkyl" is meant a saturated hydrocarbyl moiety. An alkane is an alkyl group substituted with a hydrogen to satisfy valency.

By "alkenyl" is meant an unsaturated hydrocarbyl moiety having at least one carbon-carbon double bond but no carbon-carbon triple bond. An alkene is an alkenyl group substituted with a hydrogen to satisfy valency.

By "alkyne" is a hydrocarbyl compound having at least one carbon-carbon triple bond.

By "alcohol" is meant a compound of formula R—OH. R is a saturated or unsaturated hydrocarbyl group. For example, R is a C1-C10 alkyl group or a C2-C10 alkenyl group. By "aldehyde" is meant a compound of formula R—C(O)H. R is a hydrogen saturated or unsaturated hydrocarbyl group. For example, R is a C1-C9 alkyl group or a C2-C9 alkenyl group.

By "amide" is meant a compound of formula R—C(O)N(R')(R"). Each of R, R', and R" is independently hydrogen or a saturated or unsaturated hydrocarbyl group.

By "amine" is meant a compound of formula N(R)(R')(R"). Each of R, R', and R" is independently hydrogen or a saturated or unsaturated hydrocarbyl group.

By "aryl" is meant an aromatic hydrocarbyl moiety.

By "aziridine" is meant a compound of formula

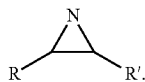

R and R' are independently hydrogen or a saturated or unsaturated hydrocarbyl group.

By "carbonate" is meant a compound of formula ROC(O)OR'. R and R' are independently a saturated or unsaturated hydrocarbyl group.

By "carboxylic acid" is meant a compound of the formula RC(O)OH. R is a hydrogen or saturated or unsaturated hydrocarbyl group.

By "ether" is meant a compound of formula R—O—R'. R and R' are independently a saturated or unsaturated hydrocarbyl group.

By "epoxide" is meant a compound of formula

R and R' are hydrogen or a saturated or unsaturated hydrocarbyl group.

By "ester" is meant a compound of formula R—C(O)—O—R'. R and R' are independently a saturated or unsaturated hydrocarbyl group. For example, R is a C1-C9 alkyl group or a C2-C9 alkenyl group, and R' is a C1-C10 alkyl group or a C2-C10 alkenyl group.

By "halide" is meant a compound of formula RX. R is a saturated or unsaturated hydrocarbyl group, and X is a halogen, e.g., F, Cl, Br, or I.

By "hydrocarbyl" is meant a radial derived from a hydrocarbon. Hydrocarbyl moieties may be further substituted as is known in the art and as described herein, e.g., by halogen.

By "ketone" is meant a compound of formula RC(O)R'. R and R' are independently a saturated or unsaturated hydrocarbyl group.

By "nitrile" is meant a compound of formula R≡CN. R is a saturated or unsaturated hydrocarbyl group.

By "sulfide" is meant a compound of formula RSR'. R and R' are independently a saturated or unsaturated hydrocarbyl group.

By "thiol" is meant a compound of formula RSH. R is a saturated or unsaturated hydrocarbyl group.

BRIEF DESCRIPTION OF THE DRAWINGS

FIG. 12 shows a series of electron micrographs tracing the synthesis of hollow nanoporous gold shells.

FIG. 19 shows the fraction of adsorbed methoxy species as a function of gas phase methanol mole fraction for the cross-coupling reactions of methanol with ethanol, 1-butanol, allyl alcohol and methallyl alcohol over npAu in a flow reactor. The dashed lines indicate the expected surface methoxy fraction for various equilibrium constants (which govern the displacement reaction of surface species and determine relative surface coverages).

FIGS. 20a-20d shows the TPR spectra of acrolein and methacrolein oxidation and cross-coupling with methanol on O/Au(110) interface. 0.1 ML of atomic oxygen was dosed at 300 K via ozone exposure, subsequently the organics were dosed at 130 K. (a) Excess acrolein (~1 ML) was dosed independently, (b) 0.3 ML acrolein and 0.7 ML methanol, (c) excess methacrolein (~1 ML) was dosed independently, (d) 0.3 ML methacrolein and 0.7 ML methanol; (Methanol was dosed prior to acrolein and methacrolein in b and d). Overlapping mass fragments have been subtracted for clarity. The heating rate was 5 K s$^{-1}$.

FIGS. 22a-22c shows the TPR spectra for the sequential dosing of multilayers of methanol and acrolein on the O/Au(110) interfaces for three cases: a) 2 ML methanol first and then 5 mL of acrolein at 120 K, b) 2 ML of acrolein first and then 5 mL of methanol at 120 K, c) 0.5 ML of methanol first and then 0.5 ML of acrolein at 120 K. The relative amounts of methyl acrylate production for the three cases are also shown, indicating that the final coupling product is proportional to methoxy formation on the surface.

DETAILED DESCRIPTION

Figures 1A, 1B, 1C:
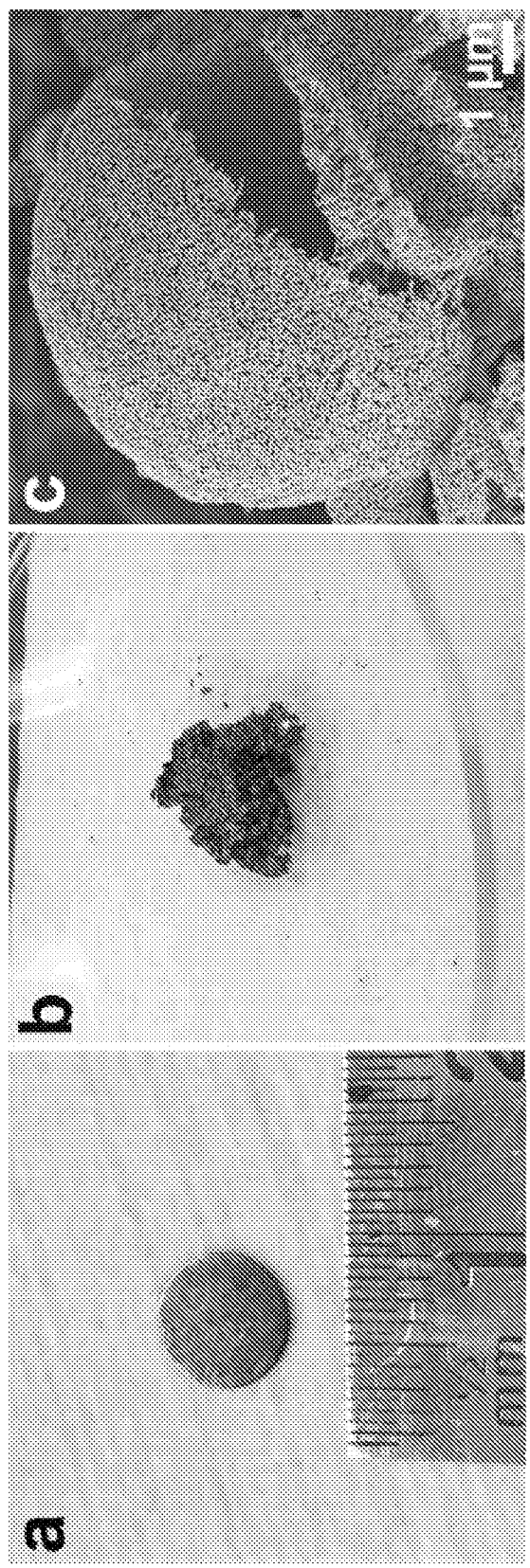
FIG. 1a-1f show photographs (a,b) and scanning electron microscopy (SEM) images (c-f) of freshly prepared nanoporous Au materials described herein: ingots (a,d), foils (b,e), and hollow shells (c,f). Images (d-f) are higher magnification SEM images of the materials in (a-c). All scale bars in (d-f) are the same size.

The invention provides ozone-activated nanoporous gold materials, which are a fundamentally different catalytic material, methods of their fabrication, and methods of their use. Recent efforts have focused on the removal of adventitious carbon from nanoporous gold ingots in order to effect alcohol self-coupling reactions under ultrahigh vacuum (UHV) conditions (Stowers, K. J. et al. *J. Catal.* 2013, 308, 131). It has been shown that cycles of ozone doses to the nanoporous gold surface followed by heating to approximately 600 K burn off carbon and yield ingots active for the dissociation of $O_2$ (Stowers, K. J. et al. *J. Catal.* 2013, 308, 131). However, the high annealing temperature used in these experiments results in coarsening of the nanoporous gold ingots and some accumulation of Ag at the surface. In contrast, the procedures described herein activate not only nanoporous gold ingots, but also hollow nanoporous gold shells and thin nanoporous gold foils, even though the latter materials are particularly challenging to activate as a consequence of their method of preparation.

There are several differences between ozone-activated nanoporous gold catalysts of the invention and materials activated by simply flowing reactant mixtures over the nanoporous gold at lower temperature without ozone treatment. First, the ozone-activated nanoporous gold operates at 150° C. and above, whereas nanoporous gold activated by reactant, such as dioxygen, is catalytically active at lower temperatures, such as 20° C. (Wittstock, A. et al. *Science* 2010, 327, 319). Additionally, ozone-activated nanoporous gold materials of the invention generally do not catalyze CO oxidation under standard operation conditions, as no $CO_2$ production has been observed by GC-MS using these materials. In contrast, previously reported reactant-activated catalysts readily oxidize CO (Xu, C. et al. *J. Am. Chem. Soc.* 2007, 129, 42; Zielasek, V. et al. *Angew. Chem. Int. Ed.* 2006, 45, 8241; Wittstock, A. et al. *Farad. Discuss.* 2011, 152, 87; Fujita, T. et al. *Nano Lett.* 2014, 14, 1172). This difference may represent an advantage the use of for ozone-activated materials, as these substances may selectively catalyze oxidation of primary alcohols in the presence of CO. Furthermore, previous experiments with nanoporous gold ingots activated solely by the flowing reactant stream have reported the exclusive formation of butyraldehyde from the oxidation of 1-butanol, with no evidence of the self-coupling product, butyl butyrate (Kosuda, K. M. et al. *Angew. Chem. Int. Ed.* 2012, 51, 1698). In contrast, ozone-activated nanoporous gold materials of the invention are capable of catalyzing the oxidative self-coupling of 1-butanol.

These observations indicate that nanoporous gold catalysts generated using the ozone activation treatment described herein are fundamentally different from those generated by activation in the flowing reactant stream despite having the same general bulk composition and structure.

The invention is based in part on the discovery that exposure of nanoporous gold ingots, foils, and shells to ozone reproducibly activates the material for the catalytic partial oxidation of primary alcohols. This procedure is effective even though the initial state of these nanoporous materials is significantly different due to the methods by which they are prepared. The method is simple and reproducible. All three materials have been shown to maintain stable catalytic activity over a period of time of at least one week and catalyze the formation of both esters and aldehydes from ethanol and 1-butanol, which confirms the Au-like surface reactivity of these catalysts.

The nanoporous gold catalysts of the invention may be used in the synthesis of esters and aldehydes from alcohols or mixtures of an alcohol and aldehyde. The methods may employ self-coupling, e.g., to form methyl formate from methanol, or cross coupling, e.g., to form methyl esters of higher alcohols from methanol and a higher alcohol or from methanol and aldehydes. In particular, acrylates and methacrylates are important building blocks for the industrial production of textiles and plastics. They are produced primarily by acid-catalyzed homogeneous reactions, resulting in high energy usage for separation and waste remediation. In an effort to eliminate the need for separation of the catalyst from the reaction stream, there has been a recent focus on the development of heterogeneous catalysts for the direct oxidative coupling of unsaturated alcohols and/or aldehydes to form esters (Wang, B. et al. *Ind. Eng. Chem. Res.* 2012, 51, 15004; Suzuki, K. et al. *ACS Catal.* 2013, 3, 1845). The nanoporous gold catalysts of the invention can be used in the synthesis of unsaturated esters, and this process provides an alternative, green route for the production of acrylates and methacrylates.

Ozone-Activated Nanoporous Gold Catalysts

Described herein are methods for the facile and reproducible activation of nanoporous gold materials for the catalytic and selective partial oxidation of alcohols under ambient pressure and steady flow conditions. These methods can be used to produce active nanoporous gold catalysts, e.g., by flowing ozone or an ozone/dioxygen mixture over the catalyst at elevated temperatures, such as 150° C., followed by a flowing stream of reactance, e.g., 10% methanol and 20% oxygen. A temperature gradient may be used for this process, such as a temperature ramp from 50-150° C. as the gases are flowed over the catalyst surface. The methods of the invention can be used to reproducibly activate nanoporous gold catalysts capable of promoting the selective oxidation of primary alcohols over prolonged periods of time. The nanoporous gold materials activated in this manner exhibit catalytic behavior distinct from those activated under different conditions previously reported. Once activated in this manner, these nanoporous gold materials can be stored and reactivated by flow of reactant gases at elevated temperatures, such as 100 to 200° C. (e.g., 150° C.) for one or more hours. Catalysts formed according to the methods of the invention possess improved selectivity for the coupling of higher alcohols, such as 1-butanol, and are not active for carbon monoxide oxidation.

The catalytic properties of ozone-activated nanoporous gold are manifest in the structural features of the catalyst.

The nanoporous gold materials activated in this fashion may have a variety of forms, such as a foil, ingot, or shell.

Ingots of the ozone-activated nanoporous gold catalysts described herein can be prepared via chemical etching of $Ag_{70}Au_{30}$ bimetallic alloy disks in concentrated nitric acid (FIG. 1) (Wittstock, A. et al. Science 2010, 327, 319; Ding, Y. et al. Adv. Mater. 2004, 16, 1897; Erlebacher, J. et al. Nature 2001, 410, 450). Such ingots may have a diameter, e.g., of approximately 5 mm and a thickness of 200-300 μm. Nanoporous gold ingots of the invention may be characterized by a ligament width, e.g., 10-500 nm. Ingots may additionally have a surface area of from 2 to 6 $m^2/g$, such as 4.6 $m^2/g$.

Figures 1D, 1E, 1F:
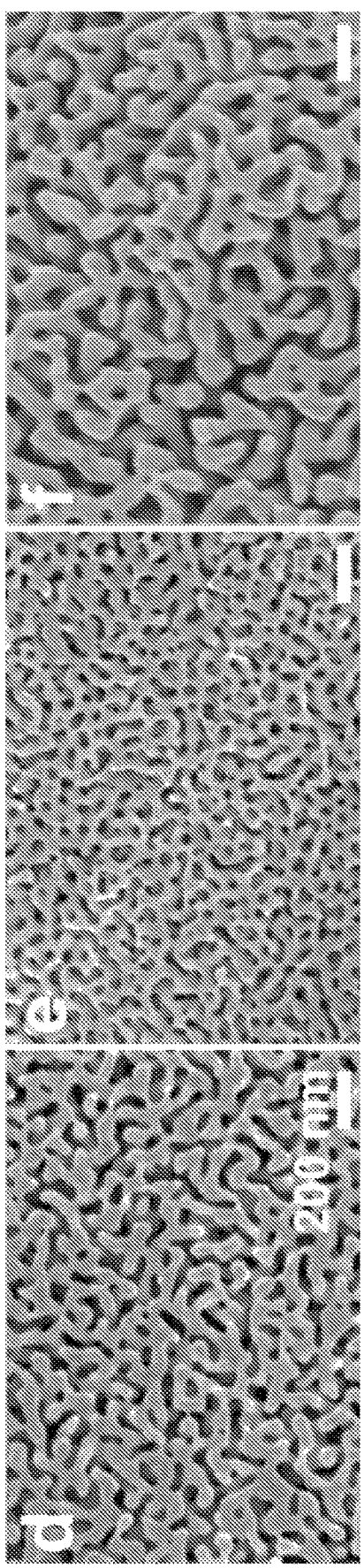
Figure 5:
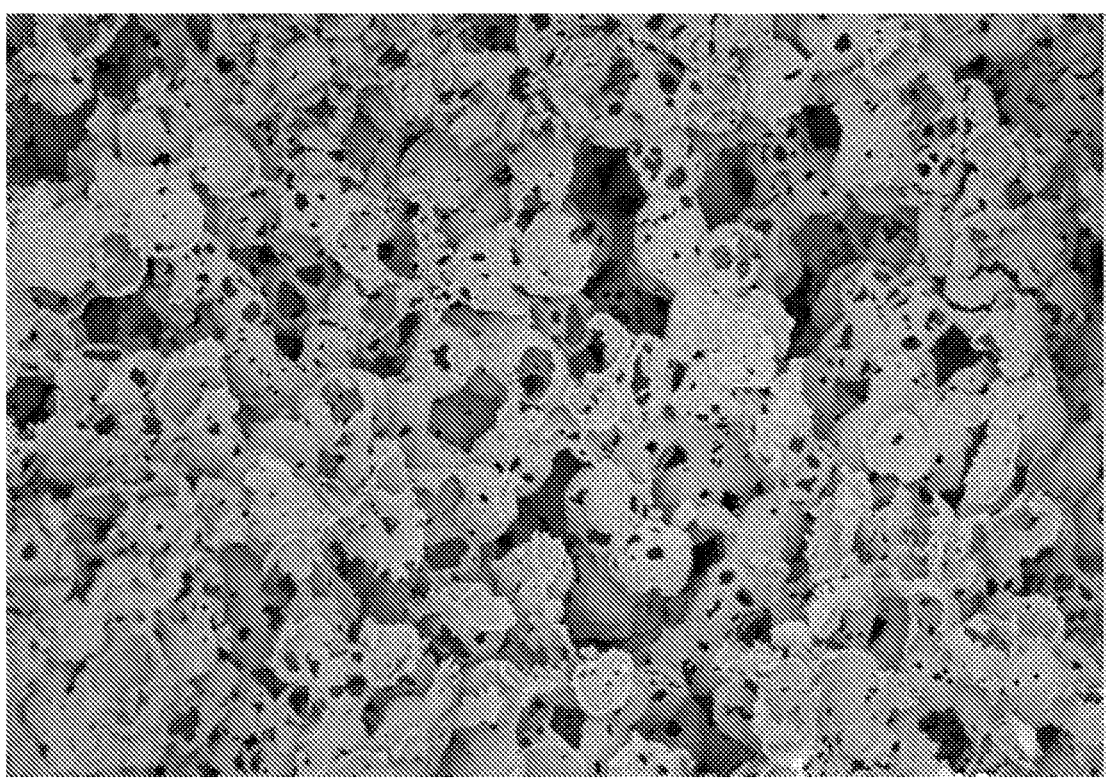
FIG. 5 shows large area SEM image of hollow nanoporous gold shells.
Figure 6B:
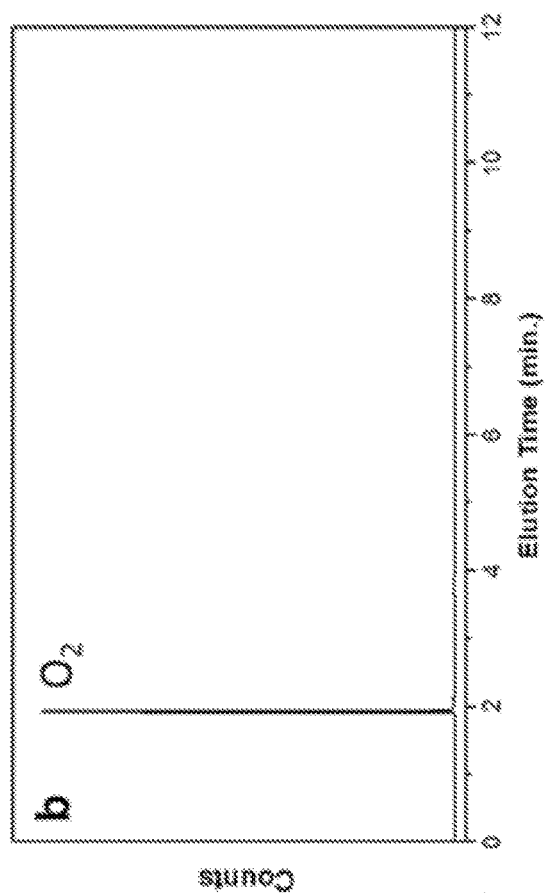
FIGS. 6a-6e show representative GC-MS data for methanol oxidation on ozone-activated nanoporous gold. (a) GC chromatogram showing peaks for (1) water, (2) methanol, and (3) methyl formate. MS spectra for each of the peaks are shown below the chromatogram. (b) TCD chromatogram showing a peak for excess $O_2$. (c)-(e) are MS spectra water, methanol, and methyl formate.
Figure 6A:
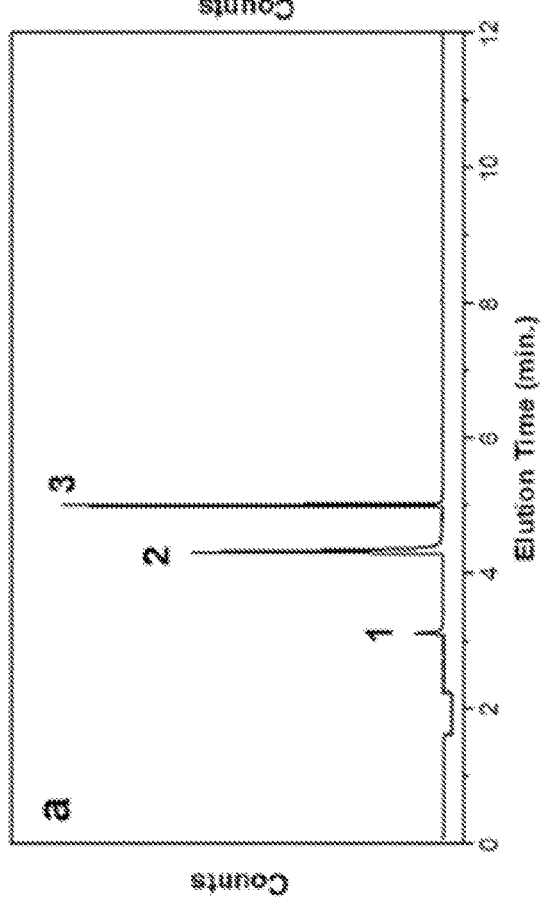
Figure 6E:
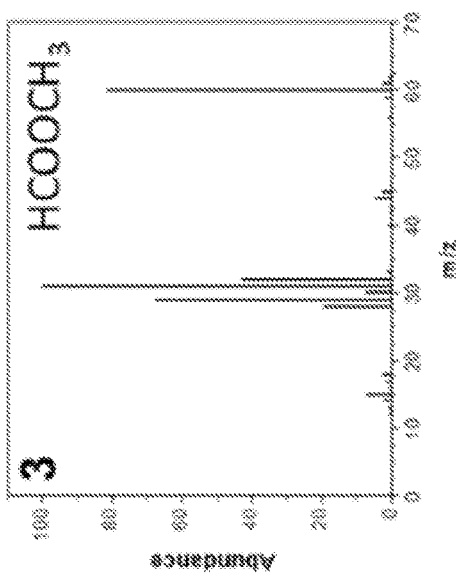
Figure 6D:
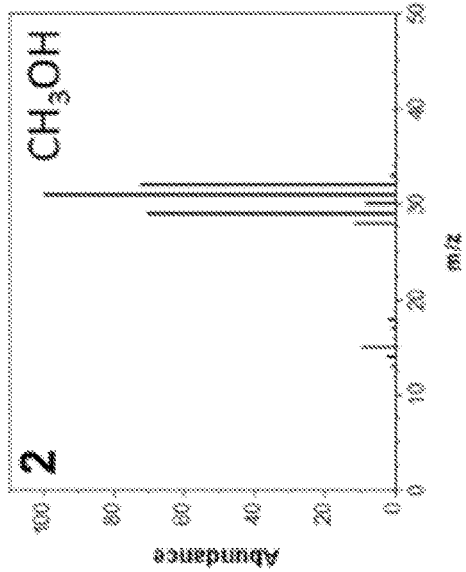
Figure 6C:
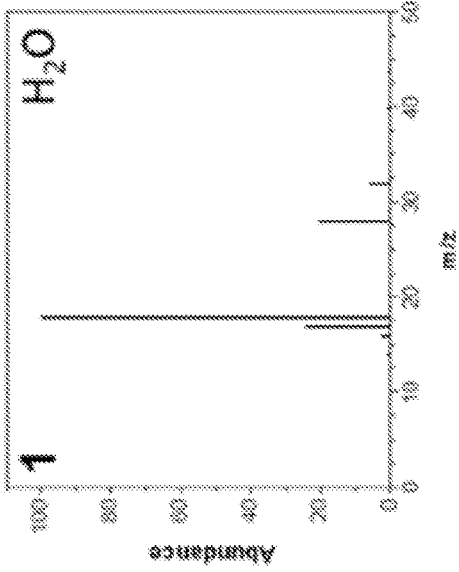

Additionally, the methods of the invention can be used to generate ozone-activated nanoporous gold foils (FIG. 1). Such foils may have a thickness, e.g., of approximately 100 nm. Nanoporous gold foils of the invention can be produced by reducing the silver content of gold/silver alloys, such as 6 karat white gold leaf (Ding, Y. et al. Adv. Mater. 2004, 16, 1897; Erlebacher, J. et al. Nature 2001, 410, 450) ($Ag_{85}Au_{15}$ alloy) and hollow spherical shells of nanoporous Au (FIGS. 1 and 5). For instance, this can be performed by adapting a procedure for synthesizing hierarchically-porous Au monoliths (Nyce, G. W. et al. Chem. Mater. 2007, 19, 344). The foil may have a pore depth of from 25 to 75 nm, such as 50 nm, and may be characterized by a ligament width of from 15 to 45 nm, such as 30 nm.

The methods of the invention can also be used to produce ozone-activated nanoporous gold catalysts in the form of shells. Such shells may have a diameter, e.g., of approximately 8 μm and/or a thickness of from 350 to 450 nm. Generally, the pore and ligament dimensions of the ingots, foils, and shells may be similar, e.g., ranging from 30 to 75 nm, but the pore depths of foils and shells may be approximately 50 nm and 200 nm, respectively, compared to the half thickness of the ingots, which may be 150 μm. Hollow shells of the invention may have a Brunauer-Emmett-Teller (BET) surface area of from 4 to 10 $m^2/g$.

Figure 13:
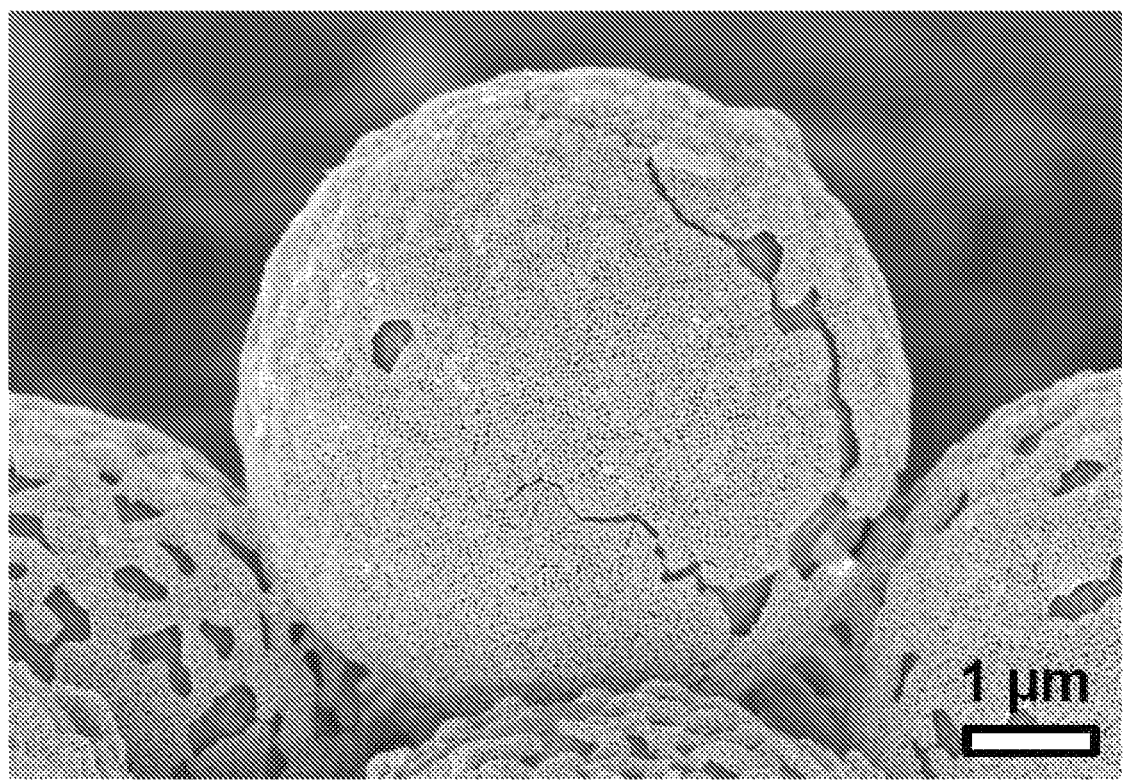
FIG. 13 shows an electron micrograph of a nanoporous gold nanoparticle in the form of a shell as synthesized using the methods described herein with the exception that the core was an amine functionalized silica microsphere and remained intact after fabrication of the shell.

An exemplary procedure useful for the production of such shells includes providing gold nanoparticles, e.g., 5-20 nm in diameter, coating polystyrene microspheres with the gold nanoparticles, depositing gold on the gold-coated polystyrene spheres, depositing silver on the gold coated polystyrene spheres, calcinating the spheres to anneal the silver and gold and remove the polystyrene, and etching in nitric acid to remove silver (FIGS. 12 and 13). For example, methods for the development of gold shells may include coating a particle, such as a styrene-divinylbenzene copolymer, with gold nanoparticles. The resulting particles can then be exposed to polyvinylpyrrolidone, hydroxylamine hydrochloride, and gold (III) chloride, and subsequently mixed with additional polyvinylpyrrolidone, silver nitrate, and ascorbic acid. Removal of the polystyrene core and reduction of silver content by contact with nitric acid produces hollow, nanoporous gold shells of the invention. Alternatively, amine functionalized silica microspheres may be used in place of particles of a styrene-divinylbenzene copolymer, and the core may be retained after the shell is produced (e.g., FIG. 13).

In order to produce nanoporous gold catalysts of the invention, the following exemplary methodology has been developed. First, gold ingots, foils, or shells can be loaded into a vessel, such as a flow reactor tube furnace in a glass reactor tube. The nanoporous gold can be placed between two pieces of deactivated glass wool, and the temperature of the vessel can be gradually increased from 30° C. to 150° C., e.g., using a linear gradient of 10° C./min. The nanoporous gold can then be exposed to a flow of ozone, e.g., at 30 $g/Nm^3$ in a 50% $O_2$/He gas mixture at a total flow rate of 50 mL/min. The nanoporous gold materials can then be held at 150° C. for one hour under the same flow conditions. Subsequently, the vessel can be cooled to 50° C. and then gradually ramped from 50° C. to 150° C. at 10° C./min in flowing stream of 10% methanol and 20% $O_2$. This can be performed, e.g., such that the total flow rate is 50 mL/min in He.

The morphology of nanoporous gold catalysts may change after contact with reactants, i.e., alcohol and dioxygen. In particular, the ligament width of the catalyst may increase after such contact, e.g., from 30-80 nm to 100-500 nm (FIGS. 4a-4b and 11a-11d).

Nanoporous gold catalysts of the invention can be analyzed using microscopy and spectroscopy techniques known in the art. For instance, the nanoporous gold catalysts can be characterized by scanning electron microscopy (SEM) to examine their morphology, and energy-dispersive X-ray spectroscopy (EDS) to determine their elemental composition. BET surface area analysis can be performed.

The nanoporous gold catalyst of the invention preferably is active for selective oxidation of alcohols and inactive for oxidation of CO. As detailed below, ozone treatment of nanoporous gold produces a catalyst in which the surface layer includes a higher Ag/Au atomic ratio relative to the bulk material, and this ratio changes depending on the state of the catalyst. For example, the Ag/Au atomic ratio is at least 2, 3, 4, 5, 6, 7, 8, 9, 10, 15, or 20 times higher than the bulk. The ratio is highest after ozone treatment, is lower after a phase in which alcohols undergo combustion to $CO_2$, and is further lower after alcohols undergo selective oxidation. In specific examples, the ratio is between 0.35 and 0.55 after ozone treatment, between 0.2 and 0.3 in the combustion phase, and between 0.5 and 0.15 after alcohols have undergo selective oxidation. In other embodiments, the catalyst can be described in terms of the surface oxidation. For example, after ozone treatment, at least 80% of silver (e.g., at least 85, 90, 95, or 99%) and at least 60% of gold (at least 65, 70, 75, or 80%) at the surface is oxidized. In other embodiments, the catalyst includes an oxygen species with a binding energy of 531.5 eV, which is capable of selective oxidation of an alcohol.

Oxidative Self-Coupling of Primary Alcohols

Nanoporous gold activated by treatment with ozone at temperatures of 100° C. or greater, e.g., about 150° C. can be used to convert primary alcohols, such as C1-10 alkyl primary alcohols (e.g., methanol, ethanol, and 1-butanol) and primary C2-C10 alkenyl alcohols (e.g., allyl alcohol and methallyl alcohol), into esters by an oxidative self-coupling process. In other embodiments, a C6-C10 aryl C1-C6 alcohol (e.g., benzylalcohol) can be self-coupled to produce an ester. Without being limited by mechanism, it is proposed that exposure of ozone-activated nanoporous gold catalysts of the invention to primary alcohols results in dissociation of hydrogen-oxygen bonds, thus resulting in the generation of alkoxy moieties bound to the catalyst surface and the concomitant expulsion of water. This intermediate state may then give rise to aldehydes at the catalyst surface, which may then be captured by neighboring alkoxy groups by a nucleophilic acyl substitution process in which hydrogen is expelled in water, yielding an ester formed by the self-coupling of the primary alcohol. This substitution process would serve to regenerate the catalyst for the next iteration of oxidation and esterification.

Among the beneficial properties of ozone-activated nanoporous gold catalysts of the invention is the ability to rapidly and selectively catalyze the conversion of methanol to methyl formate. Table 1, below, provides a summary of the rate and selectivity of the conversion of methanol to methyl formate as catalyzed by nanoporous gold in the form of an ingot, foil, or shell in the presence of 10% methanol, 20% $O_2$ in He, 150° C., and using a flow rate of 50 mL/min.

TABLE 1

Oxidative self-coupling of methanol in the presence of ozone-activated nanoporous gold catalysts

| Form of catalyst | Rate of methanol self-coupling | Selectivity |
|---|---|---|
| Ingot | 0.017 mmol s$^{-1}$ g$^{-1}$ | 100% |
| Foil | 0.091 mmol s$^{-1}$ g$^{-1}$ | 100% |
| Shell | 0.083 mmol s$^{-1}$ g$^{-1}$ | 100% |

Another property that distinguishes between ozone-activated nanoporous gold catalysts and gold catalysts activated by dioxygen is the ability of ozone-activated nanoporous gold to catalyze the oxidative self-coupling of primary alcohols of various carbon chain lengths at similar rates. For instance, both ethanol and 1-butanol self-couple at rates comparable to methanol self-coupling in the presence of ozone-activated nanoporous gold ingots of the invention. Table 2, below, provides a comparison of the conversion ratio of ethanol and 1-butanol to ethyl acetate and n-butyl butyrate, respectively, as catalyzed by nanoporous gold in the form of an ingot, foil, or shell in the presence of 5% alcohol, 20% $O_2$ in He, 150° C., and using a flow rate of 50 mL/min.

TABLE 2

Oxidative self-coupling of ethanol and 1-butanol in the presence of ozone-activated nanoporous gold catalysts

| Form of catalyst | Rate (and selectivity) of ethanol self-coupling | Rate (and selectivity) of 1-butanol self-coupling |
|---|---|---|
| Ingot | 0.010 mmol s$^{-1}$ g$^{-1}$ (36.1%) | 0.008 mmol s$^{-1}$ g$^{-1}$ (20.6%) |
| Foil | 0.014 mmol s$^{-1}$ g$^{-1}$ (22.1%) | 0.021 mmol s$^{-1}$ g$^{-1}$ (11.9%) |
| Shell | 0.010 mmol s$^{-1}$ g$^{-1}$ (20.2%) | 0.016 mmol s$^{-1}$ g$^{-1}$ (16.4%) |

Products obtained from the reaction of primary alcohols, such as primary C1-C10 alkyl alcohols and primary C2-C10 alkenyl alcohols, with nanoporous gold catalysts of the invention can be detected using chromatography and mass spectrometry techniques known in the art. For instance, reaction products can be characterized using an inline gas chromatograph mass spectrometer (GC-MS), and can be quantified using integrated GC peak areas with corrections for MS ionization cross-sections (Xu, B. et al. *J. Am. Chem. Soc.* 2010, 132, 16571; Bull, J. N. et al. *J. Mass Spectrom.* 2008, 273, 53; Hudson, J. E. et al. *Int. J. Mass Spectrom.* 2006, 248, 42). Fixed gases, such as $O_2$ and $CO_2$, can be detected using a thermal conductivity (TCD) detector incorporated into the GC-MS system.

Figure 2:
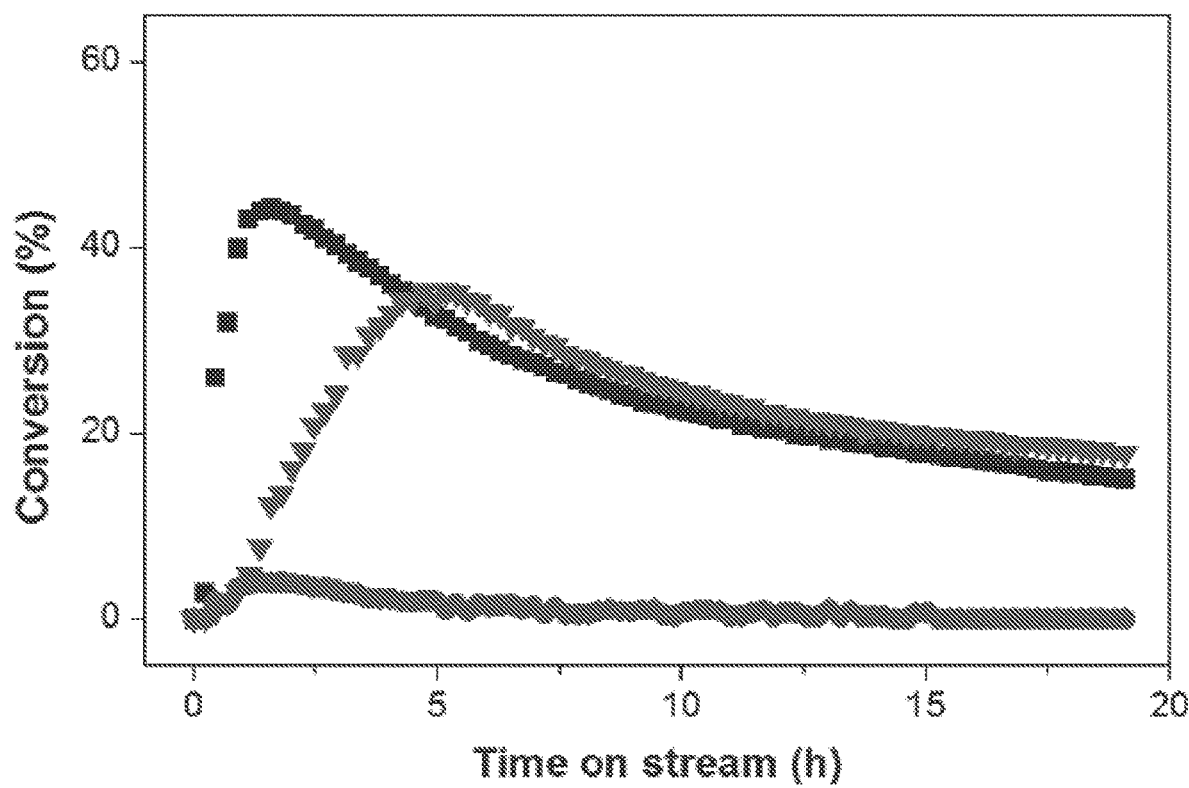
FIG. 2 is a graph showing the conversion of methanol to methyl formate (squares) and to $CO_2$ (circles) versus time for the initial activation and stabilization period of a nanoporous gold shell catalyst in the oxidation of methanol after ozone treatment and conversion to methyl formate (triangles) after exposure to air for four months (previously activated catalyst) (~10 mg of catalyst). A temperature ramp from 50-150° C. takes place between the first and second time points. No carbon dioxide is produced during the reactivation after exposure to air.

The initial activation of nanoporous gold creates a very robust catalyst material that can be removed from the reactor and stored in air for at least four months without losing activity. Once returned to the reactor, a few hours of exposure to the reaction conditions, e.g., used for the methanol reaction (10% methanol and 20% $O_2$ in He, 50 mL/min, 150° C.), were required for the material to return to a stable conversion; no reactivation in ozone was required (FIG. 2). Together, these results demonstrate the utility of this activation method for stably activating a variety of nanoporous gold catalysts, regardless of their architecture or the differences of their preparation method. After stabilization of the catalyst following activation, no loss of catalytic activity was observed for the production of methyl formate from methanol and $O_2$ over an extended period of time even though the surface area of the catalyst decreased due to coarsening of the ligament structures under reaction conditions.

Oxidative Cross-Coupling of Primary Alcohols

Nanoporous gold activated by treatment with ozone at temperatures of 100° C. or greater, e.g., about 150° C. can be used to convert primary alcohols, such as primary C1-10 alkyl alcohols (e.g., methanol, ethanol, and 1-butanol) and primary C2-C10 alkenyl alcohols (e.g., allyl alcohol and methallyl alcohol), into esters by an oxidative cross-coupling process. For instance, nanoporous gold of the invention can be used to catalyze the conversion of, e.g., methanol and allyl alcohol or methanol and methallyl alcohol, to methyl acrylate and methyl methacrylate, respectively.

One factor that influences reaction selectivity in the oxidative coupling of alcohols to esters is competition between different reacting alcohols for reactive sites on the surface. The coverage of adsorbed oxygen determines the number of reactive sites because it is required to initiate the reaction. The relative concentration of alkoxide intermediates formed on the surface is determined by the quasi-equilibrium established between the reactant alcohols. For example, the coupling of methanol and allyl alcohol will depend on the pre-equilibrium between the reactants and the adsorbed alkoxides (Equation 1, shown below). Hence, the relative binding efficacy of the respective alkoxides and the relative concentrations of the reactant alcohols in the reaction mixture determine the relative concentration of the respective alkoxide intermediates and, thus, reaction selectivity.

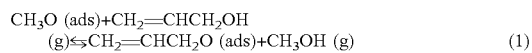

(1)

During the cross-coupling of methanol with ethanol or 1-butanol, for example, nanoporous gold catalyzes the oxygen-assisted production of methyl esters. The product selectivity is governed by, e.g., the relative concentrations of the surface alkoxides and relative rates of aldehyde production from these alkoxides. Due to this phenomenon, moderate to low concentrations of ethanol or 1-butanol (relative to methanol) result in high selectivity to the corresponding acetate or butyrate.

Oxidative Cross-Coupling of Primary Alcohols with Aldehydes

Nanoporous gold activated by treatment with ozone at temperatures of 100° C. or greater, e.g., about 150° C. can be used to catalyze the conversion of primary alcohols, such as primary C1-10 alkyl alcohols (e.g., methanol, ethanol, and 1-butanol) and primary C2-C10 alkenyl alcohols (e.g., allyl alcohol and methallyl alcohol), into esters upon reaction of the alcohol with an aldehyde, such as a C1-C9 alkyl aldehyde (e.g., formaldehyde, acetaldehyde, propanal, and butanal) or a C2-C9 alkenyl aldehyde (e.g., acrolein and methacrolein). In other embodiments, the catalyst is used in the formation of esters upon reaction of an alcohol (e.g., C1-10 alkyl alcohol (e.g., methanol, ethanol, and 1-butanol), C2-C10 alkenyl alcohol (e.g., allyl alcohol and methallyl alcohol), and a C6-C10 aryl C1-C6 alcohol (e.g., benzylalcohol)) with an aldehyde, e.g., a C1-C6 alkyl C6-C10 aryl aldehyde (e.g., benzaldehyde or benzeneacetaldehyde). For instance, ozone-activated nanoporous gold ingots, foils, or shells of the invention can be treated with a primary C1-10 alkyl alcohol or a primary C2-C10 alkenyl alcohol and an aldehyde in order to produce an in ester in which the carbonyl carbon is derived from that of the aldehyde, and the alkoxy moiety is derived from the primary alcohol. In one example, ozone-activated nanoporous gold catalysts of the invention can be treated with methanol and an aldehyde, such as acrolein or methacrolein, in order to produce methyl acrylate or methyl methacrylate, respectively.

Additional Reactions

In addition to self- and cross-coupling reaction of primary alcohols or cross-coupling of primary alcohols with aldehydes, the nanoporous gold catalyst of the invention can be used in oxidation reactions of organic compounds, e.g., as known for Au(111) and Au(110) surfaces. For example, the catalyst can be used, typically in the presence of $O_2$, to catalyze the formation of amides from an amine (e.g., N—C1-C6 alkyl amine or N,N-di-C1-C6 alkylamine, such as dimethylamine) and an aldehyde (e.g., C1-C9 alkyl aldehyde (e.g., formaldehyde, acetaldehyde, propanal, and butanal), a C2-C9 alkenyl aldehyde, or a C1-6 alkyl C6-C10 aryl aldehyde (e.g., benzaldehyde or benzeneacetaldehyde)); amides from an amine (e.g., N—C1-C6 alkyl amine or N,N-di-C1-C6 alkylamine, such as dimethylamine) and an alcohol (e.g., primary C1-10 alkyl alcohols (e.g., methanol, ethanol, and 1-butanol) and primary C2-C10 alkenyl alcohols (e.g., allyl alcohol and methallyl alcohol)), with or without the addition of CO; epoxides from an alkene (e.g., a C2-C10 alkene and a C6-C10 aryl C2-C6 alkene (such as styrene, trans β methyl styrene, a methylstyrene, and allylbenzene)); ethers from halides (e.g., C1-C6 alkyl halide (e.g., methyl iodide or ethyl iodide) or C6-C10 aryl iodide (e.g., phenyl iodide)), optionally in reaction with an alcohol (primary C1-10 alkyl alcohols (e.g., methanol, ethanol, and 1-butanol) and primary C2-C10 alkenyl alcohols (e.g., allyl alcohol and methallyl alcohol)); aziridines or nitriles from an amine (e.g., ammonia, N—C1-C6 alkyl amine, or N,N-di-C1-C6 alkylamine, such as dimethylamine) and an alkene (e.g., C2-10 alkene or C6-C10 aryl C2-C10 alkene (styrene, trans β methyl styrene, α methylstyrene, and allylbenzene)); carbonates from an alcohol (e.g., C1-10 alkyl alcohols (e.g., methanol, ethanol, and 1-butanol), C2-C10 alkenyl alcohols (e.g., allyl alcohol and methallyl alcohol), and C6-C10 aryl alcohols (e.g., phenol)) and CO; aldehydes from an alcohol (e.g., primary C1-10 alkyl alcohols (e.g., methanol, ethanol, and 1-butanol) and primary C2-C10 alkenyl alcohols (e.g., allyl alcohol and methallyl alcohol), and primary C6-C10 aryl C1-C6 alcohol (e.g., benzylalcohol)); ketones from a secondary alcohol (e.g., C3-C10 cycloalkyl alcohol (e.g., cyclohexanol) and C4-C10 cycloalkenyl alcohol (e.g., 2-cyclohexen-1-ol)); carboxylic acids from an alkene (e.g., a C2-C10 alkene and a C6-C10 aryl C2-C6 alkene (such as styrene, trans β methyl styrene, a methylstyrene, and allylbenzene)) or aldehyde (e.g., C1-9 alkyl aldehyde (e.g., formaldehyde, acetaldehyde, propanal, and butanal), a C2-C9 alkenyl aldehyde, or a C1-C6 alkyl C6-C10 aryl aldehyde (e.g., benzaldehyde or benzeneacetaldehyde)); ketones from an alkene (e.g., C2-C10 alkene (e.g., propene), C6-C10 aryl C2-C6 alkene (such as allylbenzene), and C4-C10 cycloalkenyl alcohol (e.g., 2-cyclohexen-1-ol)); carbon suboxide from an aldehyde (e.g., a C2-C9 alkenyl aldehyde (e.g., acrolein)); alkenes from a thiol (e.g., C1-C6 alkyl thiol (e.g., ethanethiol and t-butylthiol)) or ketone (C4-C10 cycloalkenyl ketone (e.g., cyclohexanone)); sulfides from a thiol (e.g., C1-C6 alkyl thiol (e.g., ethanethiol and t-butylthiol) and C6-C10 aryl thiol (e.g., benzenethiol)); esters from halo alcohols (e.g., C1-C10 halo alcohol (e.g., 2,2,2-trifluoroalcohol)); and $CO_2$ from a carboxylic acid (e.g., C1-10 carboxylic acid (e.g., formic acid), alkyne (e.g., C2-C6 alkyne (e.g., acetylene))) or aldehyde (e.g., C1-9 alkyl aldehyde (e.g., formaldehyde, acetaldehyde, propanal, and butanal)). Specific reactions are provides in tables 4 and 5.

TABLE 4

Reactions investigated on single crystal gold surfaces Au(110) under UHV conditions

| Reactant | Major product | Ref |
|---|---|---|
| Allyl alcohol | Acrolein | 1 |
| Methallyl alcohol | Methacrolein | 1 |
| Acrolein | Carbon suboxide | 2 |
| Methacrolein | Acrylic acid | 2 |
| Ethanethiol | Ethylene, Ethane, Diethyl sulfide | 3 |
| tert-Butyl Thioalcohol | Isobutene | 4 |
| Benzenethiol | Biphenyl, Diphenylsulfide, Dibenzothiophene | 5 |
| Formic acid | Carbon dioxide | 6 |
| Formaldehyde | Formic acid, Carbon dioxide | 6 |
| Acetylene | Carbon dioxide | 7 |

1. Zugic, B.; Karakalos, S.; Stowers, K. J.; Biener, M. M.; Biener J.; Friend, C. M.; Madix, R. J. *ACS Catal.* 2016, 6, 1833.
2. Karakalos, S.; Zugic, B.; Stowers, K. J.; Biener, M. M.; Biener, J.; Friend, C. M.; Madix, R. J. *Surface Science* 2016, 652, 58.
3. Jaffey, D. M.; Madix, R. J. *Surface Science* 1994, 311, 159.
4. Jaffey, D. M.; Madix, R. J. *J. Am. Chem. Soc.* 1994, 116, 3012.
5. Jaffey, D. M.; Madix, R. J. *J. Am. Chem. Soc.* 1994, 116, 302.
6. Outka, D. A.; Madix, R. J. *Surface Science* 1987, 179, 361.
7. Outka D. A.; Madix, R. J. *J. Am. Chem. Soc.* 1987, 109, 1708.

TABLE 5

Reactions investigated on single crystal gold surfaces Au(111) under UHV conditions

| Reactant 1 | Reactant 2 | Major product | Ref |
|---|---|---|---|
| Methanol | Formaldehyde | Methyl formate | 2 |
| Methanol | Acetaldehyde | Methyl acetate | 2 |
| Methanol | Benzaldehyde | Methyl benzoate | 2 |
| Methanol | Benzeneacetaldehyde | Methyl phenyl acetate | 2 |
| Dimethylamine | Formaldehyde | Dimethylformamide | 3 |
| Dimethylamine | Acetaldehyde | Dimethylacetamide | 3 |
| Dimethylamine | Propanal | Dimethylpropanamide | 3 |
| Dimethylamine | Butanal | Dimethybutyramide | 3 |
| Dimethylamine | Methanol | Dimethylformamide | 4 |
| Dimethylamine | Ethanol | Dimethylacetamide | 4 |
| Methanol | Ethanol | Methylacetate | 5 |
| Methanol | n-Butanol | Methylbutyrate | 5 |
| n-Butanol | — | Butylbutyrate | 5 |
| Ethanol | Formaldehyde | Ethylformate | 5 |
| Ethanol | — | Ethylactetate | 6 |
| Styrene | | Styrene epoxide | 7 |
| Methyl iodide | — | Dimethyl ether | 8 |
| Ethyl iodide | — | Diethyl ether | 8 |
| Phenyl iodide | — | Diphenyl ether | 8 |
| Ethyl iodide | Ethanol | Diethyl ether | 8 |
| $NH_x$ | Styrene | 2-phenylaziridine | 9 |

TABLE 5-continued

Reactions investigated on single crystal gold surfaces Au(111) under UHV conditions

| Reactant 1 | Reactant 2 | Major product | Ref |
|---|---|---|---|
| Methanol | CO | Dimethylcarbonate | 10, 11 |
| Methanol | Dimethylamine + CO | Me—CO—N(Me)$_2$ | 10, 11 |
| Methanol | Ethanol + CO | Methyl ethyl carbonate | 11 |
| Methanol | Phenol + CO | Methyl phenyl carbonate | 11 |
| 2,2,2-Trifluoroethanol | — | 2,2,2-trifluoroethyl trifluoroacetate | 12 |
| Benzylalcohol | — | Benzylaldehyde benzyl benzoate | 13 |
| Cyclohexanol | — | Cyclohexanone 2-cyclohexen-1-one | 14 |
| Cyclohexanone | — | 2-cyclohexen-1-one | 14 |
| 2-cyclohexen-1-ol | — | Phenol 2-cyclohexene-1,4-dione | 14 |
| 2-cyclohexen-1-one | — | Phenol 2-cyclohexene-1,4-dione | 14 |
| Trans-β-methylstyrene | — | Trans-β-methylstyrene oxide Cinnamic acid Benzoic acid | 15 |
| α-methylstyrene | — | α-phenylacrolein α-phenylacrylic acid | 15 |
| allybenzene | — | Phenylvinyl ketone | 15 |
| Propene | — | Acrylic acid | 16 |
| Acrolein | — | Carbon suboxide | 16 |
| Styrene | — | Benzonitrile Benzyl nitrile Ethylbenzene 2-Phenylaziridine | 17 |

Table 5 References

1. *Angew. Chem. Int. Ed.* 2009, 48, 420.
2. *Nat. Chem.* 2010, 2, 61.
3. *Faraday Discuss.* 2011, 152, 241.
4. *Chem. Eur. J.* 2012, 18, 2313.
5. *Chem. Sci.* 2010, 1, 310.
6. *J. Am. Chem. Soc.* 2009, 131, 5757-5759
7. *J. Am. Chem. Soc.* 2005, 127, 17178-17179
8. *Phys. Chem. Chem. Phys.,* 2013, 15, 3179-3185
9. *Angew. Chem. Int. Ed.* 2006, 45, 7075.
10. U.S. Pat. No. 8,937,197 B2
11. *J. Am. Chem. Soc.* 2011, 133, 20378.
12. *J. Am. Chem. Soc.* 2014, 136, 13333.
13. *Surface Science* 2012, 606, 1129.
14. *Langmuir* 2010, 26, 16552.
15. *Dalton Trans.* 2010, 39, 8521.
16. *ChemCatChem* 2009, 1, 116.
17. *Surface Science* 2008, 602, 1066.

For all reactions described herein, including self coupling and cross coupling reactions, it will be understood that oxygen may be included as a reactant.

EXAMPLES

Example 1. Chemicals and Materials Used for the Production of Ozone-Activated Nanoporous Gold Catalysts Gold (III) chloride trihydrate (HAuCl$_4$·3H$_2$O, 99.9+%), trisodium citrate dihydrate (sodium citrate, 99.9%), polyvinylpyrrolidone (PVP, average MW=40K), hydroxylamine hydrochloride (99%), silver nitrate (AgNO$_3$, 99.9999%), L-ascorbic acid (99+%), methanol (anhydrous, 99.8%), ethanol (99.5+%, absolute), 1-butanol (anhydrous, 99.8%), and nitric acid (69-70%, ACS grade) were purchased from Sigma Aldrich and used as supplied, without further purification. Polystyrene microspheres cross-linked with divinylbenzene (PS/DVB spheres) with a diameter of 11 μm were purchased from Thermo Scientific and used as delivered (10 wt % solution). 6 karat white gold foils were obtained from Giusto Manetti. Deactivated borosilicate glass wool (Restek) was purchased from Fisher Scientific. All glassware was treated with aqua regia (3 HCl:1 HNO$_3$) prior to use. All H$_2$O was purified with a Millipore MILLI-Q® water purification system (resistivity=18.2 MΩ·cm).

Example 2. Synthesis of Nanoporous Gold Foils, Ingots, and Shells

Nanoporous gold foils were prepared by chemical etching of 6 karat white gold foils (85% Ag/15% Au) in 70% HNO$_3$ for 30 min. The dealloyed foils were filtered over a quartz frit (fitted within a quartz tube reactor), washed thoroughly with water, and dried at 80° C. under flowing helium.

Nanoporous gold ingots were prepared from Ag—Au alloy disks with a diameter of approximately 5 mm and a thickness of 200-300 μm through chemical etching with HNO$_3$. The parent Ag—Au alloy disks, with a composition of 70% Ag and 30% Au, were prepared using procedures known in the art.

Hollow nanoporous gold shells were synthesized through adaptations of a method for producing nanoporous Au monoliths (Hudson, J. E. et al. *J. Phys. B: At. Mol. Opt. Phys.* 2004, 37, 445). First, 13 nm Au nanoparticles were synthesized according to a reported procedure (Nyce, G. W. et al. *Chem. Mater.* 2007, 19, 344). Subsequently, 11 μm PS/DVB spheres (3.0 mL, 10 wt. % solution) were added to 30 mL of the as-synthesized 13 nm Au nanoparticle solution in a round bottom flask and stirred overnight. The Au nanoparticle-coated PS/DVB spheres (pink) were then separated from residual Au nanoparticles (red) via centrifugation. The separated Au nanoparticle-coated PS/DVB spheres were then resuspended in Millipore H$_2$O (300 mL) in a round bottom flask. To this mixture, polyvinylpyrrolidone (PVP, 4 g) was added with rapid stirring, followed by hydroxylamine hydrochloride (800 mg). With continued stirring, HAuCl$_4$·3H$_2$O (540 mg) was added to the solution, stirred rapidly for 5 minutes, and then stirred gently for an additional 1.5 hours. The contents of the flask were transferred to conical tubes and allowed to sediment. The supernatant was removed and discarded. The separated Au-coated PS/DVB microspheres were resuspended in Millipore H$_2$O (250 mL) in a round bottom flask. With rapid stirring, PVP (3.0 g) was added to this mixture, followed by AgNO$_3$ (1.140 g) and ascorbic acid (2.94 g), sequentially. The solution was allowed to stir for 10 minutes, and then left to react for one hour without stirring. The microspheres were isolated by allowing the microspheres to sediment and then removing the supernatant and using the minimum required volume of H$_2$O to combine the microparticles in a single conical tube. Any additional supernatant was then removed, and the microspheres were allowed to dry. The dried Ag/Au-coated PS/DVB microspheres were then calcined in air to alloy the Ag and Au and to remove the PS/DVB core and any residual carbon-containing species from the synthesis procedure, such as PVP. The dried microspheres were loaded into the flow reactor tube furnace in a glass reactor tube with a quartz frit (with the spheres lightly sandwiched between two pieces of deactivated glass wool) and ramped from 30°

C. to 450° C. (10° C./min) in air at a flow rate of 39 mL/min. During the calcination process, the bottom of the reactor tube was connected to a trap and then vented rather than running through the remaining reactor lines, because PS/DVB recondenses as it leaves the tube, and would otherwise contaminate the reactor. The spheres were calcined at 450° C. in air for one hour and then cooled to room temperature. The ratio of Ag:Au in the resulting Ag/Au hollow shells is 85:15 by EDS. The annealed hollow AgAu shells were etched in concentrated nitric acid for approximately 48 hours, replacing the acid with fresh nitric acid every 8 hours, until the total residual silver in the shells was 1-3%. The shells were then washed well with Millipore water and allowed to dry.

Example 3. Activation of Nanoporous Gold Catalysts Useful for Oxidative Coupling of Primary Alcohols The nanoporous gold ingots, foils, or shells were loaded into the flow reactor tube furnace in a glass reactor tube (0.4 inch internal diameter) with a quartz frit (with the nanoporous gold material lightly sandwiched between two pieces of deactivated glass wool) and ramped from 30° C. to 150° C. (10° C./min) in a flow of 30 g/Nm$^3$ of ozone in a ~50% $O_2$/He gas mixture at a total flow rate of 50 mL/min and then held at 150° C. for one hour at the same flow composition. The ozone treated nanoporous gold catalysts were cooled to 50° C. and then ramped from 50° C. to 150° C. (10° C./min) in 10% methanol/20% $O_2$ in He at a total flow rate of 50 mL/min. Methanol was introduced into the reactor via syringe pump injection into a heated line or by bubbling He through a flask of methanol in combination with a temperature controlled condenser. This ramp under reaction conditions was monitored by GC-MS to observe the gradual increase in methyl formate production as well as the initial production of a small amount of carbon dioxide.

Reproducible activation of all three forms of nanoporous gold (ingots, foils, and shells) was achieved using the procedure described above (FIGS. 2 and 8). The specific activity and selectivity of the three types of nanoporous gold materials for oxidative catalysis was evaluated using the oxidation of methanol to methyl formate as a test reaction, because the catalytic activity of nanoporous gold for this reaction is already well-characterized for monolithic nanoporous gold ingots (Wittstock, A. et al. *Science* 2010, 327, 319). Fresh samples of each of these materials could be activated without fail, whereas the previous method of activation of the ingots in CO/$O_2$ or methanol/$O_2$ mixtures (sometimes with added CO) at temperatures from 30-80° C. failed more often that it succeeded (Wittstock, A. et al. *Science* 2010, 327, 319; Stowers, K. J. et al. *J. Catal.* 2013, 308, 131; Röhe, S. et al. *Surf. Sci.* 2013, 609, 106).

The activity of the nanoporous gold materials for the oxidation of methanol was allowed to stabilize (~12-24 hours) before the materials were used in any further experiments. All experiments were conducted at a total flow rate of 50 mL/min and a temperature of 150° C. He was used as a carrier gas, and the alcohols were introduced via syringe pump injection into a heated line on the reactor or by bubbling He through a flask of the corresponding alcohol in combination with a temperature controlled condenser. Representative GC-MS spectra for each reaction are shown below (FIGS. 6, 9, and 10).

Figure 7A:
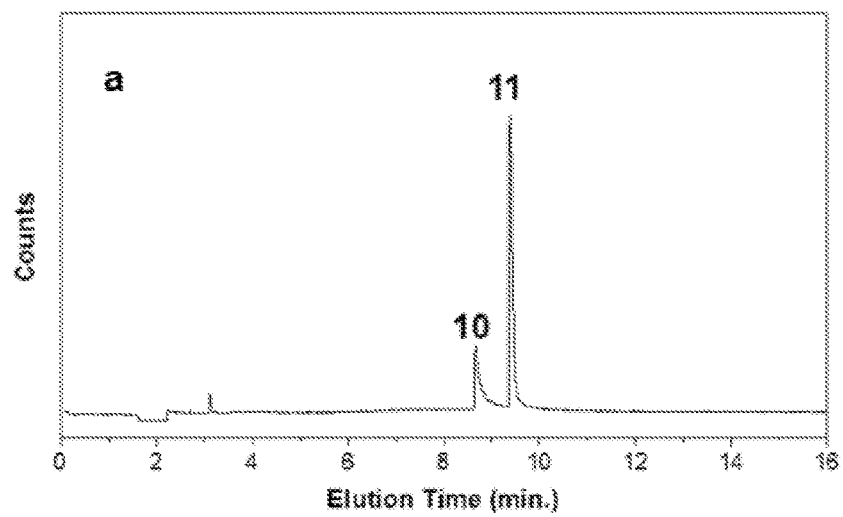
FIGS. 7a-7c show GC chromatogram (a) and MS spectra (b-c) for products not observed: (10) formic acid and (11) acetic acid.
Figure 7B:
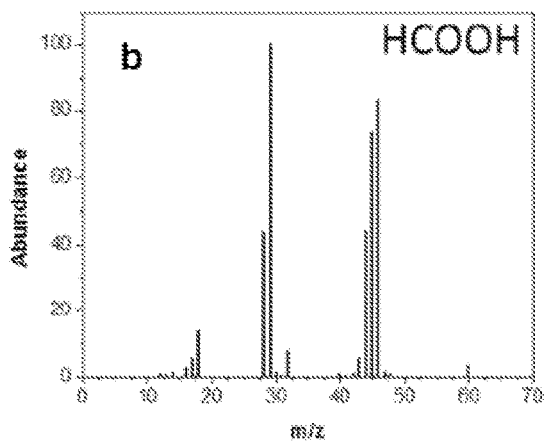
Figure 7C:
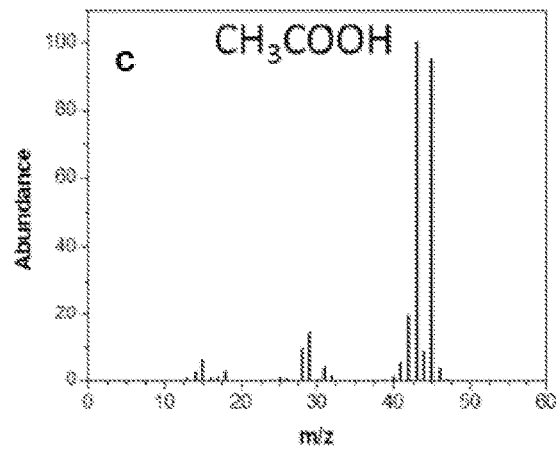
Figure 8A:
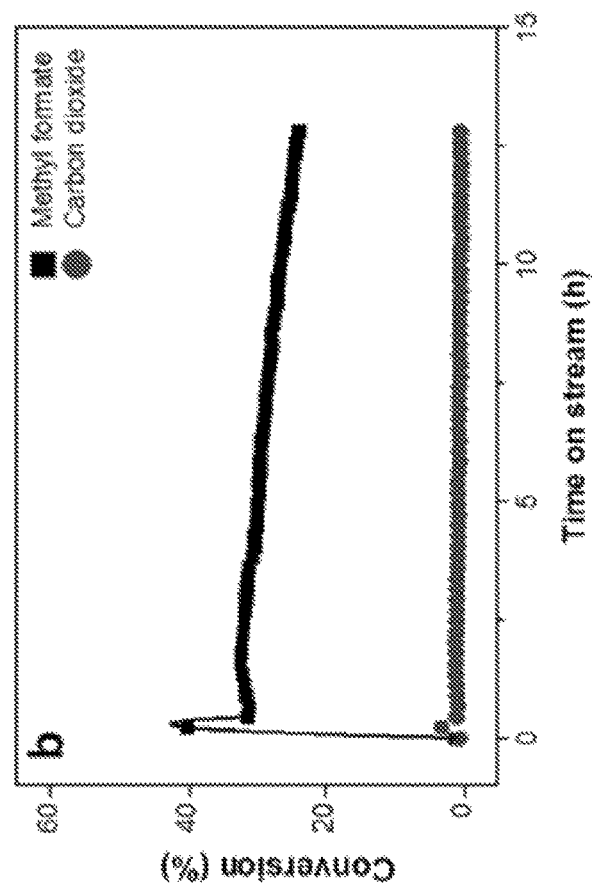
FIGS. 8a-8b are graphs of conversion versus time for the initial activation of (a) nanoporous gold ingot and (b) nanoporous gold foil catalysts in the oxidation of methanol after ozone treatment. A temperature ramp from 50-150° C. takes place between the first and second time points. Mass of ingot: 35 mg, mass of foils: 11 mg. Conditions: 10% methanol and 20% $O_2$ in He, flow rate: 50 mL/min, 150° C.
Figure 8B:
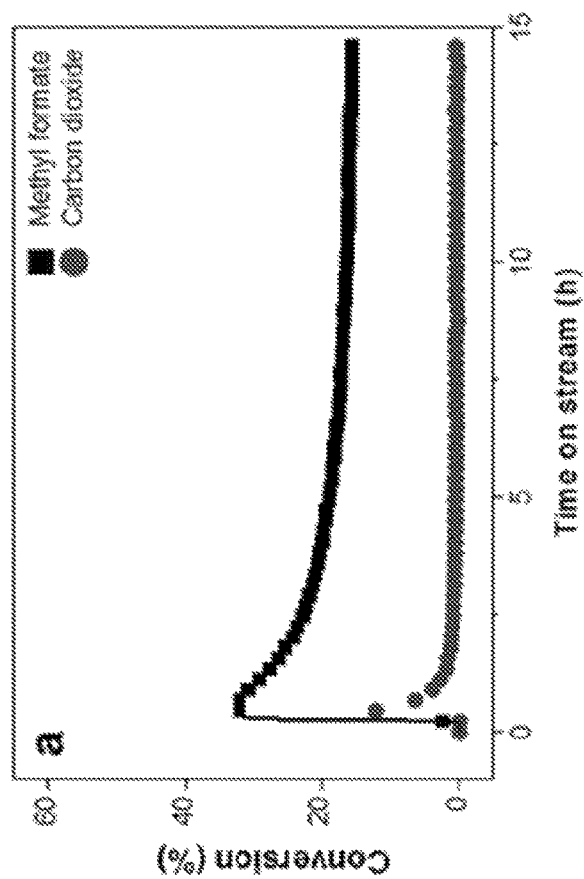
Figure 9B:
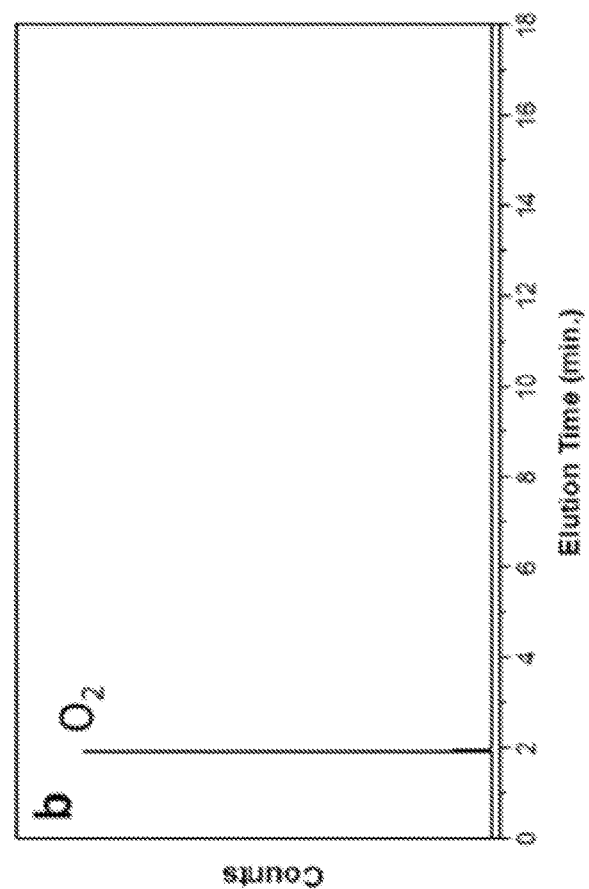
FIGS. 9a-9e show representative GC-MS data for 1-butanol oxidation on ozone-activated nanoporous gold. (a) GC chromatogram showing peaks for (7) butyraldehyde, (8) 1-butanol, and (9) butyl butyrate. Inset: enlarged view of butyl butyrate peak. MS spectra for each of the peaks are shown in (c)-(e). (b) TCD chromatogram showing a peak for excess $O_2$.
Figure 9A:
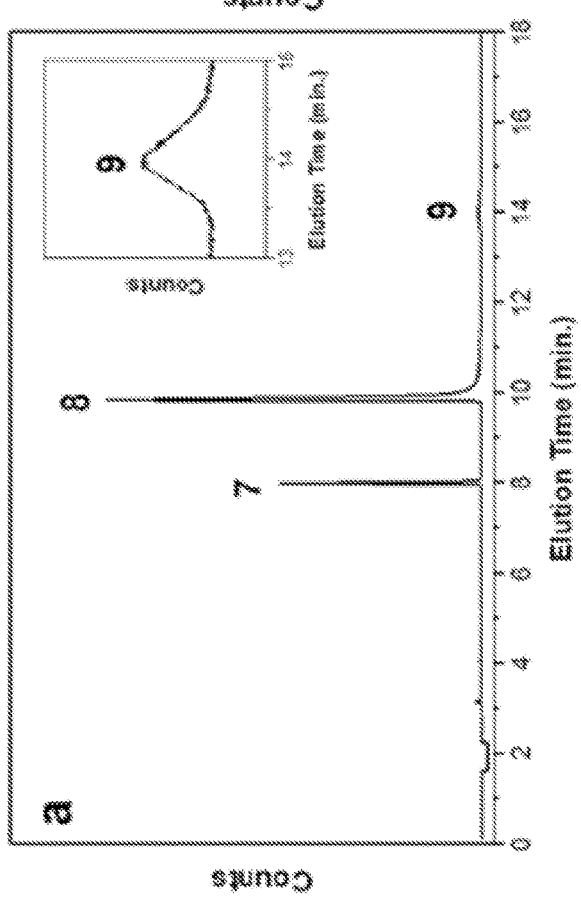
Figure 9E:
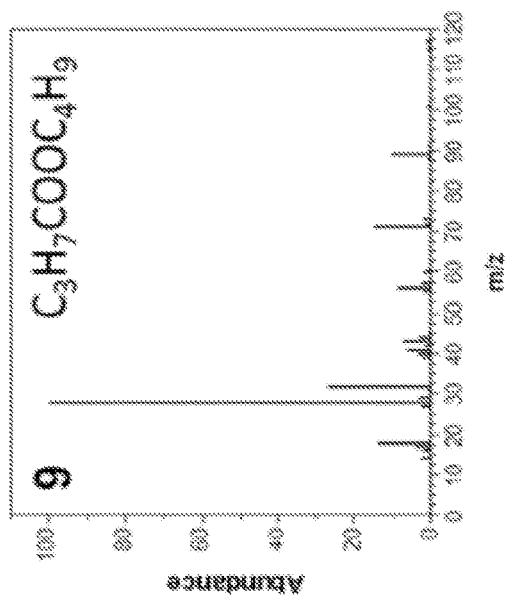
Figure 9D:
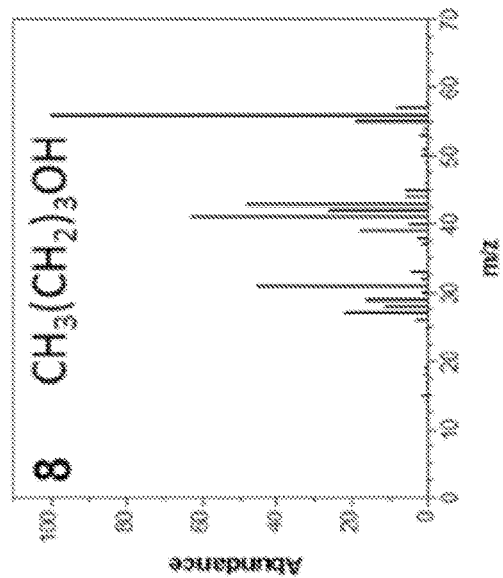
Figure 9C:
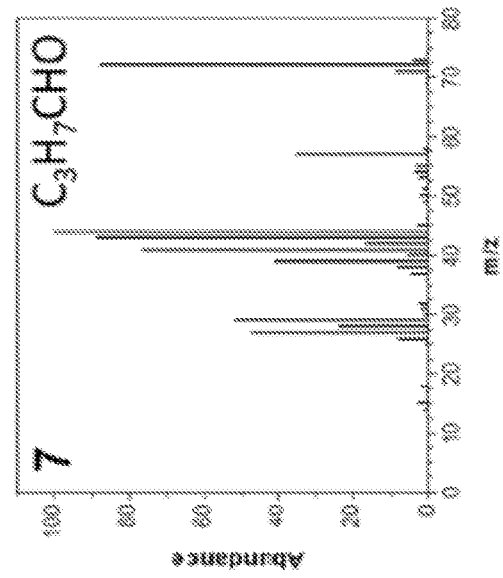
Figure 10B:
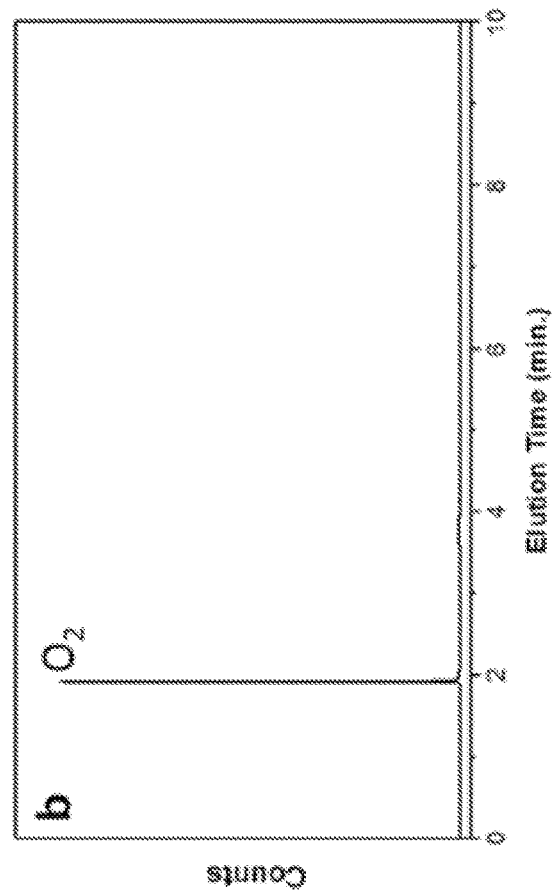
FIGS. 10a-10e show representative GC-MS data for ethanol oxidation on ozone-activated nanoporous gold. (a) GC chromatogram showing peaks for (4) acetaldehyde, (5) ethanol, and (6) ethyl acetate. MS spectra for each of the peaks are shown in (c)-(e). (b) TCD chromatogram showing a peak for excess $O_2$.
Figure 10A:
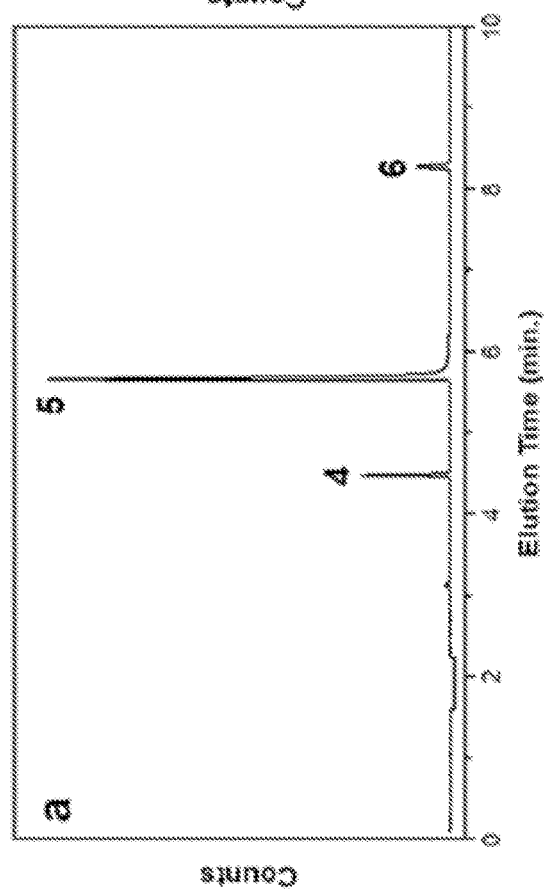
Figure 10E:
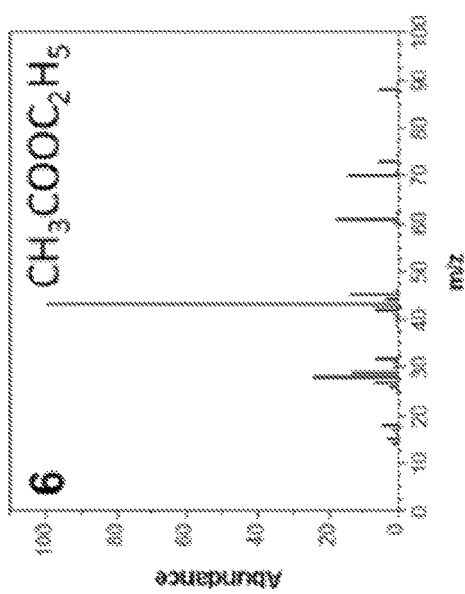
Figure 10D:
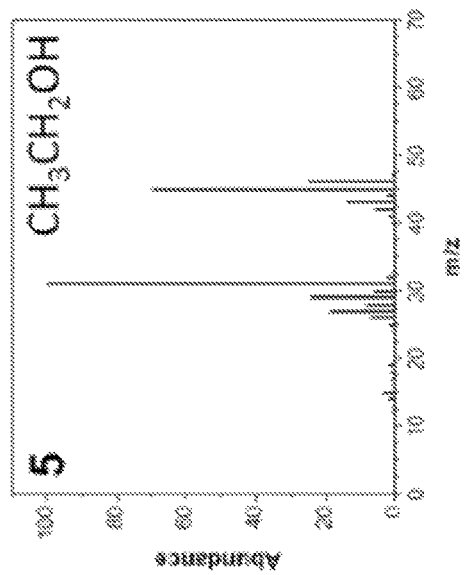
Figure 10C:
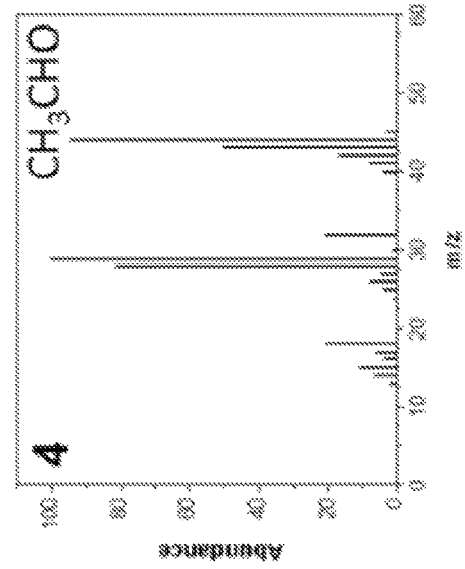
Figure 11A:
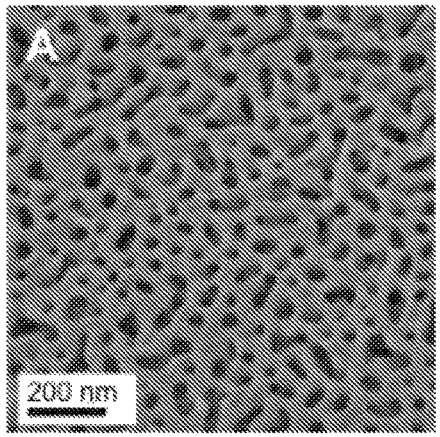
FIGS. 11a-11d show a series of images of a 12 karat gold foil (a) after dealloying in nitric acid, (b) after ozone treatment (70 mL/min, 20 g/Nm³) at 150° C. for 1 hour, (c) after exposure of ozone-treated foil to 6.5% methanol/20% $O_2$ at room temperature for 30 minutes, and (d) after exposure to reaction conditions of 6.5% methanol/20% $O_2$ at 150° C.
Figure 11B:
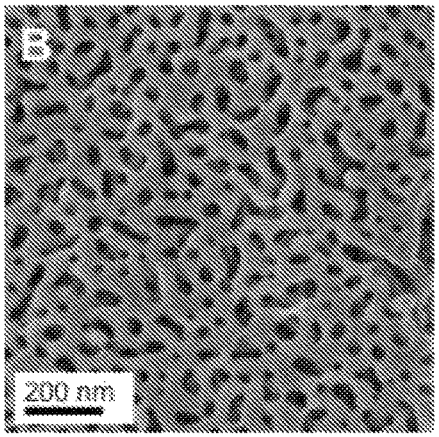
Figure 11C:
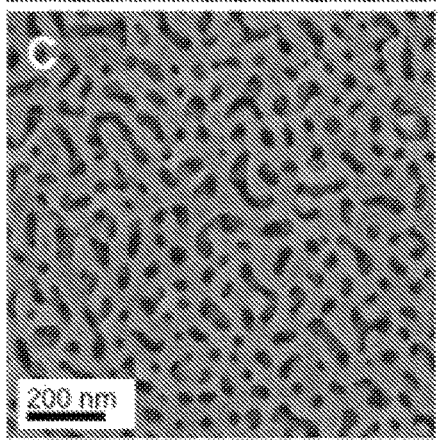
Figure 11D:
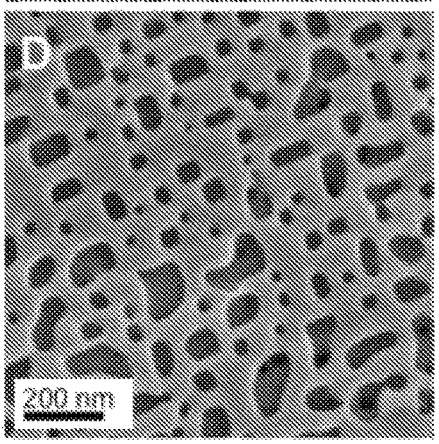

All three ozone-activated materials catalyzed the selective oxidative coupling of methanol to methyl formate in flowing gas composed of 10% methanol and 20% $O_2$ in He, with a total flow rate of 50 mL/min at 150° C. with 100% selectivity. No other partial oxidation products were detected, including formaldehyde or formic acid (FIGS. 6 and 7). There was no quantifiable production of the combustion product, $CO_2$, except during activation (FIGS. 2 and 8).

Figure 3:
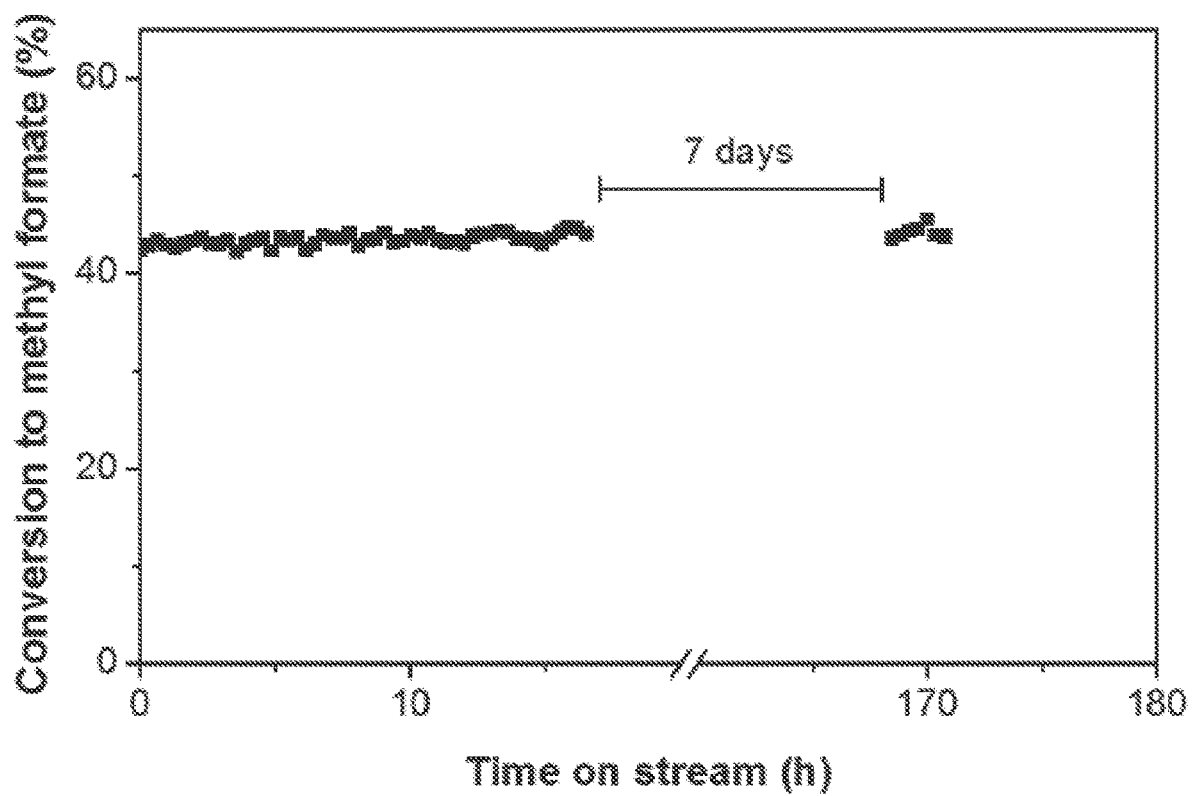
FIG. 3 is a graph showing the steady conversion of methanol to methyl formate over the course of greater than seven days on activated nanoporous gold shells, after stabilization (~50 mg of catalyst). Conditions: 10% methanol and 20% $O_2$ in He, flow rate: 50 mL/min, 150° C.
Figures 4A, 4B:
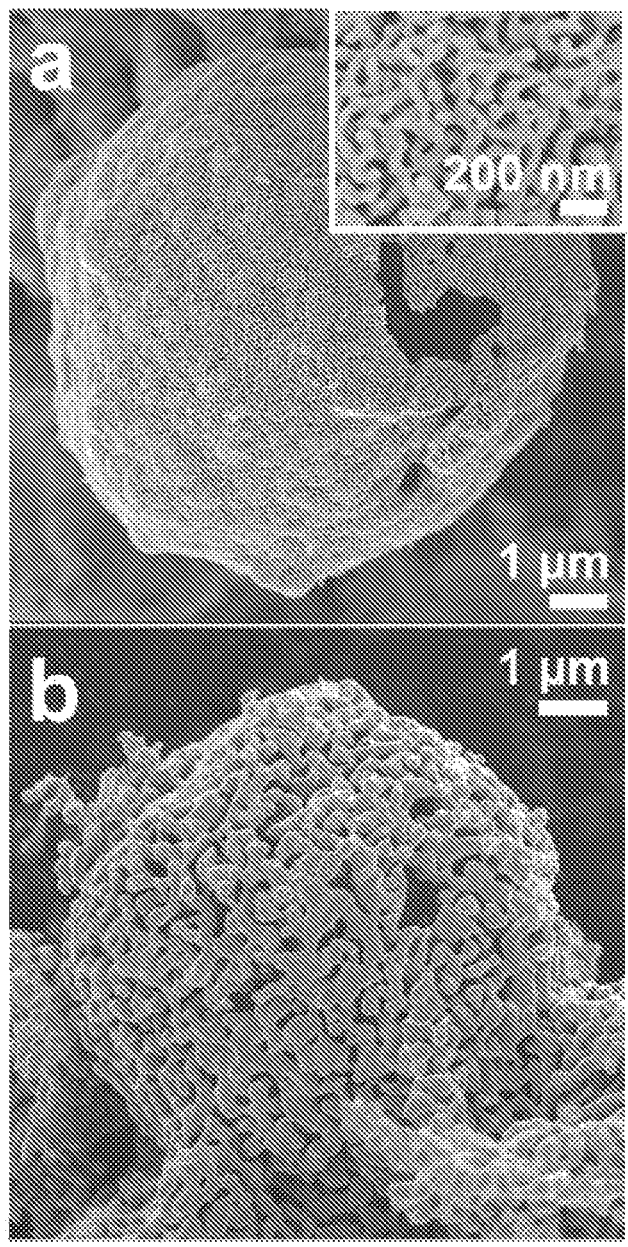
FIGS. 4a-4b show SEM images of the ligament sizes of nanoporous gold shells before exposure to reactant gases (a) and after one month on stream (b). Inset in (a): high-magnification image of the ligament structure of the nanoporous gold shell in (a).

These catalytic materials, activated in the manner described, show sustained and reproducible catalytic activity and selectivity. The catalysts exhibited an initial equilibration period of approximately 24 hours during which the activity of the catalyst increased and then gradually decreased to a stable value. This activation and stabilization period is shown in FIG. 2 for ~10 mg of the nanoporous gold shell catalyst, which was well dispersed in the reactor bed and thus exhibited a high rate of methanol conversion. Corresponding data for the ingots and foils is presented in FIG. 8. The data in FIG. 3, which shows sustained conversion of methanol over time, was obtained using five times the amount of the nanoporous gold shell catalyst used in FIG. 2 (~50 mg) and thus yielded a higher conversion. The stable conversion rates of methanol for the foils and well-dispersed shells were 0.091 mmol s$^{-1}$ g$^{-1}$ and 0.083 mmol s$^{-1}$ g$^{-1}$, respectively, which are nearly five times higher than the specific reaction rate on the ingots (0.017 mmol s$^{-1}$ g$^{-1}$). The higher rates confirm that, as a result of their thinner and more open morphologies, the shells and foils do remove some of the mass transport limitations inherent to the ingots. Further, the fact that the reaction rates on the foils and shells are very similar suggests that mass transport limitations are negligible for these materials, since their characteristic pore depths differ significantly. The reaction rate on the ingots is comparable to the activity previously reported at 80° C. for ingots activated in methanol and $O_2$ at room temperature (0.022 mmol s$^{-1}$ g$^{-1}$) (Wittstock, A. et al. *Science* 2010, 327, 319). After one month of use, the surface area of the nanoporous gold shells decreased by approximately a factor of 10—from 7.2 m$^2$/g to 0.7 m$^2$/g (BET), presumably due to agglomeration and a change in morphology; the ligament diameter increased from 80±20 nm to 250±80 nm (SEM) (FIG. 4). Over the same period, the surface area of the nanoporous gold ingots decreased from 4.6 m$^2$/g to 2.8 m$^2$/g (BET). A minor amount of coarsening of the ligaments (from 80±20 nm to 115±25 nm) occurred on the nanoporous gold shells during the initial activation in ozone and one to two hours under reaction conditions. After four days of reaction the ligament size of the shells had increased to 140±40 nm. These observations indicate that a significant amount of coarsening occurs during the early stages of reaction (Qian, L. H. et al. *Appl. Phys. Lett.* 2007, 91, 083105) and that the resulting rearrangement of the structure and composition of the catalyst surface may be important for the activity of the catalyst for methanol coupling in these materials. Notably, there is not a significant amount of coarsening as a result of the initial ozone treatment (Biener, J. et al. *Langmuir* 2010, 26, 13736)—the coarsening occurs under reaction conditions creating the active catalyst.

Under a flow of 5.36% 1-butanol and 20% $O_2$ in He (50 mL/min), butyl butyrate was produced with selectivities of 20.6%, 11.9% and 16.4%, for the ingots, foils, and shells, respectively, with butyraldehyde as the other only other reaction product (FIG. 9).

On ozone-activated nanoporous gold the selectivity to ethyl acetate in the self-coupling of ethanol (5.23% ethanol/20% $O_2$ in He, 50 mL/min) was stable at 36.1% for the ingots, 22.1% for the foils, and 20.2% for the shells, with the remaining product being acetaldehyde (FIG. 10), whereas it has been reported that the self-coupling of ethanol by reactant-activated nanoporous gold shows low and variable selectivity for ethyl acetate production from day to day (Kosuda, K. M. et al. *Angew. Chem. Int. Ed.* 2012, 51, 1698).

Example 4. Flow Reactor Analysis of Alcohol-Aldehyde Cross-Coupling Reactions Catalyzed by Ozone-Activated Nanoporous Gold Catalysts The npAu ingots were placed on a porous quartz frit that was supported inside a quartz tube reactor (10.5 mm I.D.) by a plug of quartz wool. Prior to reaction, the catalyst was activated by ozone treatment followed by exposure to flowing methanol and oxygen at 150° C. under ambient conditions. The catalyst was kept under methanol oxidation conditions at 150° C. for up to 12 hours prior to testing cross-coupling activity. All organics were introduced into the reactor via saturated He flow from temperature-controlled bubbler-condenser assemblies. The gas phase composition was controlled by mass flow controllers (MKS Instruments). The oxygen concentration was kept at 20% during all experiments. The gas phase composition was monitored by GC-MS (Agilent 5975C and Agilent 7890A) equipped with HP-PLOT Q and CARBONPLOT columns. The stability of the coupling reactions was periodically tested for up to 24 h with no decrease in activity.

Figure 14A:
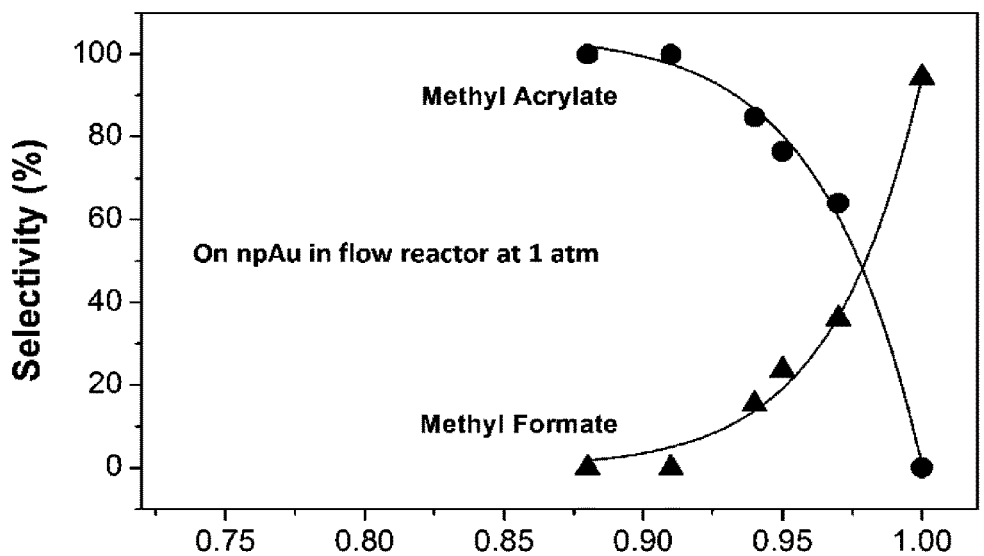
FIGS. 14a-b show the selectivity of cross-coupling reactions performed over (a) an activated npAu ingot of methanol with acrolein in a continuous flow reactor. Reaction conditions: 5% R═O (Total)-20% $O_2$—He, flow rate 50 mL/min; catalyst weight ~35 mg; reaction temperature 150° C., (b) 0.1 ML of atomic oxygen was dosed at 300 K via ozone exposure Au(110), subsequently the reactants were dosed at 120 K.
Figure 14B:
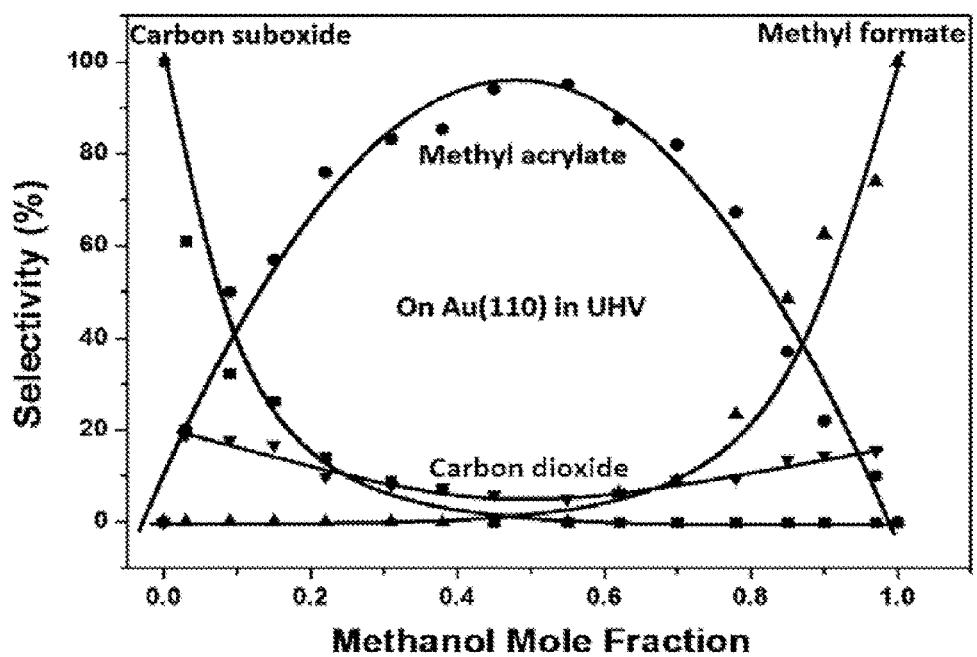

The stable coupling of methanol with acrolein to form methyl acrylate was observed at high methanol mole fractions in a continuous flow reactor at 150° C. Two major coupling products were observed—methyl acrylate and methyl formate—with the relative distribution depending on the ratio of acrolein to methanol in the gas feed (FIG. 14*a*). A maximum selectivity for methyl acrylate formation of 100% is achieved at a methanol mole fraction of 0.88; the acrolein conversion decreases with increasing cross-coupling selectivity and is ~2% at the methanol mole fraction of 0.88. Small amounts of $CO_2$ (less than 5-6%) are also observed at high methanol mole fractions. A comparison of the product selectivity based on the Au(110) results shows that the dependence of the selectivity on reactant composition is completely different on npAu under ambient pressure flow conditions and Au(110) under the procedures used in the model catalyst experiments (FIG. 14*b*). Under those conditions a selectivity ~95% is observed for a methanol mole fraction ~0.5, when the adsorption of the reactants is performed sequentially (methanol first) at 120K.

Figure 15A:
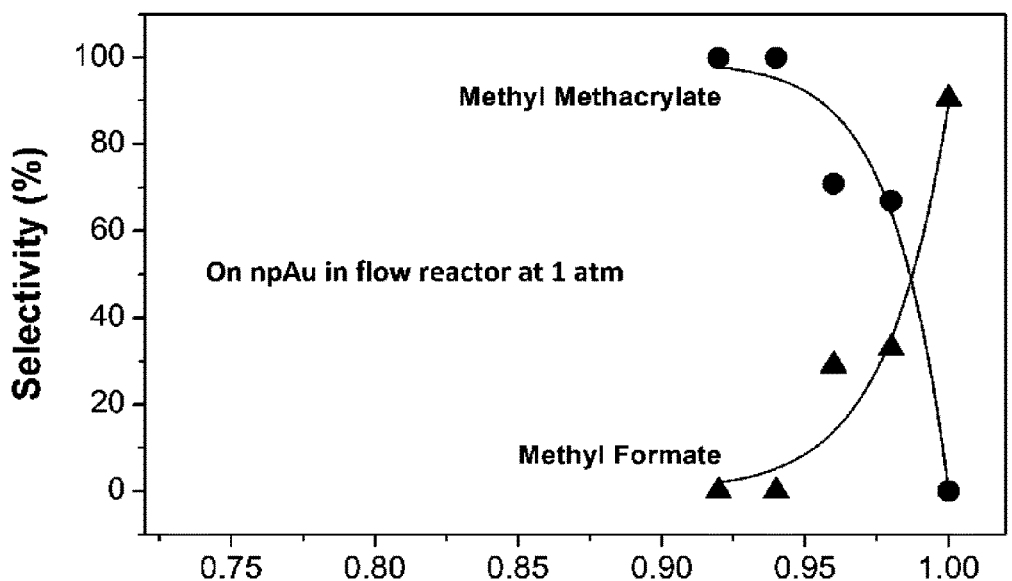
FIGS. 15a-b show the selectivity of cross-coupling reactions performed over (a) an activated npAu ingot in the catalytic reaction of methanol with methacrolein in a continuous flow reactor. Reaction conditions: 5% R═O (Total)-20% $O_2$—He, flow rate 50 mL/min; catalyst weight ~35 mg; reaction temperature 150° C., (b) 0.1 ML of atomic oxygen was dosed at 300 K via ozone exposure Au(110), subsequently the reactants were dosed at 120 K.
Figure 15B:
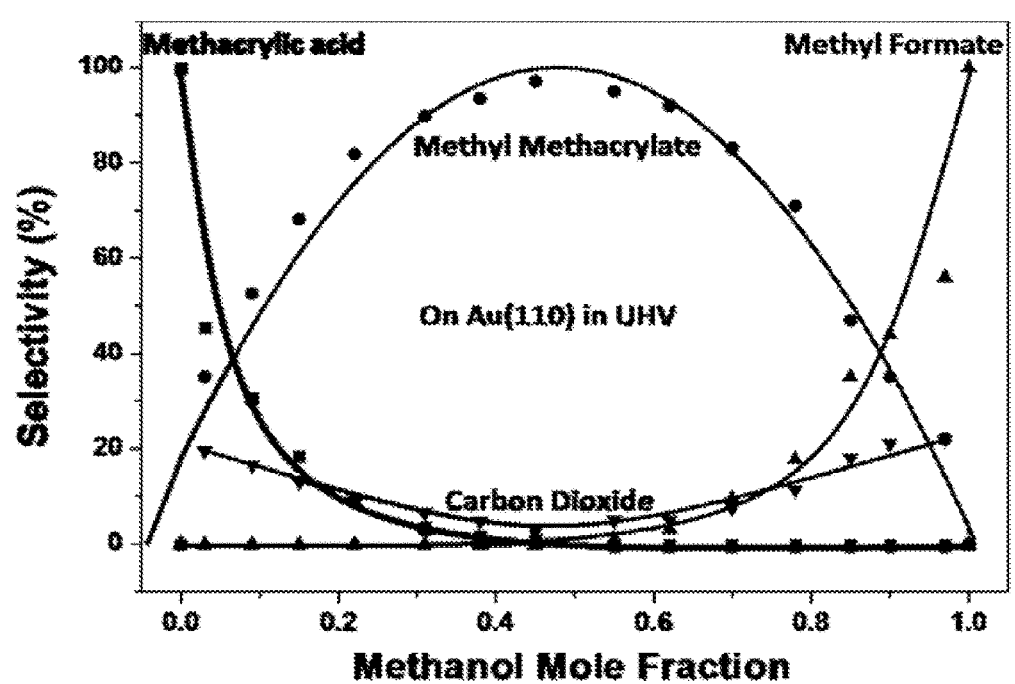

The coupling of methanol with methacrolein also occurs efficiently at high methanol mole fractions over npAu in flow reactor at ambient pressure and 150° C. The maximum selectivity of methyl methacrylate of 100% is observed at a methanol mole fraction of 0.92 (and a methacrolein conversion of ~1%) (FIG. 15*a*). As the methanol mole fraction is increased, the cross-coupling selectivity (to methyl methacrylate) decreases and self-coupling of methanol to methyl formate becomes dominant. As with acrolein, the product selectivity on npAu under ambient pressure flow conditions differs significantly from that on Au(110) (FIG. 15*b*).

Figure 16A:
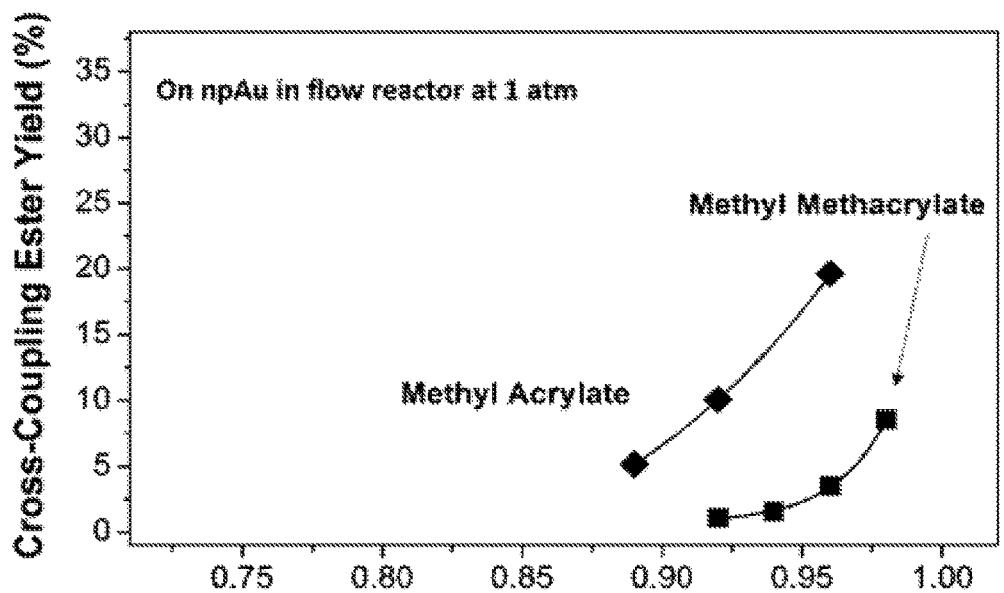
FIGS. 16a-b show the yield of esters achieved from cross-coupling reactions (based on unsaturated aldehyde conversion to methyl ester product) over (a) an activated npAu ingot in the catalytic reaction of methanol with acrolein, and methacrolein (same conditions as those described in FIGS. 14a-b and 15a-b) in a continuous flow reactor, (b) 0.1 ML of atomic oxygen was dosed at 300 K via ozone exposure on Au(110) with subsequent dosing of the reactants at 130 K (methanol first).

For the flow reactor experiments, while the product distribution of the reactions for methyl acrylate compared to methyl methacrylate in FIGS. 14*a* and 15*a* vary in a similar fashion with methanol mole fraction, the cross-coupling rates are generally higher for methyl acrylate. This is demonstrated in FIG. 16*a*, which shows that the yield of the methyl acrylate is consistently higher than methyl methacrylate across all methanol mole fractions.

Figure 16B:
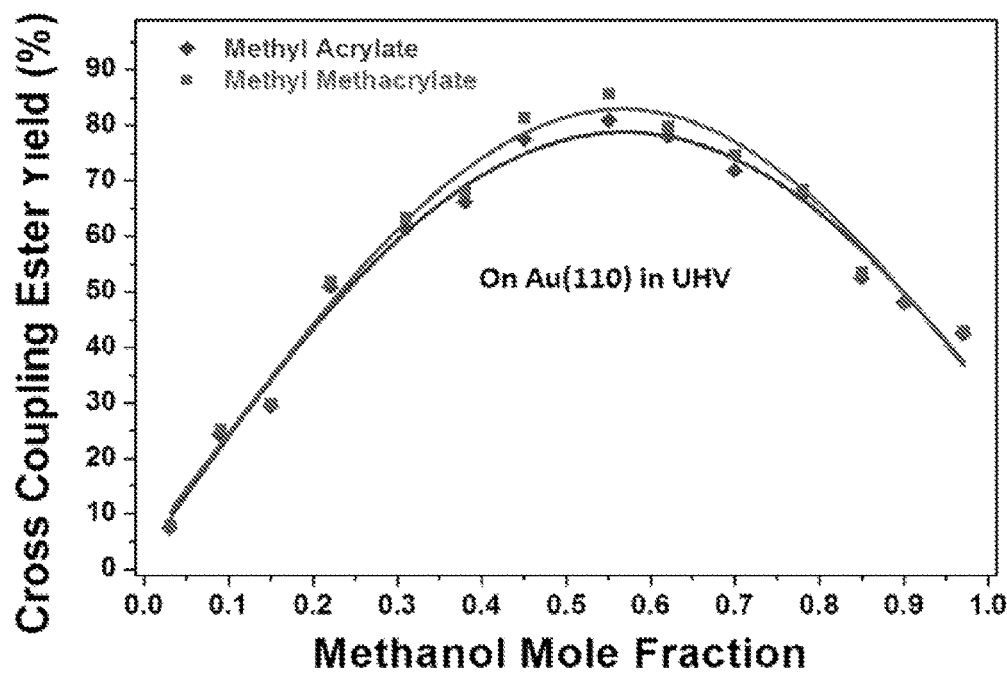

The yields towards ester formation, measured under UHV conditions (FIG. 16*b*) for both acrolein and methacrolein show a maximum of 80-90%, at 0.5 methanol mole fraction. In order to explain these differences, the competitive adsorption and displacement of methanol and the aldehydes was examined at a surface temperature of 120 K, as has been reported for alcohol cross-coupling. Neither displacement nor true competition for adsorbed atomic oxygen was observed in either case. After sequentially adsorbing various mixtures of acrolein and methanol on either 0.1 ML or 0.05 ML of O/Au(110) interfaces, the recorded methyl acrylate intensity was always the maximum expected for the 50%-50% ratio of the two adsorbates on the surface.

The comparison between the alcohol-alcohol cross-coupling reaction and the equivalent alcohol-aldehyde reaction, shows that the maximum ester selectivity is 4-5 times higher for the alcohol-aldehyde case. This observation had been explained, by proposing that the binding strength of the alkoxy on Au plays an important role in the maximum selectivity observed between alcohol cross coupling reactions. However, the absence of this competition process in alcohol-aldehyde cross-coupling leads to higher ester selectivities.

Example 5. Flow Reactor Analysis of Alcohol Self- and Cross-Coupling Reactions Catalyzed by Ozone-Activated Nanoporous Gold Catalysts Ingots of npAu (diameter 5 mm, thickness 200-300 μm) were prepared by the chemical etching of $Ag_{70}Au_{30}$ bimetallic alloy disks in concentrated nitric acid. The average ligament size of the as-prepared npAu is ~30 nm, and the BET surface area is ~4.5 $m^2$/g.

The npAu ingots were placed on a porous quartz frit that was supported inside a quartz tube reactor (10.5 mm I.D.) by a plug of quartz wool. This configuration was used for all catalyst pretreatment and testing. Prior to reaction, the catalyst was activated by ozone treatment. Briefly, the reactor temperature of was ramped (10° C./min) from 25° C. to 150° C. in a flow (70 mL/min) of 50 g/$Nm^3$ of ozone in a carrier gas of $O_2$ and He. The catalyst was held at 150° C. for 1 h, then cooled to room temperature (in the ozone mixture). Following ozone treatment, the catalyst was activated for alcohol oxidation by establishing a flow of 6.5% MeOH-20% $O_2$/He (50 mL/min) at 25° C. and ramping the temperature to 150° C. (ramp rate 10° C./min). The catalyst was kept under methanol oxidation conditions at 150° C. for up to 12 hours prior to testing cross-coupling activity. All organics were introduced into the reactor via saturated He flow from temperature-controlled, bubbler-condenser assemblies. The gas phase composition was controlled by mass flow controllers (MKS Instruments). The oxygen concentration was kept at 20% during all experiments. The gas phase composition was monitored by GC-MS (Agilent 5975C and Agilent 7890A) equipped with HP-PLOT Q and CARBONPLOT columns. The stability of the coupling reactions was periodically tested for up to 24 h with no decrease in activity.

Figure 17A:
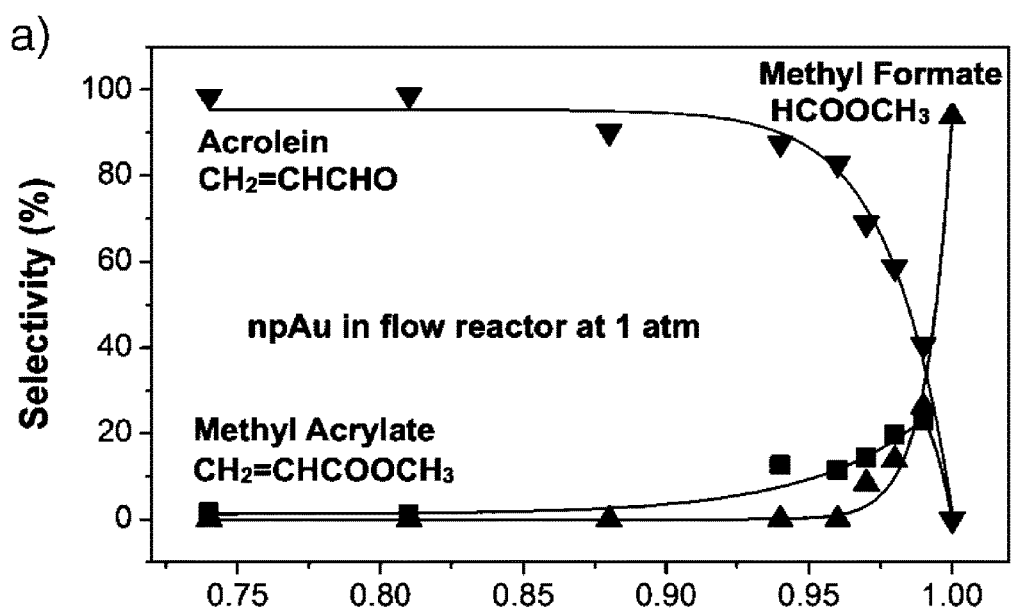
FIGS. 17a-b show the dependence of the selectivity of coupling of allyl alcohol and methanol on methanol mole fraction over (a) an activated npAu sample in a flow reactor and (b) on an oxygen pre-covered Au(110) surface (0.1 ML) in UHV. The flow reactor conditions were those typically used for methanol coupling: 5% R—OH (Total)-20% $O_2$—He, flow rate 50 mL/min; catalyst weight ~35 mg; reaction temperature 150° C.
Figure 17B:
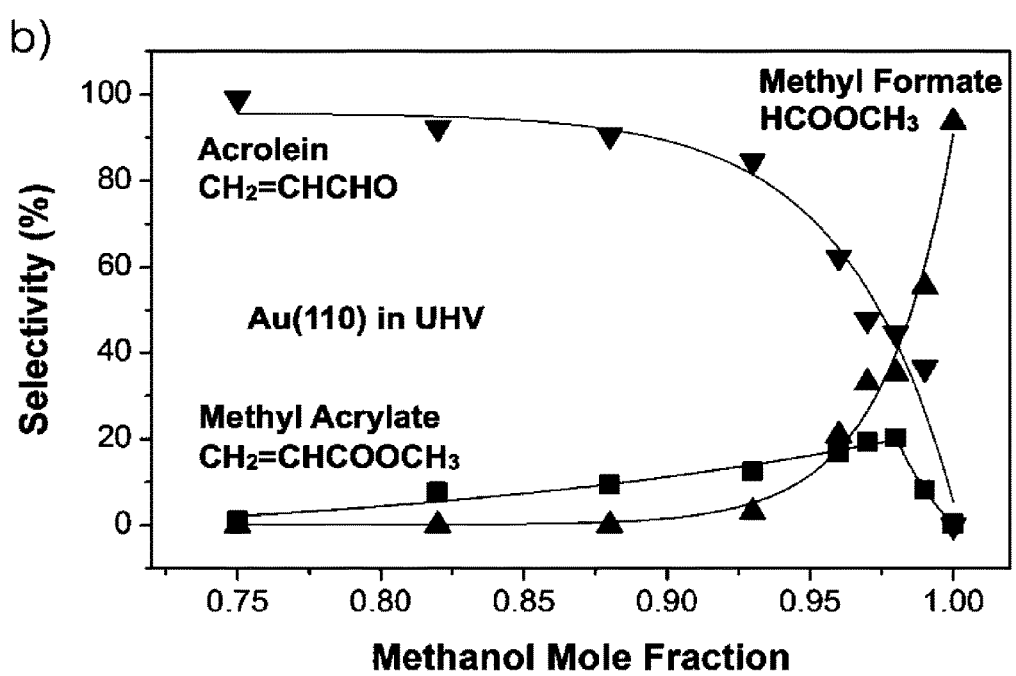

The continuous, catalytic coupling of methanol with allyl alcohol to form methyl acrylate is observed at high methanol mole fractions over npAu in a continuous flow reactor at 150° C., in agreement with results of the model experiments (FIGS. 17*a-b*). The reactions conditions used were 5% total alcohol, 20% $O_2$ in a flow of He (50 mL/min).

The relative amounts of the two major products—acrolein and methyl acrylate—depend on the ratio of allyl alcohol to methanol in the gas feed, as predicted from the model studies (FIG. 17*a*). A maximum methyl acrylate selectivity of 23% (with a total allyl alcohol conversion of 67%) is achieved at a methanol mole fraction of 0.99. Small amounts of $CO_2$ (less than 10%) are also observed at high methanol mole fractions and no other products are observed by GCMS analysis (self-coupling of allyl alcohol is not observed under any conditions). Methyl acrylate is first detected for methanol mole fractions above ~0.8. Acrolein is the sole product for lower methanol mole fractions indicating that allyloxy, derived from allyl alcohol, is the predominant adsorbed species (FIG. 17a). At very high methanol mole fractions (>0.95), methyl formate is also produced (FIG. 17a), indicating that methoxy is present on the surface under these conditions. Reaction of pure methanol yields methyl formate as the only product, as expected.

Remarkably, the dependence of the product selectivity on the methanol mole fraction is essentially the same for the coupling reaction on O-activated Au(110) in UHV and during catalytic conditions on npAu under atmospheric pressure (FIGS. 17a-b). This result is clear evidence that the mechanism derived from model studies, including the concept that competition for reaction sites governs the relative coverages of the alkoxide intermediates, is directly applicable to working catalytic conditions.

The equilibrium constant for the competition of methanol and allyl alcohol for surface sites (Equation 1) on the npAu catalyst is estimated to be 100 (Table 3, below), which is ~10 times greater than the analogous competition between methanol and ethanol and ~3 times greater than competition between methanol and 1-butanol. This estimate assumes that a 1:1 ratio of methoxy to allyloxy is necessary to optimize cross coupling selectivity, which is achieved at a methanol mole fraction of 0.99 (given $K_{eq}$=100). While this is a rough estimate, it provides an order of magnitude comparison of the binding efficacy of allyl alcohol, which contains a C=C bond, compared to saturated alkoxides, as shown in Table 3.

TABLE 3

Ordered gas phase stabilities of various alkoxide intermediates and measured equilibrium constants ($K_{eq}$) for methanol cross-coupling on npAu.

| Conjugate Base | Gas Phase Acidity[a] (kJ/mol) | $K_{eq}$[b] |
|---|---|---|
| Methoxy | 1597 ± 6 | — |
| Ethoxy | 1580 ± 8 | 10 |
| Butoxy | 1570 ± 8 | 30 |
| Allyloxy | 1563 ± 12 | 100 |
| Methallyloxy | — | 450 |

[a]Gas phase acidity is defined as $\Delta H_r$ for BH → B⁻ + H⁺ (NIST database).
[b]$K_{eq}$ determined from experimental results shown in FIG. 19.

Figure 18A:
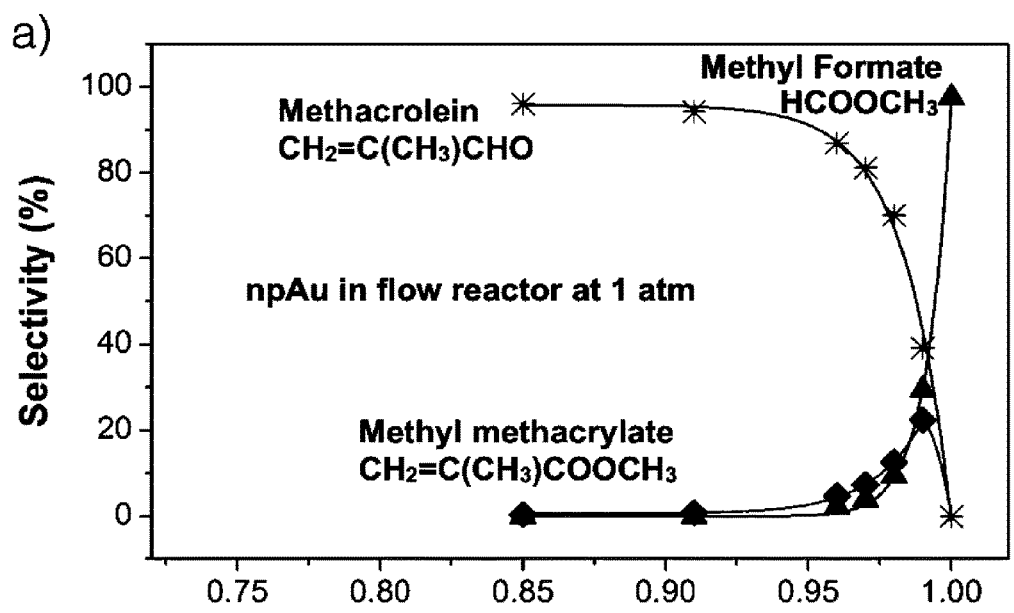
FIGS. 18a-b show the selectivity of cross-coupling reactions of methallyl alcohol and methanol over (a) an activated npAu sample in a flow reactor and (b) on an oxygen pre-covered Au(110) surface (0.1 ML) in UHV. Flow reactor conditions: 5% R—OH (Total)-20% $O_2$—He, flow rate 50 mL/min; catalyst weight ~35 mg; reaction temperature 150° C.
Figure 18B:
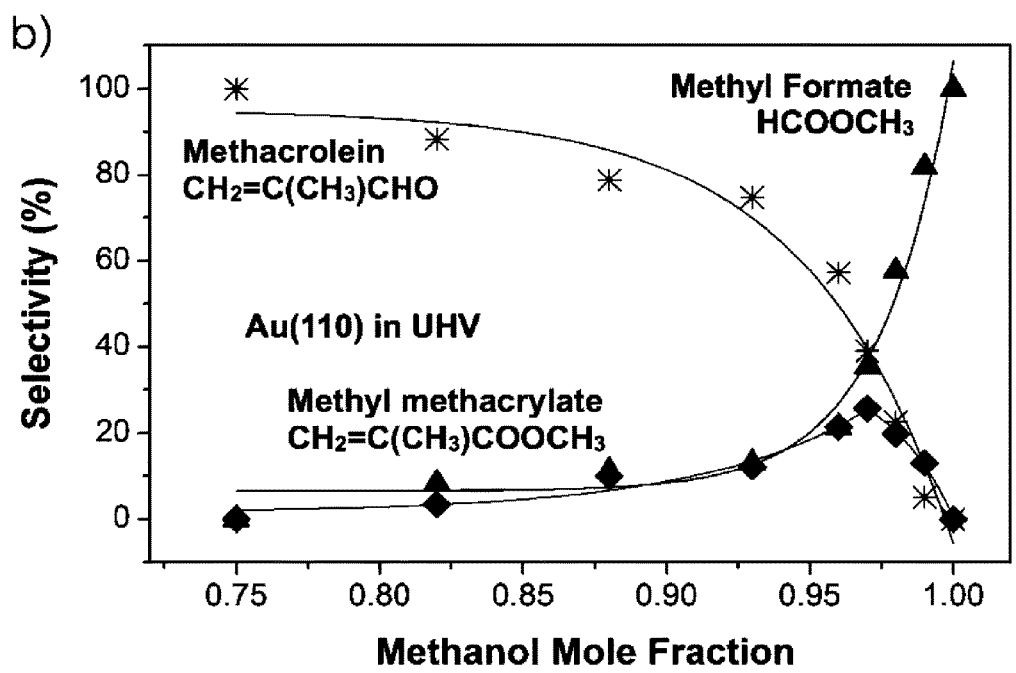

The coupling of methanol with methallyl alcohol is also achieved over npAu high methanol mole fraction in the flow reactor at atmospheric pressure at 150° C. (FIGS. 18a-b). The maximum selectivity for methyl methacrylate production is ~22% for a methanol mole fraction of 0.99; the conversion of methallyl alcohol is ~80% under these conditions (FIG. 18a).

The dependence of the reaction selectivity for methallyl alcohol ($CH_2$=$C(CH_3)CH_2OH$) reaction as a function of methanol mole fraction (FIGS. 18a-b) is similar to the allyl alcohol/methanol reaction (FIGS. 17a-b). Specifically, methyl methacrylate is only observed for methanol mole fractions above 0.92. At lower methanol mole fractions, methacrolein is the sole product detected. Methyl formate is produced for $X_{CH3OH}$ above ~0.96 and is the only product for reaction of pure methanol. These data demonstrate that, in addition to the C=C bond, the addition of a methyl group significantly affects the competition for binding sites so that a higher mole fraction of methanol is required to achieve comparable surface concentrations of the two alkoxy species. The estimated equilibrium constant for methanol and methallyl alcohol competition is ~450, which is 4.5 times greater than that for allyl alcohol (Table 3). Based on this estimated $K_{eq}$, a methanol mole fraction of 0.998 is needed to establish a 1:1 ratio of methoxy and methallyloxy species at the surface, which would be expected to maximize the cross-coupling selectivity to methyl methacrylate.

The results described herein clearly demonstrate that the selectivity for acrylate production from methanol coupling with both allyl alcohol and methylallyl alcohol are determined by the relative surface concentrations of surface intermediates on both the Au(110) surface and on the npAu catalyst under reaction conditions (Equation 1, above). This result is qualitatively similar to, but quantitatively different from, the dependence of selectivity on methanol mole fraction for methanol coupling with ethanol and 1-butanol. The relative concentrations of adsorbed alkoxy species depend on small differences in the adsorption energy of the reactive intermediates. These small differences are largely by difference in van der Waals (vdW) interactions between the alkyl group and the Au surface, which is also generally related to their corresponding gas phase acidities. This correlation can be attributed to the fact that both vdW interactions and gas phase acidities are related to the polarizabilty of the alkyl group.

The introduction of the unsaturated C=C bond in allyl alcohol and the addition of a methyl group in methylallyl alcohol clearly and substantially increase the adsorption efficacy of the respective alkoxides relative to saturated alkoxides. The equilibrium constants of 100 and 450 determined for allyloxy/methoxy and methallyloxy/methoxy, respectively, are one and two orders of magnitude higher respectively than for the unsaturated alcohols (Table 3). These equilibrium constants were derived from the flow reactor experimental results (FIG. 19). Displacement reactions performed for these reactants under UHV conditions on O/Au(110) interface are also consistent with the flow reactor results.

The gas phase acidity is also a good qualitative predictor for the apparently stronger bonding of allyloxy relative to methoxy, ethoxy or 1-butoxy, as shown in Table 3. From a bonding perspective, it is evident that the C=C bond has a major effect on the binding of the allylic alkoxides, suggesting interaction of the π system with the gold. The fact that the equilibrium constant for competitive binding of methallyloxy and allyloxy (Equation 2, below) is ~4.5 demonstrates that the methyl group also has an effect on the binding, which is indicative of vdW interactions with the surface.

$$CH_2=C(CH_3)CH_2OH\ (g) + CH_2=CHCH_2O\ (ads) \leftrightarrows CH_2=CHCH_2OH\ (g) + CH=C(CH_3)CH_2O\ (ads) \quad (2)$$

The oxidative cross-coupling of allyl and methallyl alcohols with methanol can be achieved under mild conditions over npAu surfaces without competing attack of the unsaturated C=C bond. Optimum cross-coupling selectivities are achieved when the surface concentrations of methoxy and allyloxy/methallyloxy intermediates are relatively equal, requiring methanol mole fractions above 99% due to the stabilizing effects of the C=C bond (on allyloxy) and an additional methyl group (on methallyloxy). The results further emphasize the importance of van der Waals interactions between reaction intermediates and the surface in determining the reactant concentrations for achieving the best cross-coupling conditions.

Example 6. Model Studies of the Reactions of Acrolein, Methacrolein and Methanol on Oxygen Precovered Au(110) and npAu in Ultrahigh Vacuum Model studies were conducted under UHV conditions on both the O/Au(110) and on O/npAu surfaces. Adsorbed atomic oxygen was formed on the Au(110) surface via ozone exposure (p=5×10$^{-8}$ Torr) at 300 K and via O$_2$ exposure on the activated npAu surface (p=4×10$^{-10}$ Torr) at 300 K. Reactants were dosed at 120 K so that no residual oxygen was detectable by temperature programmed desorption (m/z=32 above 500 K).

Methanol, acrolein and methacrolein each show characteristic reaction patterns with preadsorbed atomic oxygen. As discussed, methanol self-couples to form methyl formate at 250 K via adsorbed methoxy intermediate (Xu, B. et al. Agnew. Chem. Int. Ed. 2009, 48, 4206; Stowers, K. J. et al. J. Catal. 2013, 308, 131; Personick, M. L. et al. ACS Catal. 2015, 5, 4237). The reaction of acrolein with oxygen-precovered Au(110) yields, characteristically, carbon suboxide (m/z=68) at 443 K with minor amounts of acrylic acid (m/z=72) (FIG. 20a). Acrolein (m/z=56) desorbing below 300 K corresponds to unreacted aldehyde. There is some combustion to carbon dioxide (m/z=44), due to over-oxidation under the conditions employed and production of water (m/z=18) below 400 K. Methacrolein is oxidized to methacrylic acid at 300-450 K as well as CO$_2$ at 350 K (FIG. 20c). When coadsorbed at 120 K on Au(110) precovered with 0.1 ML of adsorbed O, methanol and acrolein (methacrolein) cross-couple to form methacrylate and methyl methacrylate at 280 and 320 K, respectively (FIG. 20b, d). Similar results were observed on np(Ag)Au for acrolein in ultrahigh vacuum.

Acrolein or methacrolein was first adsorbed on the 0.1 ML O/Au(110) interface at 120 K. The sample was then heated to a prescribed temperature, (below the desorption temperature of the aldehyde), cooled to 120 K and methanol dosed before ramping the temperature to perform TPRS to detect any coupling product that formed (methyl acrylate or methyl methacrylate) (FIG. 21).

For both aldehydes the amount of ester formed decreased progressively as the annealing temperature was increased up to 240 K, above which no production of the cross coupling products was detected subsequent to methanol exposure. The reduction in the amount of acrylate produced was accompanied in the same fashion by increase in the oxidation product of the aldehyde. These observations indicate that the aldehydes are simply molecularly adsorbed the O/Au(110) interface at 120 K and start reacting with the surface oxygen at ~160 K, completing reaction with the surface oxygen at 240 K. Water production is observed for oxidation of both acrolein and methacrolein on the O/Au (110) surface at 240 K (FIG. 20a, c), indicating the formation of acrylates as surface intermediates. The fact that the aldehydes do not react with the surface oxygen when dosed at 120 K, results in free adsorbed oxygen atoms on Au(110) which are available for methoxy formation upon subsequent methanol adsorption at 120 K. Furthermore, methanol cannot displace the acrylate intermediate formed from the reaction of the aldehyde with adsorbed O.

Figure 21A:
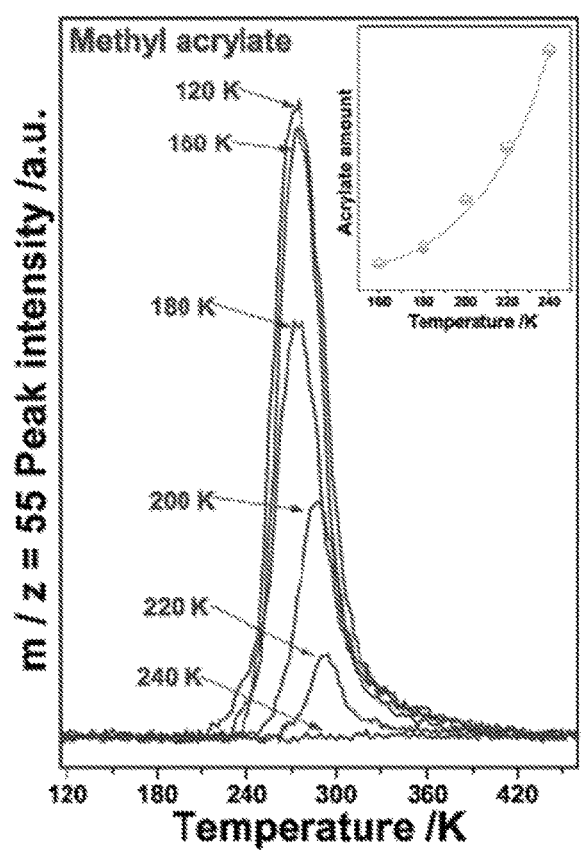
FIGS. 21a-21b shows methyl acrylate and methacrylate detected by TPRS resulting from a) adsorption of 2 ML of acrolein on 0.1 ML O/Au(110) at 120 K, then flashing of the sample to various temperatures and finally cooling down to 120 K to adsorb 2 ML of methanol, b) exact same procedure for methacrolein and methanol sequential dosing. Inset figures show the amount of the acrylate produced on the surface for each annealing. The intermediate coverage was calculated by the differences in the integrated peak areas between 120 K and the target temperature. For all experiments the sample temperature was ramped to a preset temperature at 5 K s$^{-1}$. When the target temperature was reached the heater was turned off immediately.
Figure 21B:
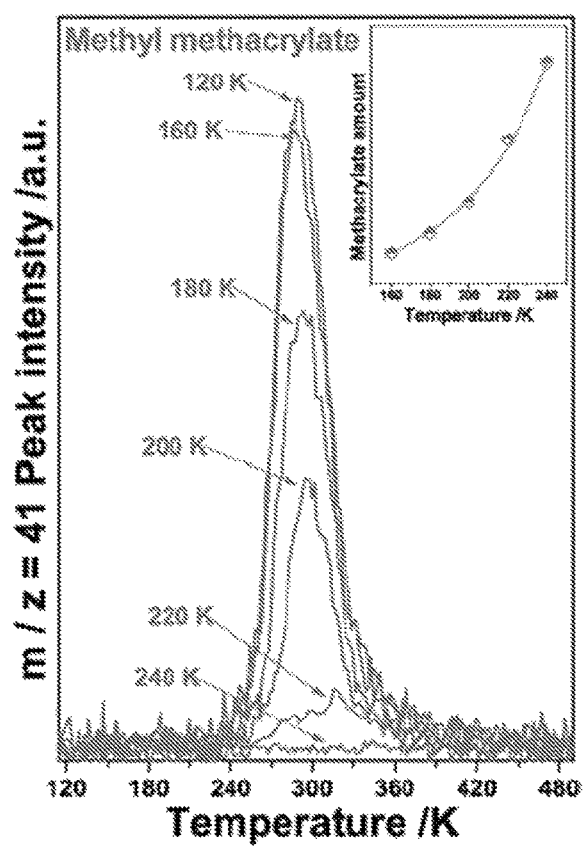

The apparent activation energy of acrolein and methacrolein reaction with the surface oxygen on Au(110), towards acrylate formation, can be calculated from the data in FIG. 21. Both aldehydes exhibit low activation energies for the formation of their respective surface intermediates of ~3 kcal/mol.

Figure 22C:
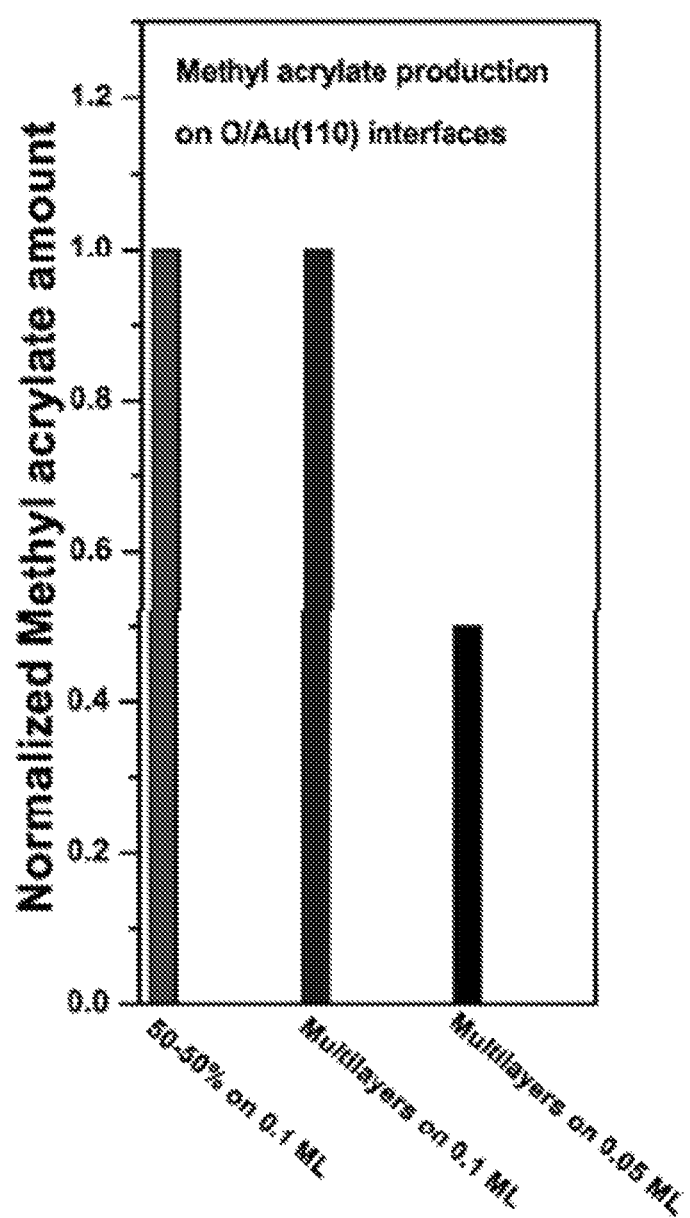

Sequential dosing of methanol-acrolein multilayers on two different O/Au(110) interfaces (0.05 ML and 0.1 ML O coverage) at 120 K, resulted in methyl acrylate production (FIG. 22a, b). Independent of the order of the dosing of the reactants on the surface, the amount of the methyl acrylate production was the same and equal to the case of 0.5 ML of methanol and 0.5 ML of acrolein (50-50%) dosed sequentially at 120 K. Reduction of the initial oxygen coverage from 0.1 ML to 0.05 ML cuts the amount of methyl acrylate production in half (FIG. 22c).

The fact that the order of dosing of multilayers of the reactants at 120 K does not change the amount of acrylate formed, indicates that at this low temperature, methanol preferentially reacts with the surface oxygen. Methyl acrylate results subsequently from the coupling of a methoxy with coadsorbed molecular acrolein. Finally, the fact that the amount of methyl acrylate reduces in proportion to the amount of preadsorbed oxygen is further indication that the oxygen is removed preferentially by methanol to form methoxy which reacts stoichiomentrically with the molecularly adsorbed acrolein.

The steady state behavior the catalyst can be understood from the model studies on Au(110). At 150° C. the aldehyde and methanol compete for adsorbed O, activated by the npAu. The fact that the adsorbed acrylate is more stable than the adsorbed methoxy leads to its buildup on the surface, and it poisons a large fraction of the active sites. However, since its rate of decomposition is finite at 150° C., sites turn over at which adsorbed O, and, in turn, methoxy establish a low steady state concentration. Thus, the acrylates form via coupling with a low conversion.

Figure 23:
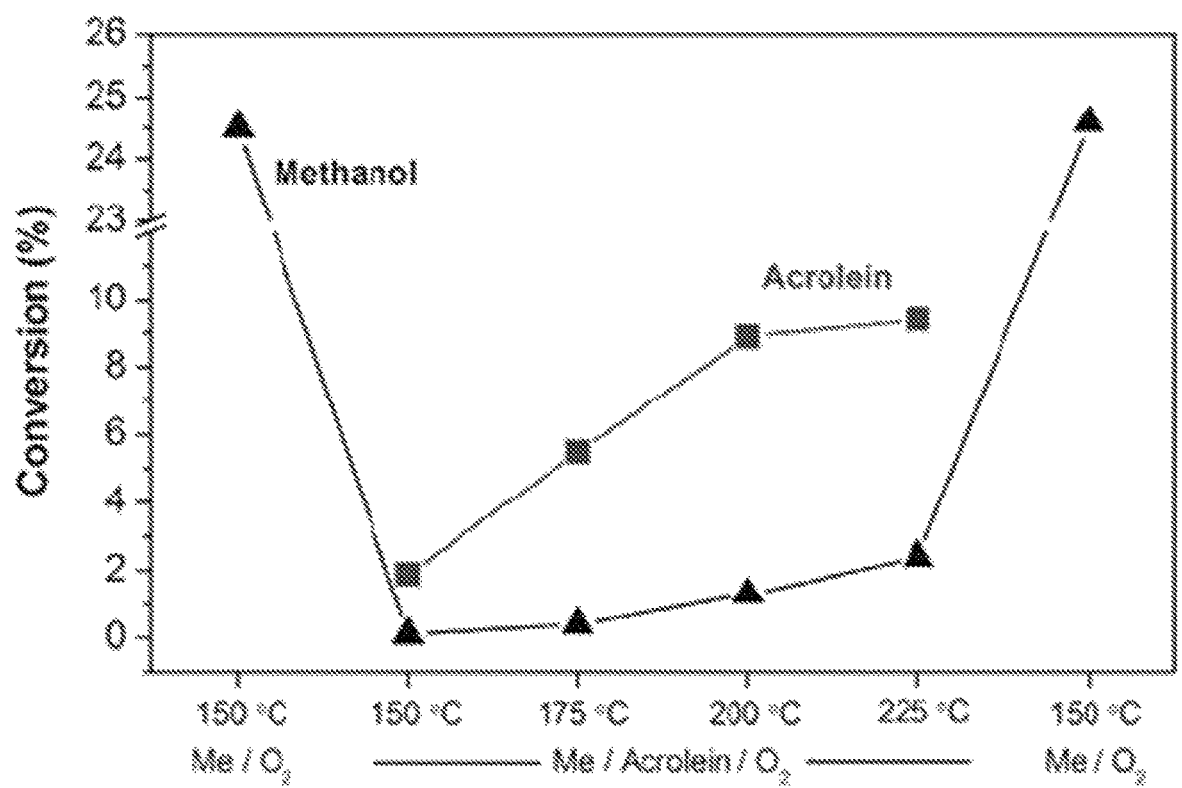
FIG. 23 shows the effect of temperature on the methanol-acrolein cross-coupling activity (conversion) in flow reactor. Flow conditions during cross-coupling: $X_{MeOH}$=0.91, 20% $O_2$, 50 mL/min.
Figure 24:
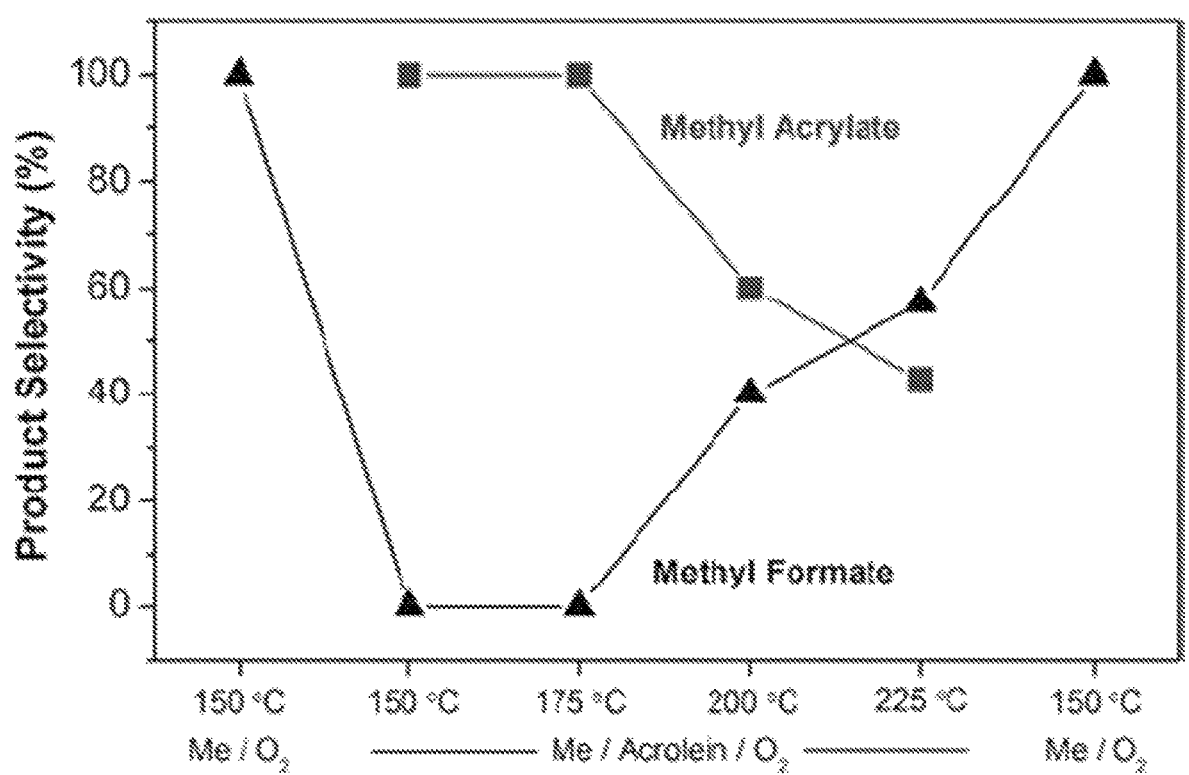
FIG. 24 shows the effect of temperature on the methanol-acrolein cross-coupling activity (selectivity) in flow reactor. Flow conditions during cross-coupling: $X_{MeOH}$=0.91, 20% $O_2$, 50 mL/min.

The reaction was therefore examined in the reactor over an extended range of temperatures between 150 and 225° C. (FIGS. 23 and 24). Increasing the reactor temperature increases the rate of decomposition of the adsorbed acrylate and thereby increases the site availability and turnover towards cross coupling due to the preferential reactivity of methanol with adsorbed O. At the higher temperatures studied in the reactor methyl formate begins to dominate the product; no attempt was made to optimize the reactant composition for enhancing selectivity at these temperatures. In the temperature range where the adsorbed acrylate is expected to decompose a higher rate the conversion increases from 3% to 10%, a significant effect. That this loss in selectivity that is not due to catalyst degradation (coarsening of the npAu, for example) was demonstrated from the preservation of activity for methanol self-coupling before and after temperature cycling. The yield of methyl acrylate maximizes near 225° C.

Figure 25A:
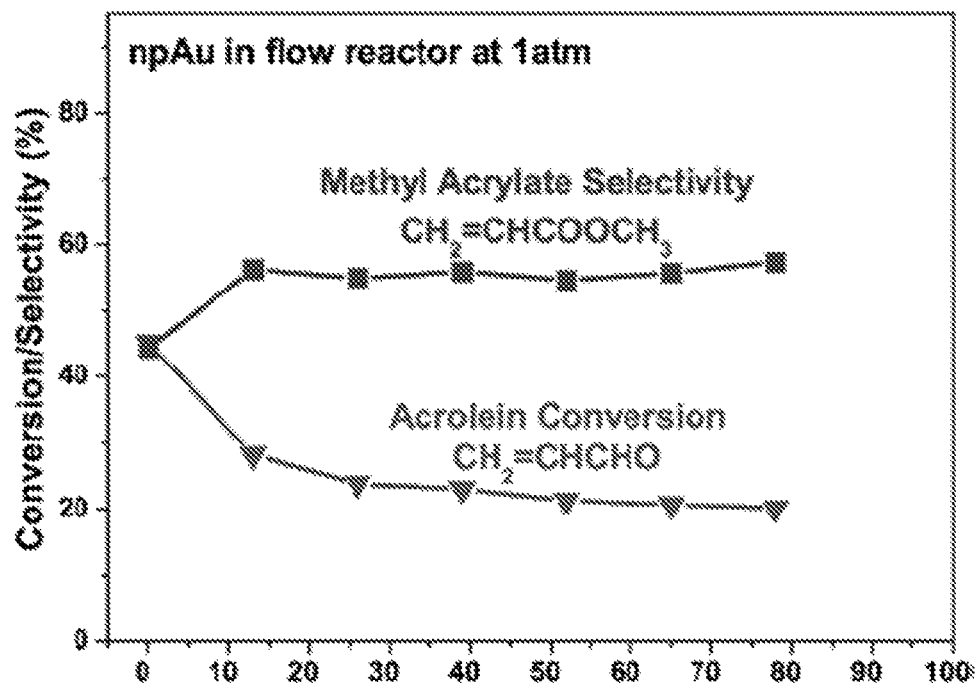
FIGS. 25a-25b shows the deactivation of npAu during the initial introduction of aldehydes during cross-coupling experiments. Reaction conditions: (a) XMeOH=0.97, 5% MeOH/R═O(Total)-20% $O_2$, 50 mL/min, 150° C., (b) XMeOH=0.98, 5% MeOH/R═O (Total)-20% $O_2$, 50 mL/min, 150° C.
Figure 25B:
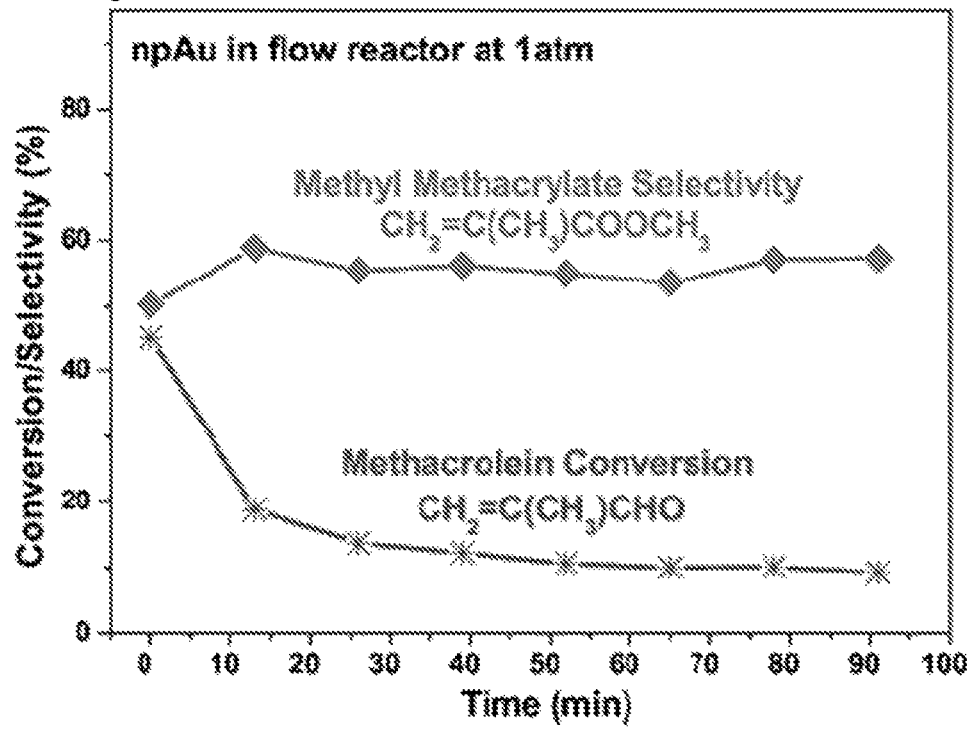

The formation of the strongly bound acrylates also progressively deactivates the catalyst for the cross-coupling reactions (FIG. 25a, b). The extent of npAu poisoning by surface acrylates on npAu in the flow reactor was evident following the introduction of acrolein or methacrolein to a methanol-oxygen reaction mixture at 150° C. At the conditions used (methanol mole fractions of 0.97 to 0.98), the aldehyde conversion dropped immediately from ~46% to 20% for acrolein and to 9% for methacrolein over the following 80-90 min.

Figure 26:
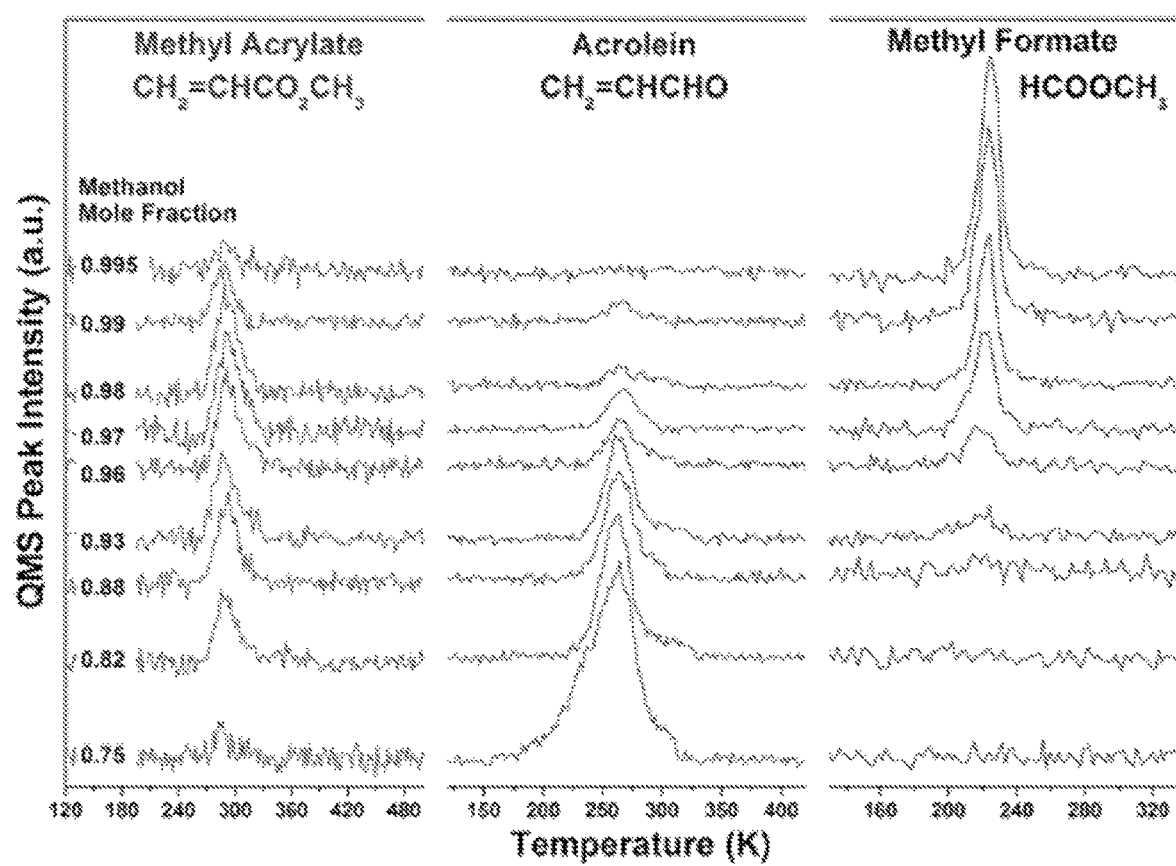
FIG. 26 shows methanol and allyl alcohol reaction on O-activated Au(110) yielding methyl acrylate, acrolein, and methyl formate. Atomic oxygen was dosed at 300 K to form 0.1 ML adsorbed via ozone exposure, followed by dosing of alcohols to excess, at 130 K. Methanol was dosed prior to allyl alcohol, and overlapping mass fragments have been subtracted for clarity. The parent ions for methyl formate (m/z 60) and acrolein (m/z 56), and the most intense ion for methyl acrylate (m/z 55) are detected. The heating rate was 5 K/s. Under these conditions, no residual oxygen was detected in the temperature-programmed desorption spectra: i.e., no peaks were observed for m/z 32 above 500 K, where recombination of $O_2$ occurs.

Example 7. Studies of the Reactions of Unsaturated Alcohols with Methanol on Oxygen-Precovered Au(110) and npAu Under Ultrahigh Vacuum Methanol and allyl alcohol form methyl acrylate (m/z 55) in temperature-programmed reaction on O-activated Au(110) but only at high relative methanol doses, above methanol mole fractions of 0.75 (FIG. 26). The other products formed are methyl formate at 220 K, derived from coupling of two methanol molecules, and acrolein at ~260 K, derived from allyl alcohol. No reaction occurs on clean Au(110)—only molecular desorption of the parent alcohols is detected.

The product selectivity is strongly dependent on the methanol mole fraction ($X_{CH3OH}$). Methyl formate is the dominant product at very high methanol mole fractions (>0.97), shown in FIG. 26. As the relative dose of methanol is reduced, the selectivity for cross-coupling to methyl acrylate increases, reaching a maximum at a methanol mole fraction of 0.97. When the methanol mole fraction is reduced further, acrolein (m/z 56) becomes the dominant product. This catalytic process is qualitatively very similar to that reported for methanol coupling with ethanol and 1-butanol on Au(111) (Xu, B. et al. *J. Am. Chem. Soc.* 2010, 132, 16571). Namely, the product selectivity (which reflects the relative concentrations of the two alkoxides on the surface) is not the same as the ratio of concentrations of the reactant alcohols.

Figure 27:
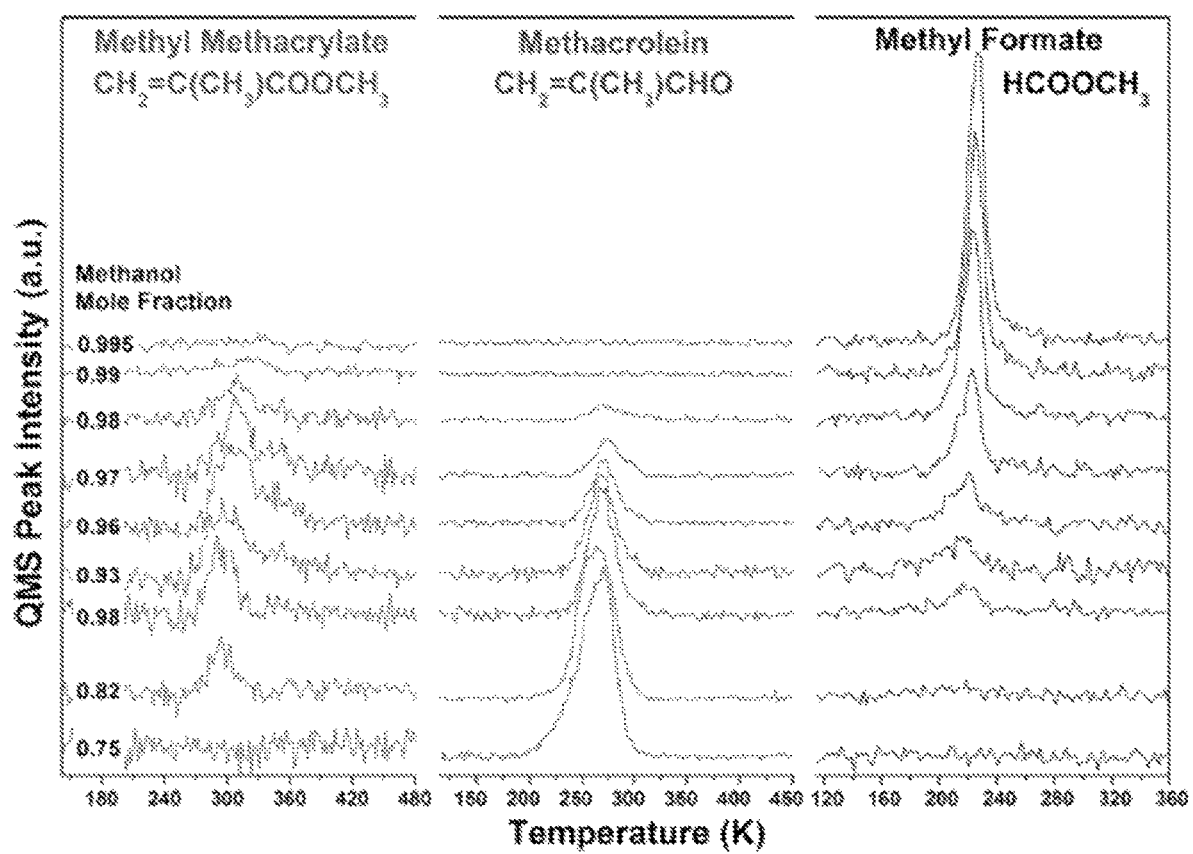
FIG. 27 shows the oxidative coupling of methallyl alcohol with methanol on Au(110) surface. A 0.1 ML amount of atomic oxygen was dosed at 300 K via ozone exposure, followed by the dosing of alcohols at 130 K. Methanol was dosed prior to methallyl alcohol, and overlapping mass fragments have been subtracted for clarity. The parent ions for methyl formate (m/z 60), methacrolein (m/z 70), and the most intense ion for methyl methacrylate (m/z 41) are detected. The heating rate was 5 K/s. Under these conditions, no residual oxygen was detected in the temperature-programmed desorption spectra: i.e., no peaks were observed for m/z 32 above 500 K, where recombination of $O_2$ occurs.

Coupling of methallyl alcohol with methanol to yield methyl methacrylate was also achieved on oxygen-precovered Au(110) at high methanol mole fractions (FIG. 27). Again, the selectivity depends strongly on the methanol mole fraction. At very high $CH_3OH$ mole fraction, methyl formate is the predominant product. Methyl methacrylate is formed in a narrow window of composition (0.82≤$X_{CH3OH}$≤0.99). Methyl methacrylate production reaches a maximum at a methanol mole fraction of 0.97 and is produced at the expense of methyl formate. At methanol mole fractions below 0.75, methacrolein is the sole product and is evolved at ~260 K. No combustion was observed, nor were any higher molecular weight products detected in a search between 2 and 120 amu. Reaction of pure methallyl alcohol on O/Au(110) also solely yields methacrolein (m/z 70) between 240 and 310 K with no combustion or cross-coupling products, demonstrating that this product is characteristic of adsorbed methallyloxy. The relatively high methanol mole fraction needed for the production of methyl methacrylate suggests that methallyloxy binding dominates methoxy on the Au(110) surface and that its binding is similar to that of allyloxy (Wang, L.-C. et al. *J. Catal.* 2015, 329, 78; Xu, B. et al. *J. Am. Chem. Soc.* 2010, 132, 16571). Products indicative of oxidation of the C=C double bond were not observed.

Example 8. Capacity of the npAu Catalyst in $O_2$ Dissociation

Figure 29A:
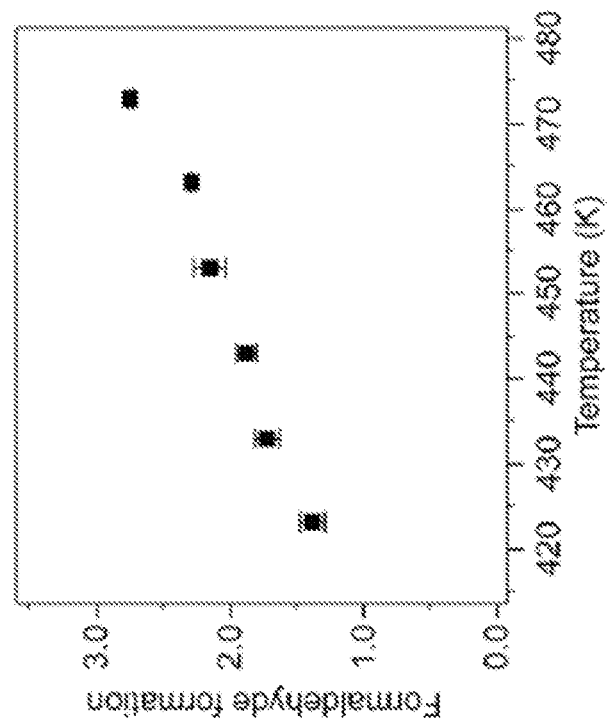
FIGS. 29a-29b shows (a) The fractional coverage of adsorbed oxygen atoms on the npAu catalyst versus the $O_2$ dose from sequential pulses of $O_2$ at 423 K. (b) Formaldehyde formation during the titration of active oxygen from $O_2$ dissociation on the npAu catalyst at different temperatures (single pulse of $O_2$ followed by titration with 100 pulses of $CH_3OH/Ar$).

First, the activation of $O_2$ on the npAu catalyst by exposing the catalyst at 423 K sequentially to 100 $O_2$ pulses and 100 $CH_3OH$/Ar pulses was examined. The oxygen uptake from $O_2$ exposure, determined either by the $O_2$ response pulse exiting the reactor or by the total amount of formaldehyde formed during the subsequent methanol titration, increases rapidly as the $O_2$ dosage increases and then approaches saturation (FIG. 29a).

Based on the amount of npAu (27 mg), the BET surface area (2 m$^2$ g$^{-1}$) after activation, and the amount of formaldehyde formed at the saturation point (3.1×10$^{15}$ molecules), the surface concentration of adsorbed O at saturation coverage resulting from the $O_2$ pulsing was calculated to be 6.2×10$^{16}$ O atoms per m$^2$ or 4.4×10$^{-3}$ ML, assuming a surface atomic density of 1.4×10$^{19}$ atoms per m$^2$ for the Au(111) surface. It is possible that O could spill over onto the surface (the saturation density on gold being near 1.0 M) (Kim, J. et al. *Surf. Sci.* 2006, 600, 4622), but this apparently does not occur at these temperatures.

From the points in the initial linear portion of the uptake vs. exposure curve (FIG. 29a) the initial dissociative sticking probability of $O_2$ at the lowest initial oxygen coverage on the activated npAu catalyst at 423 K was computed to be ~1×10$^{-7}$ at 423 K. This value is significantly lower than that on single-crystal Ag surfaces (Bowker, M. et al. *Surf. Sci.* 1980, 92, 528; Campbell, C. T. *Surf. Sci.* 1985, 157, 43) and on Ag powder (Bowker, M. et al. *J. Chem. Soc., Faraday Trans.* 1989, 85, 2635) or even on supported Ag catalysts (Dean, M. et al. *Appl. Surf. Sci.* 1988, 35, 27).

Figure 29B:
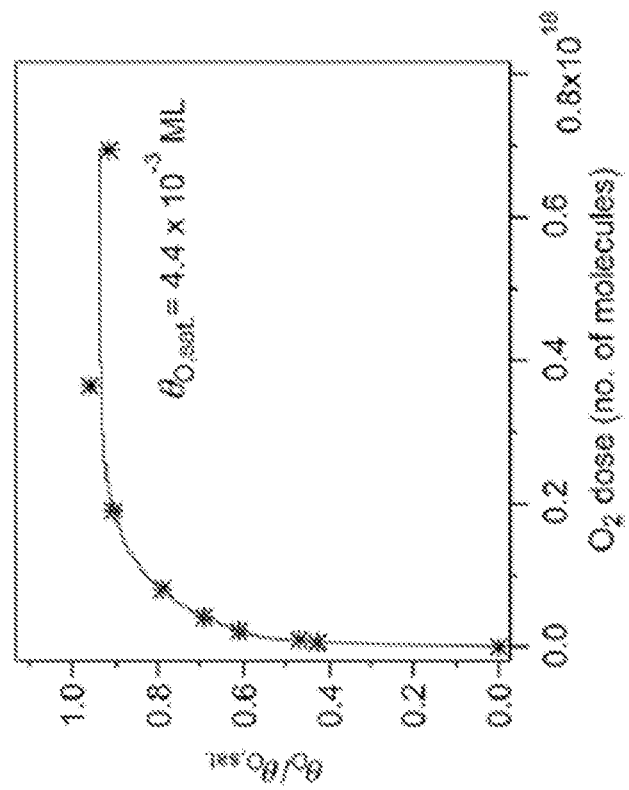

By methanol titration following $O_2$ exposure at different temperatures (473 K to 423 K), the apparent activation energy (Ea) for $O_2$ dissociation on the npAu catalyst was determined to be 5.0±0.4 kcal mol$^{-1}$ (FIG. 29b). This result is comparable to that reported on Ag single-crystal surfaces (Campbell, C. T. *Surf. Sci.* 1985, 157, 43) but significantly below that estimated for single-crystal Au surfaces (Kim, J. et al. *Surf. Sci.* 2006, 600, 4622; Gottfried, J. M. et al. *Surf. Sci.* 2003, 525, 184; Legare, P. et al. *Surf. Sci.* 1980, 91, 175). Experimentally, neither stepped single crystals nor polycrystalline Au surfaces dissociate molecular oxygen even at a high temperature or under high-pressure conditions (Sault, A. G. et al. *Surf. Sci.* 1986, 169, 347; Kim, J. et al. *Surf. Sci.* 2006, 600, 4622; Legare, P. et al. *Surf. Sci.* 1980, 91, 175).

Example 9. Stability of $O_a$ from $O_2$ Dissociation

Figure 28:
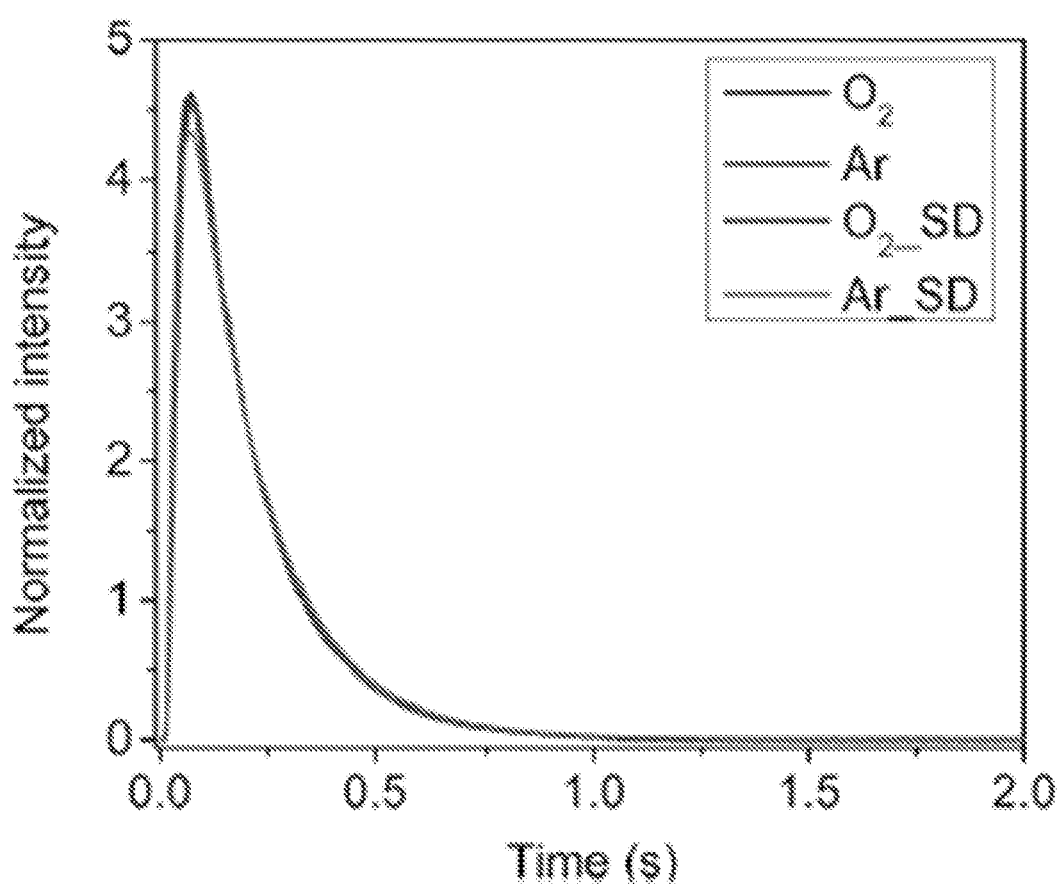
FIG. 28 shows the experimental and simulated standard diffusion (SD) pulse response curves of $O_2$ and Ar on the npAu catalyst at 423 K.
Figure 30:
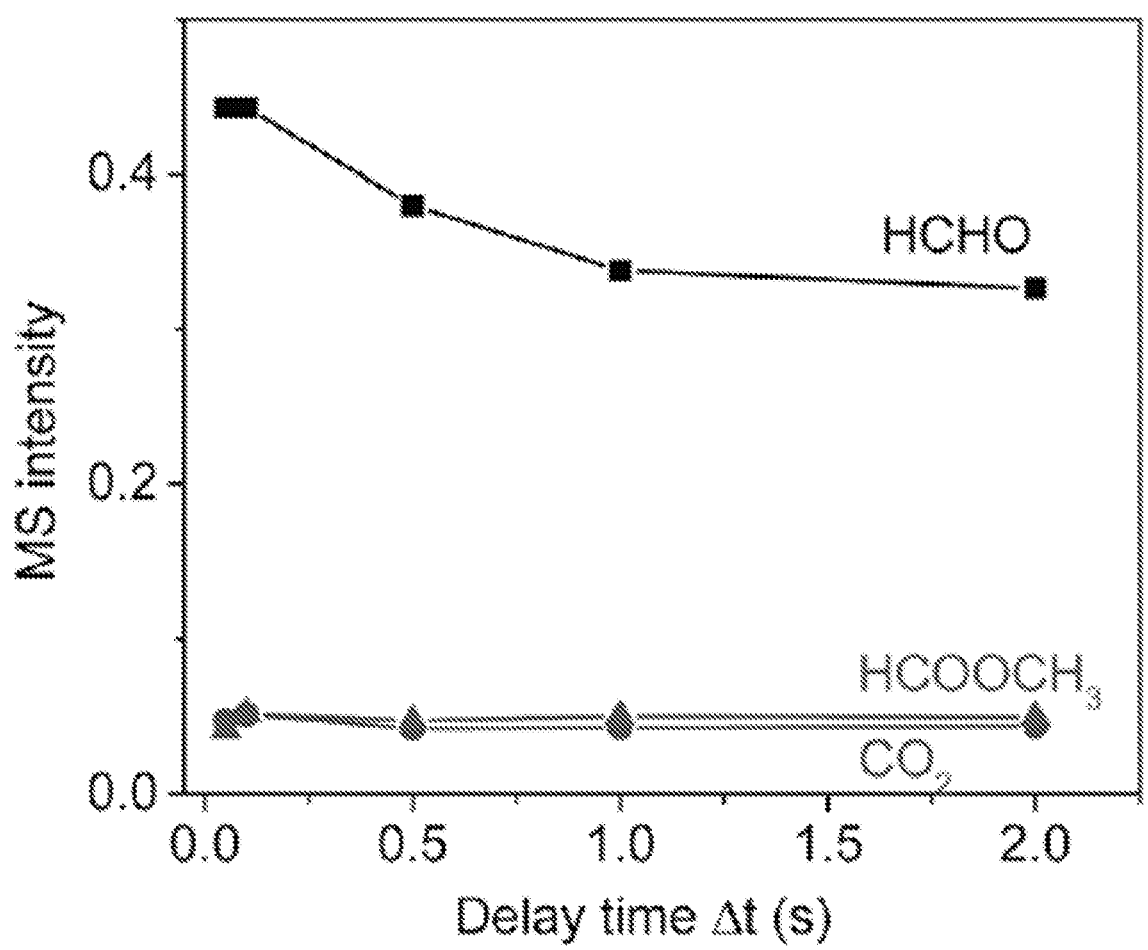
FIG. 30 shows the formation of various products including formaldehyde, methyl formate, and $CO_2$ as a function of the delay time between 1 pulse of $CH_3OH/Ar$ and 1 pulse of $O_2$.

By varying the delay time between the $O_2$ pulse and the subsequent methanol pulse, we further investigated the stability of the active oxygen species formed from $O_2$ dissociation on the npAu catalyst. The results showed that the amount of formaldehyde formation decreased rapidly with the delay time below 0.5 s and then kept almost constant as the delay time was further extended up to 2 s (FIG. 30). The higher formaldehyde formation when the delay time is below 0.5 s may be explained by the enhanced total $O_2$ uptake due to the overlap between the $O_2$ and methanol pulses (see FIG. 28). Since methanol can readily react with adsorbed O, it is reasonable to deduce that in the presence of excess methanol, the active sites (adsorbed O) can be rapidly regenerated, resulting in a higher total $O_2$ uptake at a shorter delay time. With an extended delay time between the $O_2$ and methanol pulses, more $O_2$ will leave the catalyst bed before the methanol pulse arrives at the catalyst surface, leading to less $O_2$ dissociation and thus decreasing formaldehyde formation.

Note that adsorbed atomic O is quite stable on both Ag and Au single crystal surfaces, desorbing by atom recombination near 550 K (Sault, A. G. et al. *Surf. Sci.* 1986, 169, 347; Campbell, C. T. *Surf. Sci.* 1985, 157, 43; Gottfried, J. M. et al. *Surf. Sci.* 2003, 525, 184). It is possible, however, that with increased time between pulses the adsorbed O could change reactivity by conversion to another binding state. Since there was little variation in the amount of various products at a delay time longer than 0.5 s (FIG. 30), it appears that the active oxygen species from $O_2$ dissociation on the npAu surface at 423 K does not undergo a transformation into another form with different reactivity.

Example 10. Reactivity of Active Adsorbed O with CO and Methanol

Figures 31A, 31B:
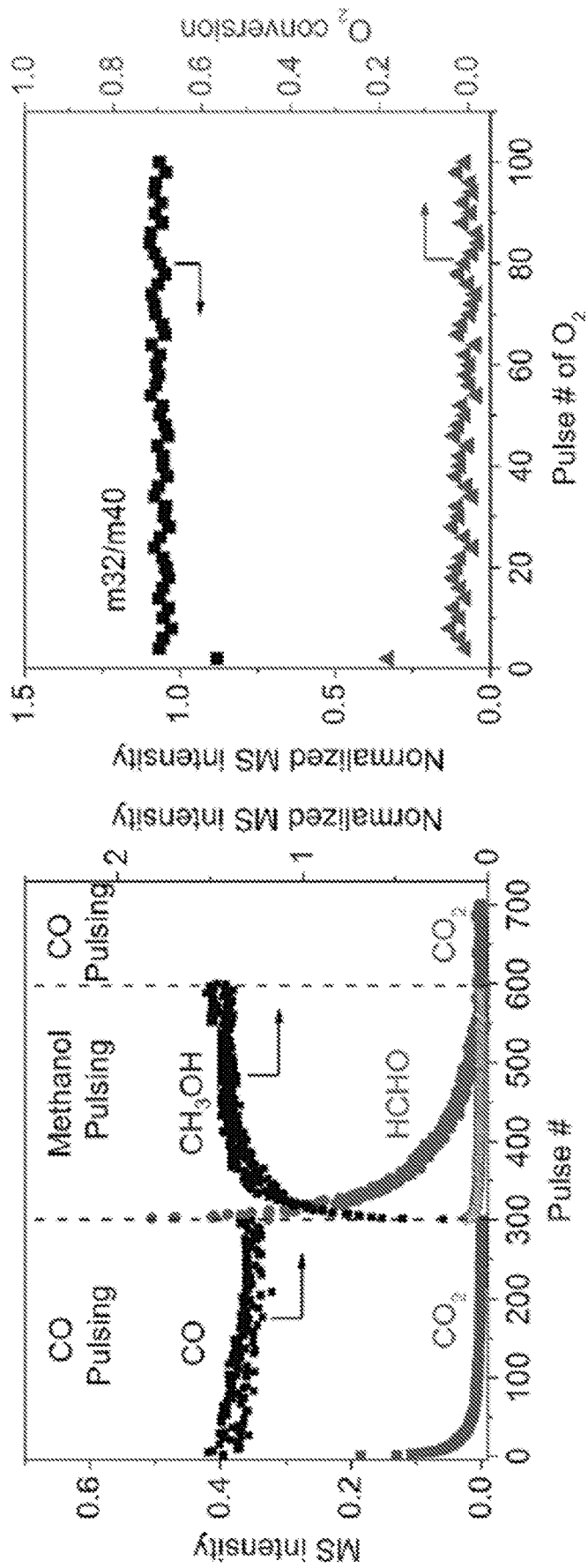
FIGS. 31a-31b shows (a) Sequential pulsing of CO and methanol over npAu after 100 pulses of $O_2$. (b) Normalized $O_2$ pulse intensity and the corresponding $O_2$ conversion in each pulse during $O_2$ pulsing after exposure to CO pulses.

To determine the reactivity of CO and methanol with the active adsorbed oxygen species, sequential pulsing of $O_2$ and CO/CH$_3$OH was conducted. Following an initial 100 pulses of O$_2$, the introduction of CO pulses resulted in the formation of only a very small amount of CO$_2$ at the beginning of the pulse cycle (FIG. 31a), but there was no measurable consumption of CO in parallel with the CO$_2$ formation. In addition, negligible O$_2$ uptake was detected when O$_2$ was re-introduced after CO pulsing FIG. 31b). These results clearly indicate that the CO$_2$ formation was not from the reaction of CO with the active adsorbed oxygen. We attribute the CO$_2$ to displacement from other regions of the reactor. When methanol is introduced after the CO pulses, however, initially almost all the methanol is converted with concomitant formation of formaldehyde, and the reaction abates after approximately 100 methanol pulses (FIG. 31a).

Figure 32B:
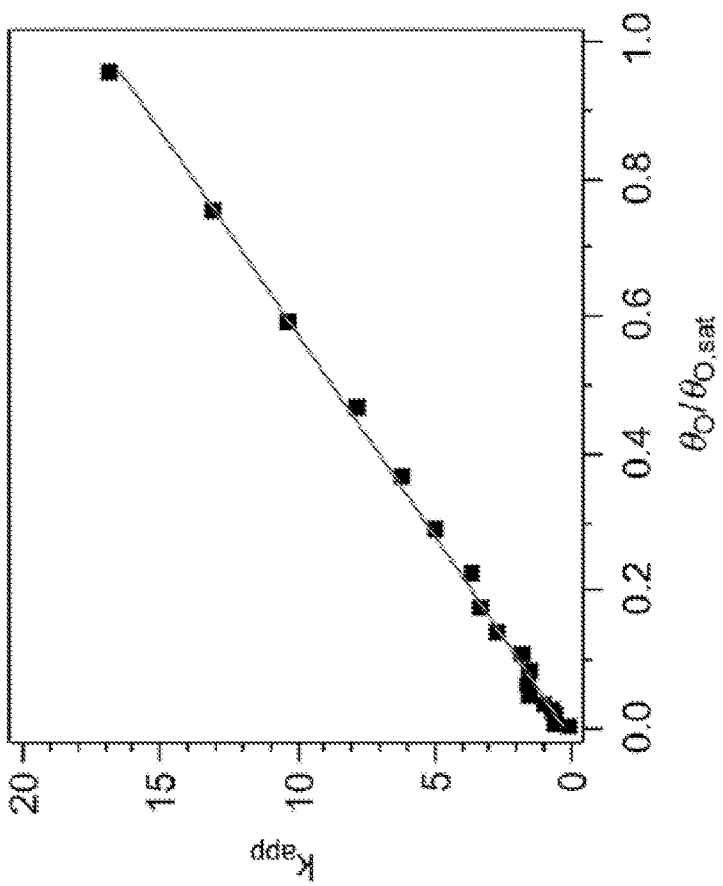
FIGS. 32a-32b shows (a) Formaldehyde formation during the pulse reaction of methanol with $O_2$ on the activated npAu catalyst at 423 K. (b) The apparent rate constant as a function of the fractional O coverage during titration after simultaneous pulsing of $O_2$ and $CH_3OH$ at 423 K.
Figure 32A:
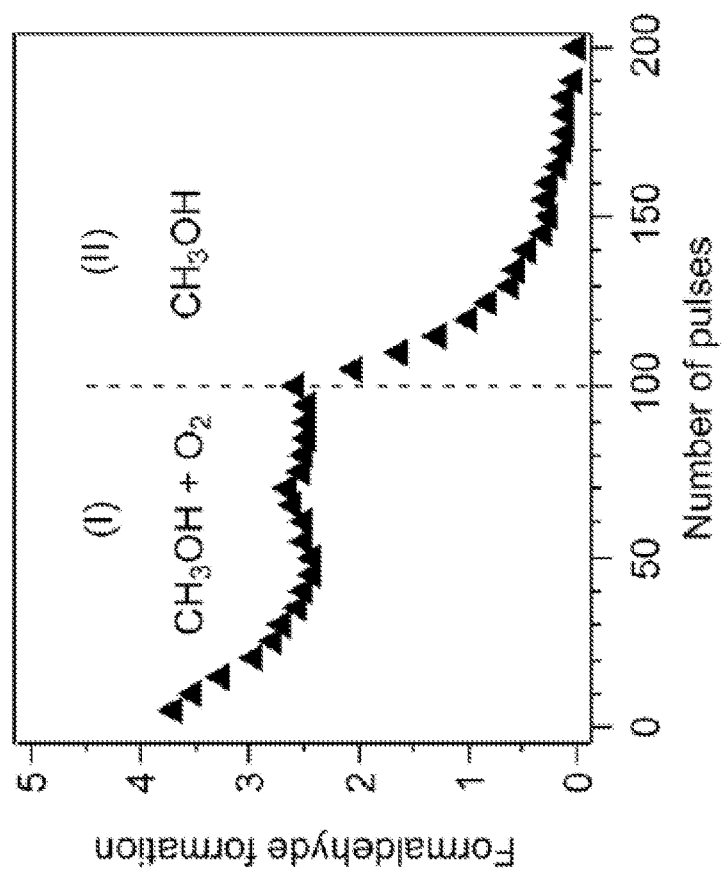

It is clear that methanol can be catalytically activated on the npAu catalyst when pulsed simultaneously with O$_2$ (FIG. 32a), producing formaldehyde as the predominant product under the pulse conditions. Surprisingly, when O$_2$ pulses were interrupted at the steady state, there was still a notable amount of formaldehyde formation, which, nevertheless, underwent an exponential decay with continuous methanol pulses. This observation indicates that there is a certain amount of oxygen species ($\sim 3 \times 10^{-3}$ ML) on the catalyst surface under the steady-state methanol oxidation reaction in the TAP reactor, which might also be the case for the reaction in the flow reactor under steady state conditions.

Figure 33:
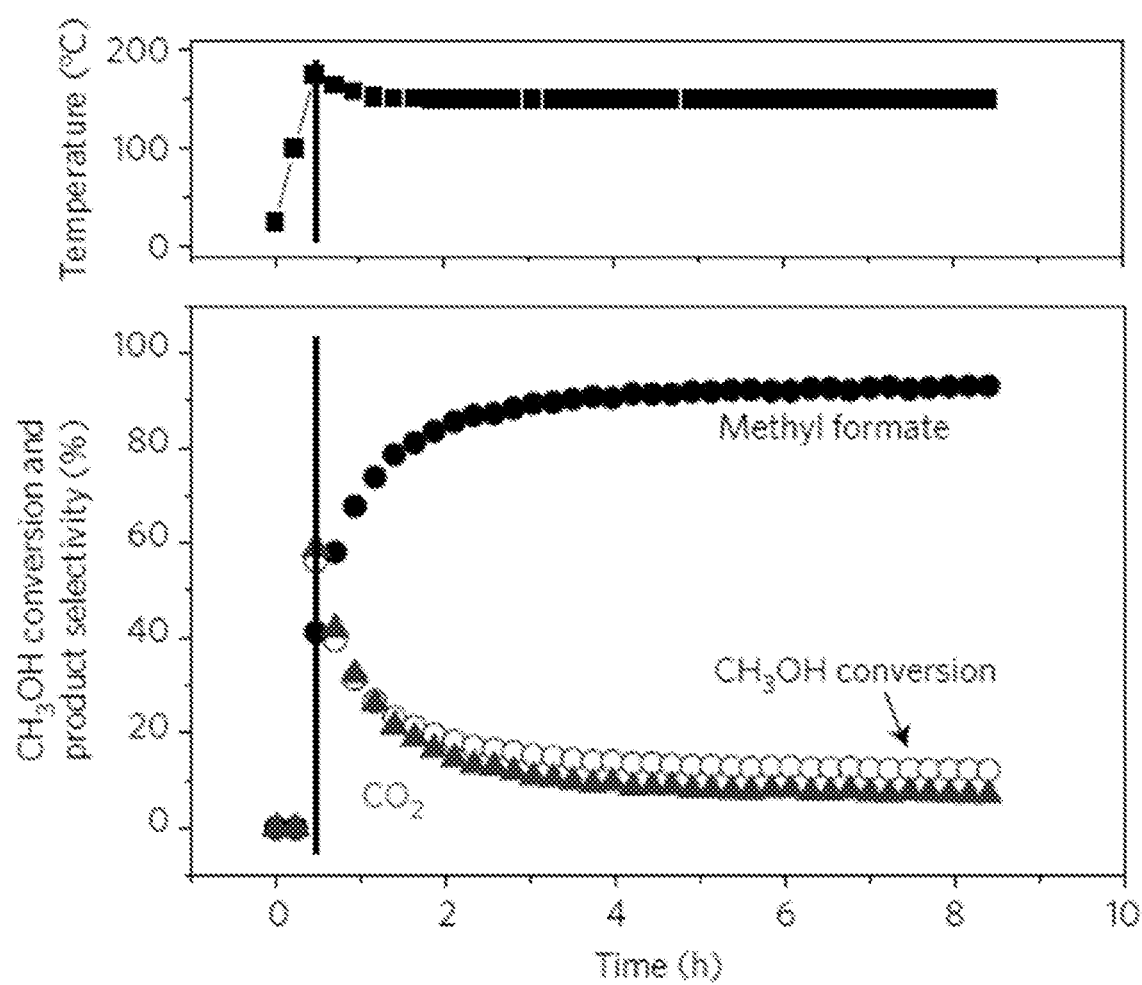
FIG. 33 shows the activation of npAu for selective methanol oxidation. Final activation of ozone-treated npAu occurs by flowing the methanol/$O_2$ reaction mixture over the catalyst while the temperature is ramped to the operating temperature of 150° C. During activation, combustion first predominates followed by a switch to selective formation of methyl formate with nearly 100% selectivity. The solid line indicates the point at which a temperature of 150° C. is reached, and the corresponding onset of reaction. The activity for selective production of methyl formate remains stable for at least several weeks.

Example 11. Activation of npAu for Selective Methanol Oxidation, Pulsed Experiments Over Ozone-Treated npAu, E-TEM Analysis of npAu after Ozone Treatment, E-TEM Analysis of npAu During CO and CH$_3$OH Exposure, AP-XPS Analysis of nAu, and Changes in the Relative Surface Concentrations of Ag, O and Au Exposure of ozone-treated npAu to a reactant stream of methanol (6.5%) and oxygen (20%) under catalytic oxidation conditions results in the transient production of CO$_2$ (combustion) before selective coupling to methyl formate commences (FIG. 33). The initial reaction in the flow reactor is the near-complete combustion of methanol to CO$_2$ as the temperature approaches 150° C. The onset of CO$_2$ is sudden and accompanied by a release of heat, causing the temperature to overshoot, thus suggesting an autocatalytic process.

After this initial combustion phase, methyl formate becomes the dominant product, eventually reaching >95% selectivity. The activity and selectivity are sustained for a long period—up to several weeks (Personick, M. L. et al. ACS Catal. 2015, 5, 4237). Furthermore, the three different forms of nanoporous Au used—ingots, thin foils, and hollow shells—all exhibit the same activation behaviour and catalytic activity (Personick, M. L. et al. ACS Catal. 2015, 5, 4237). The correspondence in catalytic behaviour demonstrates that the catalytic behaviour is dictated by the nano- and atomic-scale behaviour of the material and not the larger-scale architecture.

Figure 34A:
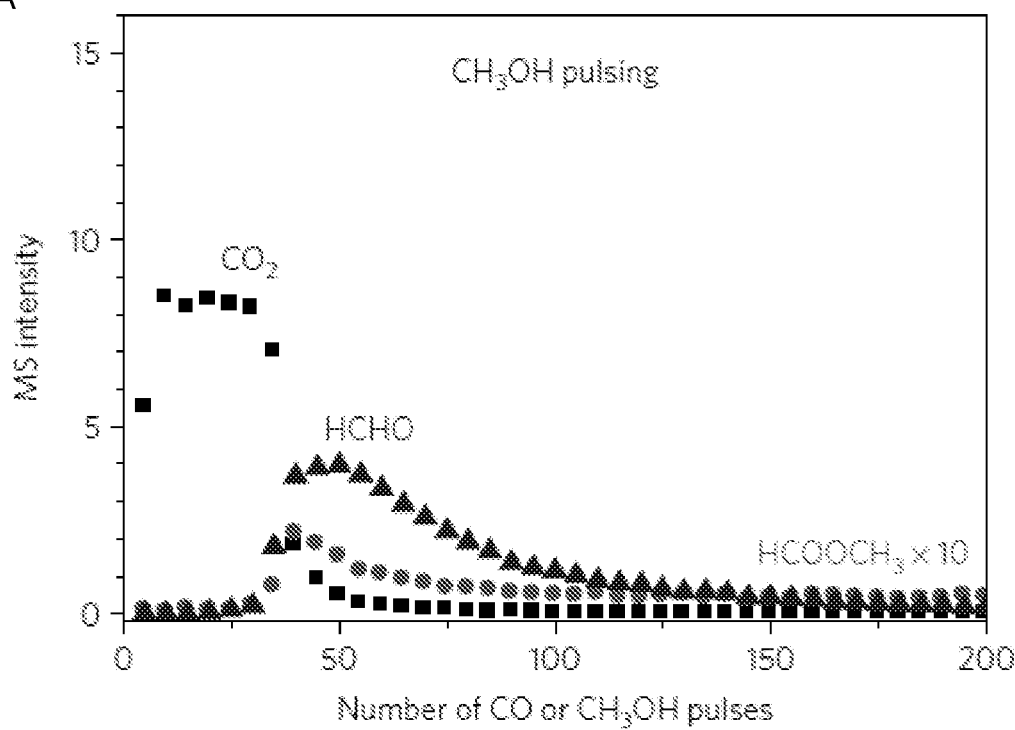
FIGS. 34a-34d shows the pulsed experiments over ozone-treated npAu. Transient (pulsed) experiments over $O_3$-treated npAu at 150° C. demonstrate that there are two chemically distinct oxygen species present on the surface: one responsible for combustion to $CO_2$ and the other for selective $CH_3OH$ oxidation to HCHO and $HCOOCH_3$. a, During $CH_3OH$ pulsing over $O_3$-treated npAu, complete combustion to $CO_2$ is observed initially; after ~25 pulses, combustion rapidly diminishes and selective $CH_3OH$ oxidation to formaldehyde is observed; the reaction ceases after ~200 pulses. b, Non-selective oxygen species can be removed by titration of highly reactive oxygen on $O_3$-treated npAu by exposure to 75 pulses of CO; $CH_3OH$ pulsing thereafter yields only selective oxidation products. c,d, Titration of surface oxygen on $O_3$-treated npAu by simultaneously pulsing methanol and CO onto $O_3$-treated npAu yields an identical pattern of reactivity—initial reaction of both CO and $CH_3OH$ to $CO_2$, followed by reaction of only $CH_3OH$ to selective oxidation products (the pulse sizes of CO and $CH_3OH$ are reduced by 50% relative to a and b to keep total reactant per pulse constant).

Combustion of methanol is also initially predominant when the ozone-treated npAu catalyst is exposed to very short pulses (<1 ms) of either methanol alone or a methanol-CO mixture (FIG. 34a, c). The rapid transition from CO$_2$ to selective oxidation indicates that there are two types of oxygen species on the surface—one responsible for combustion and the other for partial oxidation. Due to extremely short contact times in the pulse reactor, the dominant selective oxidation product is formaldehyde, rather than methyl formate. In the flow reactor, the same catalyst yielded methyl formate with high selectivity. It is well known that the first step in the catalytic cycle for methanol self-coupling is activation of methanol to formaldehyde (Xu, B. et al. Angew. Chem. Int. Ed. 2009, 48, 4206; Xu, B. et al. Chem. Sci. 2010, 1, 310); the transient experiments probe the initial step in the reaction pathway that governs the steady-state reaction. The difference in product selectivity in the titration with methanol pulses and in steady flow is related to the large difference in contact times ($10^{-4}$ s versus $10^{-1}$ s, respectively) with the catalyst and will be addressed in a separate paper (Wang, L.-C. et al. J. Catal. 2016, 334, 778).

Figure 34B:
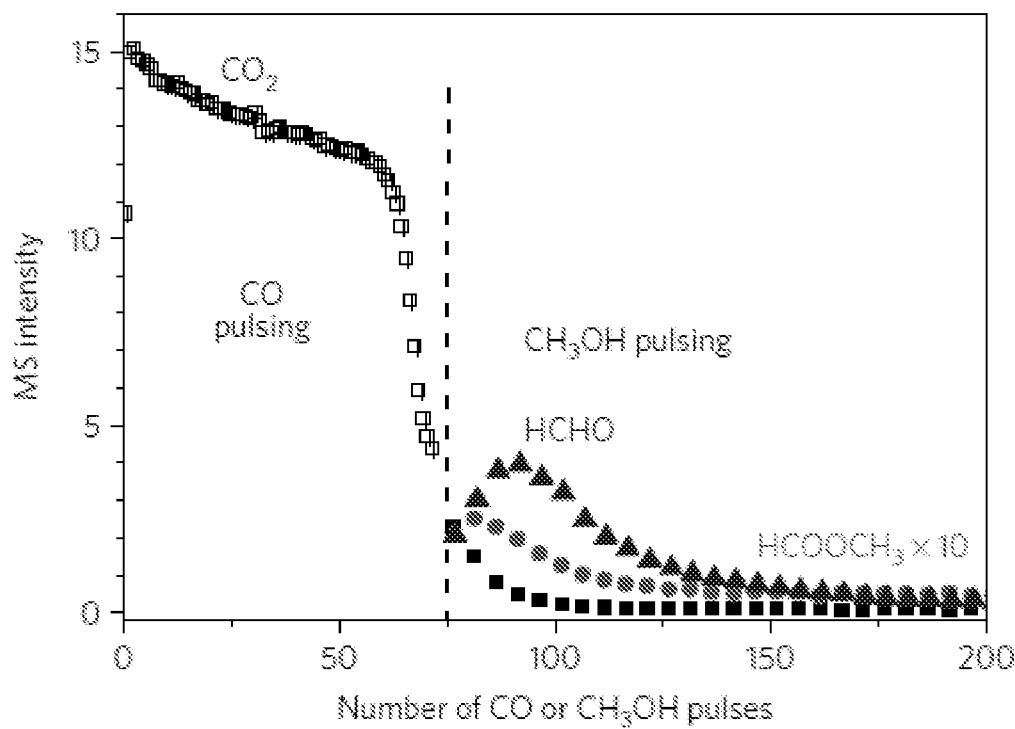

In a separate experiment, the surface oxygen resulting from O$_3$-treatment of the npAu surface was first titrated with 100 pulses of CO to remove the surface O responsible for combustion. Exposure to methanol pulses then directly yields partial oxidation products and not the initial methanol combustion (indicated by the dashed line in FIG. 34b). This result indicates that the chemical behaviour of the adsorbed O is not sensitive to the method of reduction of the more reactive oxygen that promotes combustion. In addition, a pause during the continuous pulsing of either CO or CH$_3$OH has minimal effect on the evolution of the different products as the pulses are resumed, indicating that the different states of surface oxygen from O$_3$ treatment are not inter-convertible.

Figure 34C:
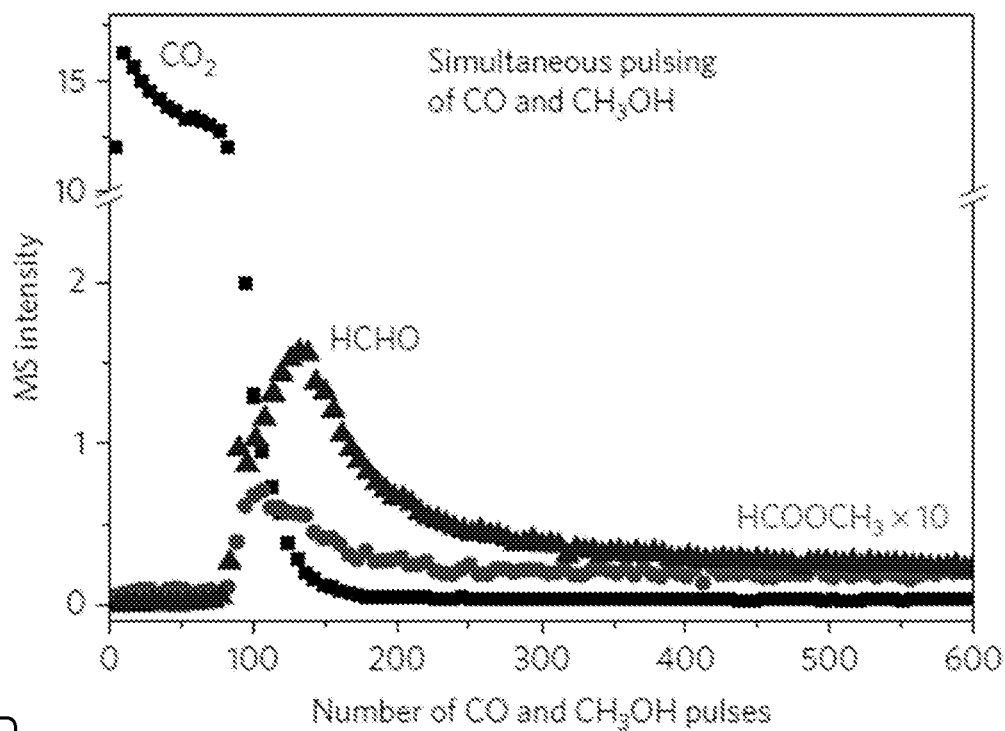
Figure 34D:
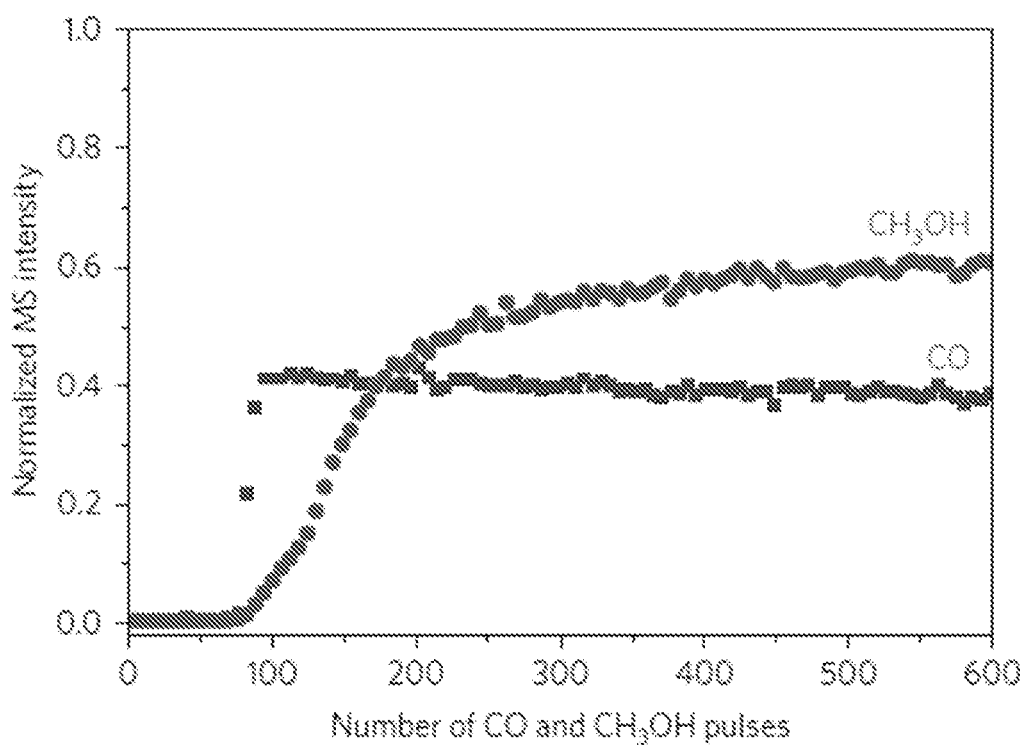
Figure 35C:
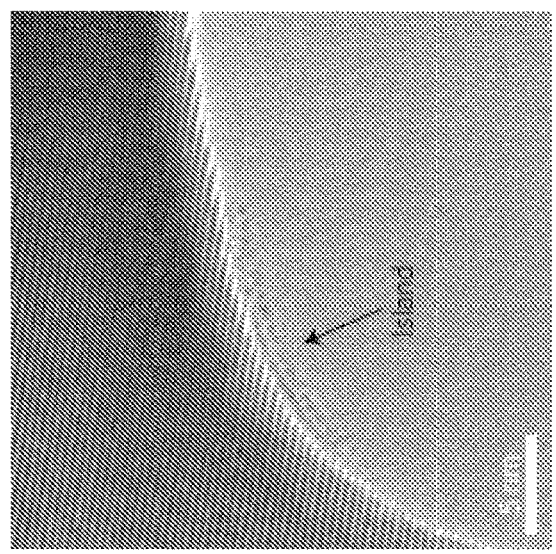
FIGS. 35a-35f shows the E-TEM analysis of npAu after ozone treatment. In situ aberration-corrected TEM images demonstrate that npAu is oxidized by $O_3$ treatment in a flow reactor at 150° C. for 1 h. a, Low-magnification image of the material showing the pore and ligament structure. b, High-resolution image of a representative spot on the material showing the resolved lattice of the ligaments and a layer of amorphous oxide after $O_3$ treatment. c, In some areas, crystalline islands are visible on the npAu surface in the high-magnification images. d, Ex situ aberration-corrected TEM image showing the presence of amorphous oxides embedded into the npAu ligament. e, HAADF-STEM image showing areas of varying contrast on the npAu surface, corresponding to features seen by TEM in d. f, EELS analysis of various spots from e, showing that the darker areas are regions of high Ag and O concentration relative to the rest of the npAu surface.
Figure 35B:
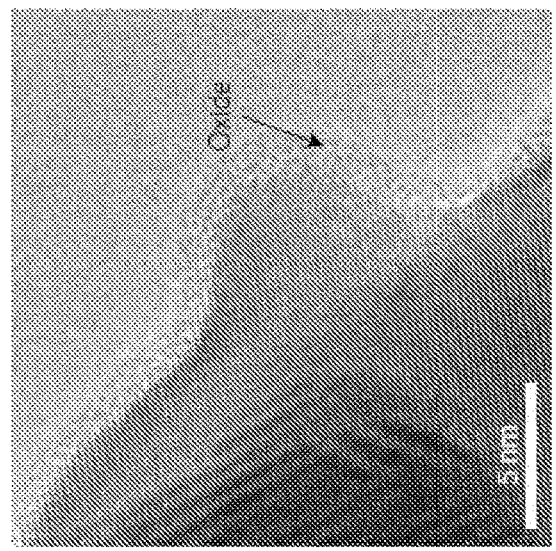
Figure 35A:
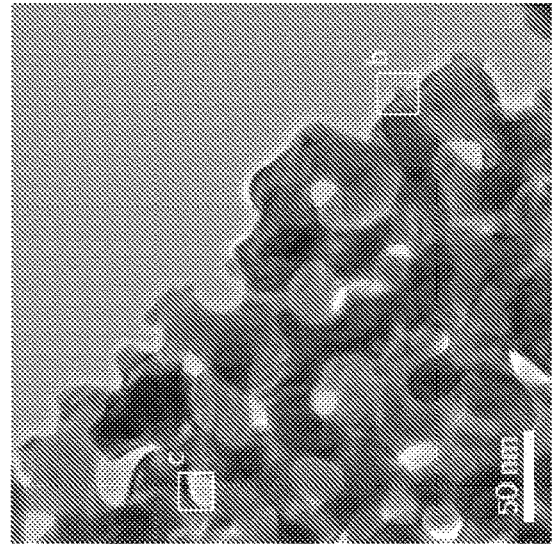
Figure 35F:
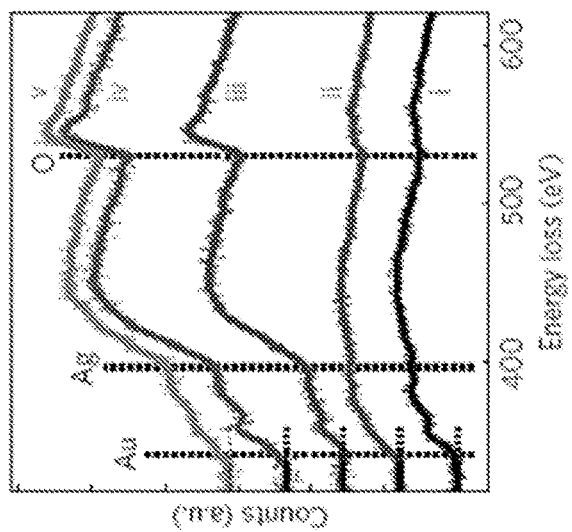
Figure 35E:
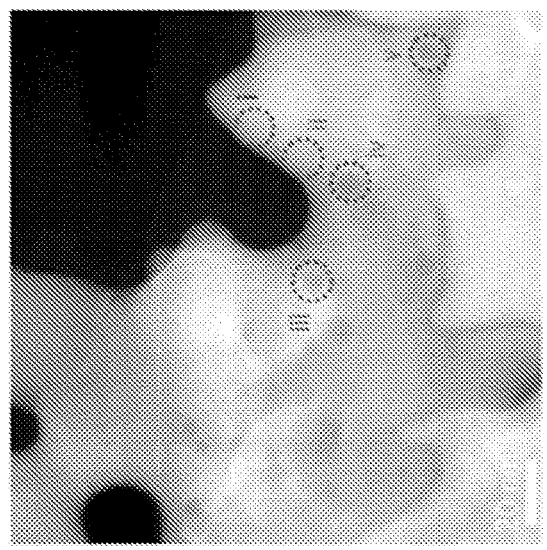
Figure 35D:
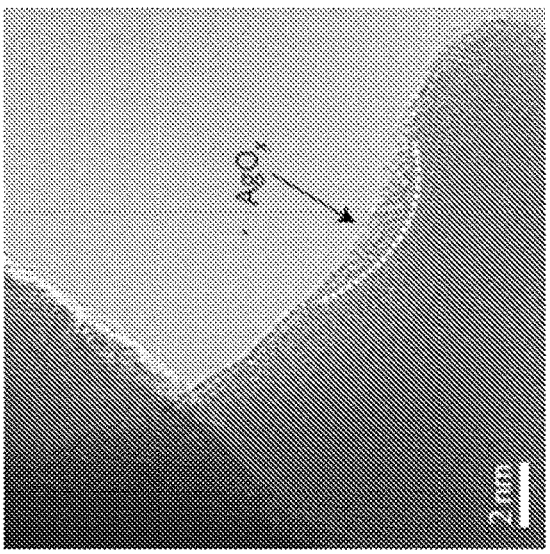

When the O$_3$-treated npAu catalyst is first exposed to pulses of a mixture of CO and CH$_3$OH simultaneously, both reactants are completely consumed and CO$_2$ is the only product observed (FIG. 34c, d). After most of the surface oxygen (95%) is reacted away through CO$_2$ production, the CO conversion rapidly drops to zero. Concomitantly, selective reaction of methanol to formaldehyde and methyl formate commences without CO$_2$ formation. The pattern of methanol reactivity is essentially the same whether it is pulsed alone or in the presence of CO (FIG. 34).

These results clearly demonstrate that there are two chemically distinct types of oxygen species formed during the O$_3$ treatment of the catalyst and that only the minority oxygen species, present on the surface at low concentrations, is responsible for the selective oxidation of methanol. Furthermore, the catalyst facilitates the dissociation of O$_2$ after complete reaction of the 'selective' oxygen via reaction with methanol. Exposure of this material to dioxygen produces adsorbed O, but only from reaction with the minority sites (Wang, L.-C. et al. J. Catal. 2016, 334, 778); this adsorbed oxygen is unreactive with CO but reacts readily with methanol to give selective oxidation products. This is in agreement with previous studies of ozone-activated npAu (Personick, M. L. et al. ACS Catal. 2015, 5, 4237).

The primary morphological change observed by in situ aberration-corrected transmission electron microscopy (TEM) after ozone treatment is the formation of an amorphous thin film oxide on the surface of the npAu (FIG. 35). The oxide covers >80% of the npAu surface (FIG. 35b, c) with a thickness of 1.1±0.1 nm. This oxide is not present in as-prepared npAu (that is, not treated with ozone). Additionally, islands (FIG. 35c) and embedded oxides (FIG. 35d) are observed on and within the npAu ligaments, respectively. The islands are two atomic layers in height and 2-6 nm in diameter. The observable inter-planar spacing within these structures is ~0.31 nm (compared with 0.24 nm for the (111) spacing of metallic Au and Ag), which suggests formation of metal oxides (Non-tetrahedrally Bonded Elements and Binary Compounds I; ed. Madelung, O. et al., 1998; Vol. 41C; Jones, P. G. et al. Acta Crystallogr. B. 1979, 35, 1435). These findings are in line with previous studies of textured Au(111) surfaces that indicate that treatment with ozone results in the formation of chemisorbed oxygen species and three-dimensional gold oxides of ~1.5 nm in thickness (Krozer, A. et al. *J. Vac. Sci. Technol. A.* 1997, 15, 1704). The disordered, embedded oxides also observed by TEM (FIG. 35d) are ~1-2 nm deep and ~6-8 nm in diameter.

In addition to these structural changes, high-angle annular dark-field scanning transmission electron microscopy/electron energy-loss spectroscopy (HAADF-STEM/EELS) analysis clearly shows that the ozone treatment causes the aggregation of Ag oxides at the npAu surface. This is seen in the HAADF-STEM image (FIG. 35d) as regions of lower density (that is, lower Z contrast). Further analysis by EELS (FIG. 35e) shows that these regions are high in Ag and O concentration. By contrast, little to no Ag is detected in the npAu away from these regions.

Figure 36A:
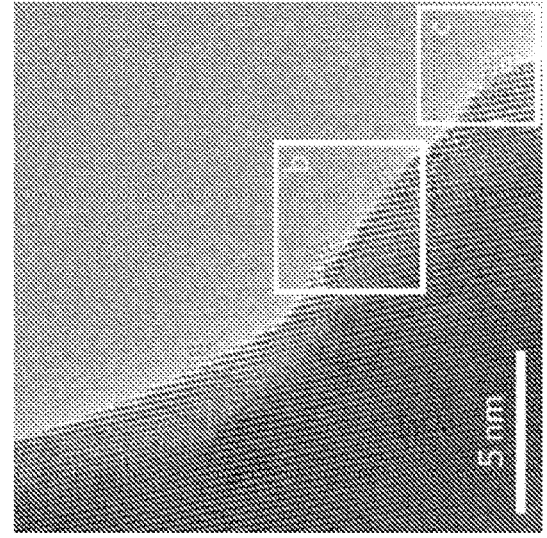
FIGS. 36a-36j shows the E-TEM analysis of npAu during CO and $CH_3OH$ exposure. In situ removal of the oxide layer and formation of nanoparticles due to reduction of ozone-treated npAu by CO and $CH_3OH$ is observed in aberration-corrected E-TEM images. a-c, Exposure of $O_3$-treated npAu to 0.1 torr CO at 150° C. for 30 min leads to removal of the oxide film and precipitation of defective nanoparticles (1-1.6 nm in diameter) with an expanded lattice. d, Masked fast Fourier transform of the region marked in b, showing the two types of lattice spacing observed. e, Inverse fast Fourier transform of d, showing the oxidic 0.32 nm spacing corresponding to the particle in b. f-h, Highly crystalline metallic nanoparticles form following further reduction by 0.1 torr $CH_3OH$ at 150° C. for 30 min. i, Masked fast Fourier transform of the region marked in h. j, Inverse fast Fourier transform of i, showing a typical Au(111)-type arrangement. All images were obtained at 25° C. and under vacuum conditions after reduction treatments; no beam effects were observed during imaging. Note: the observed particle density and shape on the npAu surface accounts for ~11% of the npAu surface area after CO reduction and ~27% after $CH_3OH$ reduction.
Figure 36B:
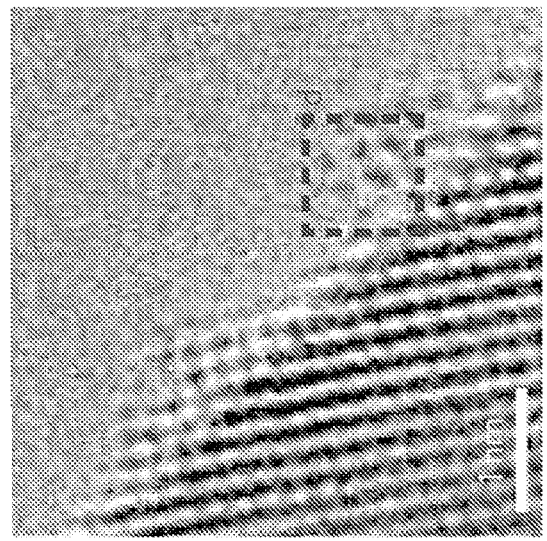
Figure 36C:

All of the amorphous oxide layer is removed by in situ reduction of the $O_3$-treated npAu with CO (0.1 torr CO at 150° C. for 30 min) in the environmental TEM (E-TEM FIG. 36a-c). Since catalytic CO oxidation is not sustained, we infer that the oxide is not reformed under operating catalytic conditions. The removal of the oxide layer is accompanied by formation of small, irregular nanoparticles on highly stepped regions of npAu (FIG. 36b, c). The newly formed particles are irregularly shaped with large variations in the atomic spacing (FIG. 36b). The larger lattice spacing (~0.32 nm), determined by Fourier transform analysis, corresponds to that of gold and silver oxides.

Figure 36D:
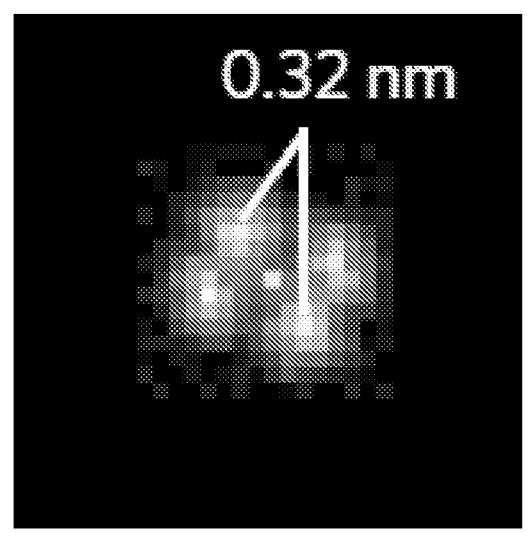
Figure 36E:
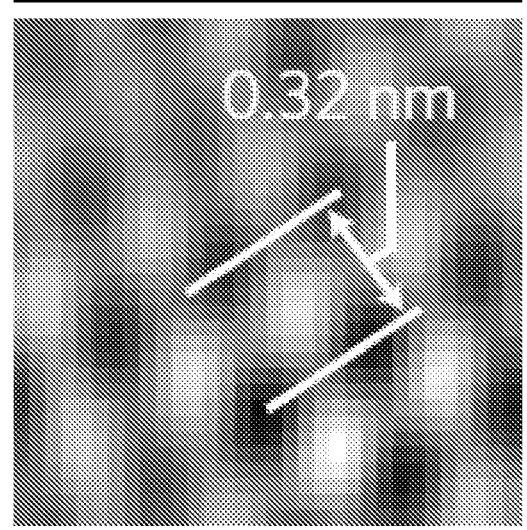
Figure 36F:
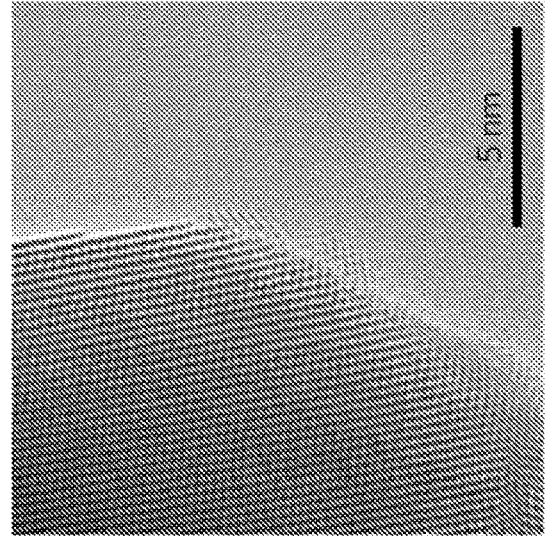
Figure 36G:
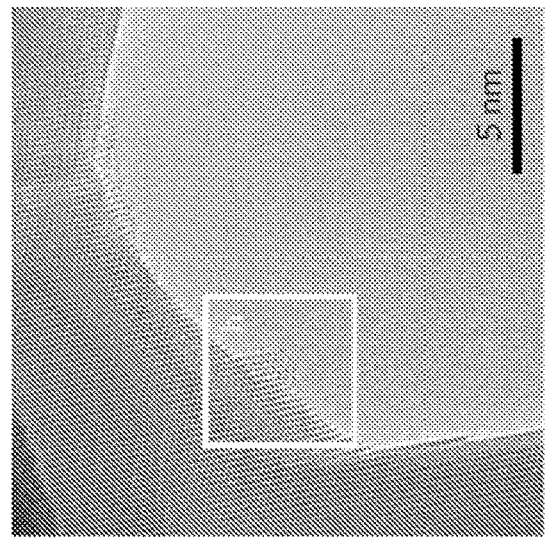
Figure 36H:
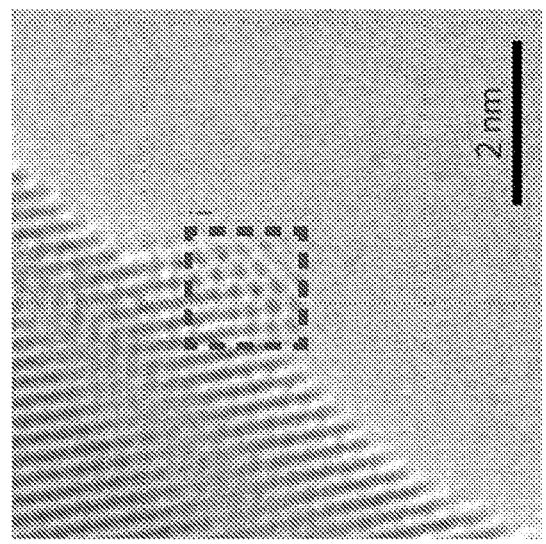
Figure 36I:
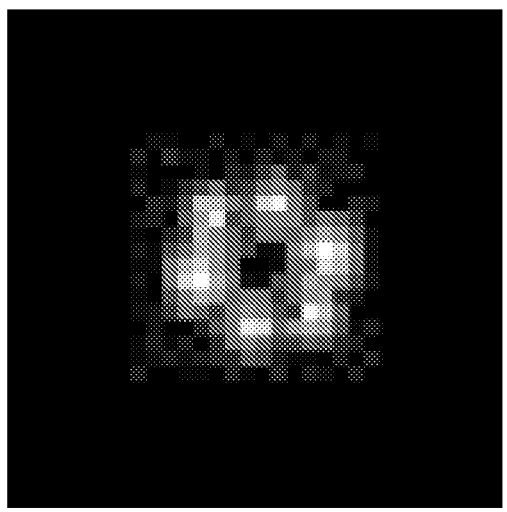
Figure 36J:
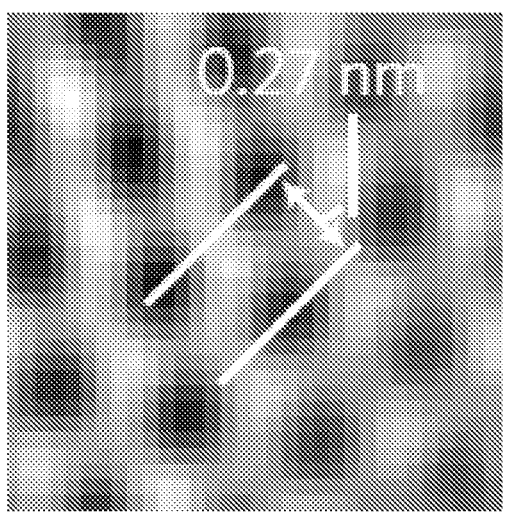

Further reduction of the npAu surface by methanol results in the growth of crystalline nanoparticles at the surface to 2-2.5 nm in diameter (FIG. 36d-f). In addition to the increase in diameter, these structures appear more ordered and show more distinct facets, as shown in FIG. 36f. The particle aspect ratio (height to width ratio at the base of the particle) also changes from 0.7 after CO treatment to 0.3 after $CH_3OH$ exposure. These changes may indicate a higher propensity for the particles to realloy into the bulk at low oxygen concentrations at the surface. Furthermore, there is a clear alignment of the crystal planes in the particle and ligament, suggesting that the particles are more metallic in nature.

Figures 37A, 37B, 37C:
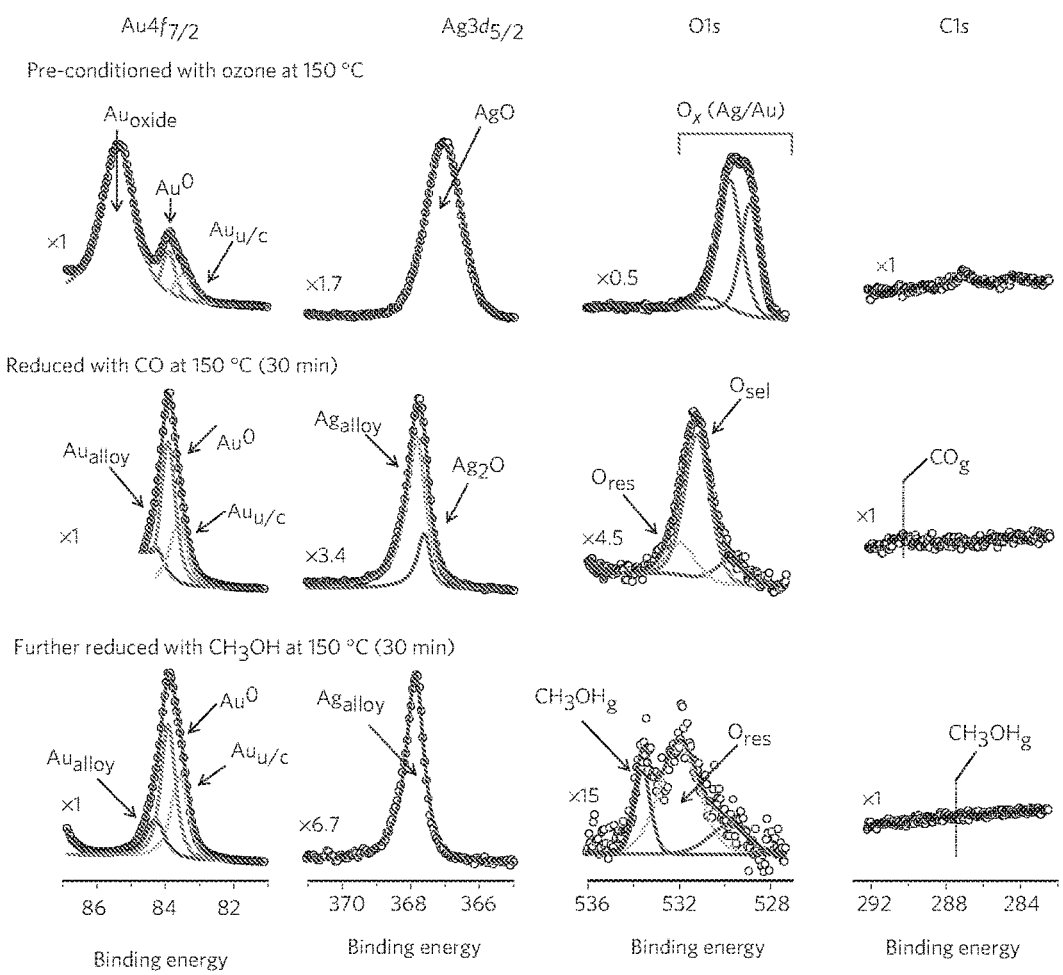
FIGS. 37a-37c shows the AP-XPS analysis of npAu. AP-XPS data demonstrate that two distinct O species are present on $O_3$-treated npAu and that the surface Ag concentration decreases as a result of reduction by CO and $CH_3OH$. a, After the ozone treatment in 0.3 torr 2% $O_3/O_2$ at 150° C. for 30 min, both Au and Ag are oxidized (labelled Auoxide and AgO) and the O1s contributions are typical of bulk Au and Ag oxides (labelled $O_x$). b, After reduction by 0.1 torr CO at 150° C. for 30 min, Au is completely reduced to $Au^0$ and there is an increase in undercoordinated Au sites ($Au_{u/c}$); some AgO is reduced to AgO while the majority is realloyed with Au (Agalloy); a new $O_1s$ contribution is observed, thought to be responsible for selective $CH_3OH$ oxidation ($O_{sel}$). c, Further reduction by 0.1 torr $CH_3OH$ at 150° C. for 30 min shows that the remaining $Ag_2O$ is reduced, there is a further increase in undercoordinated Au sites ($Au_{u/c}$), and only a small amount of residual, subsurface oxygen remains ($O_{res}$). The kinetic energy for all spectra was kept at 200 eV, corresponding to an inelastic mean free path of 0.5 nm in Au.

The oxidation and enrichment of Ag at the npAu surface after ozone treatment is demonstrated using ambient-pressure X-ray photoelectron spectroscopy (AP-XPS; FIG. 37). Essentially all Ag and 80% of Au within the 0.5 nm sampling depth (that is, inelastic mean free path through Au) (Tanuma, S. et al. *Surf. Interface Anal.* 1994, 21, 165) are initially oxidized by ozone at 150° C. (FIG. 37a). Immediately following the ozone treatment, the Ag/Au atomic ratio is 0.46 (a 30% increase relative to fresh npAu), even though the bulk npAu Ag concentration is only ~3 at % based on energy dispersive X-ray spectroscopy (Personick, M. L. et al. *ACS Catal.* 2015, 5, 4237). Furthermore, all of the detectable silver on the surface is fully oxidized to AgO.

The presence of chemically distinct oxygen species after ozone treatment is also detected using the AP-XPS. The O1s binding energy is in agreement with previously reported oxygen states for bulk Au and Ag oxides (FIG. 37a) (Krozer, A. et al. *J. Vac. Sci. Technol. A.* 1997, 15, 1704; Hammond, J. S. et al. *Anal. Chem.* 1975, 47, 2193; Hoflund, G. B. et al. *Phys. Rev. B.* 2000, 62, 11126; Xu, B. et al. *Chem. Eur. J.* 2014, 20, 4646). Following reduction by CO (0.1 torr, 150° C.), ~90% of this oxidic oxygen is removed (FIG. 37b), which correlates with the CO pulse titration results described above and with the restructuring of the materials in E-TEM. These results further confirm that CO readily reacts with the oxidic oxygen. A new oxygen species ($O_{sel}$) with a binding energy of 531.5 eV appears in conjunction with the reduction (FIG. 37b). This oxygen species persists until exposure to $CH_3OH$ (FIG. 37c) and it is attributed to the second state of O that leads to selective oxidation of methanol. There is also a residual state of oxygen ($O_{res}$) with a binding energy of 532 eV that remains in the surface region even after the 30 min exposure to methanol at 150° C.; this species is attributed to oxygen in the subsurface (Boronin, A. I. et al. *J. Electron Spectrosc. Relat. Phenom.* 1998, 96, 43). Depth profiling of the npAu over the course of these experiments indicates that the oxidized Ag and Au species are present only at the outer surface region and that realloying of Ag into the bulk takes place during the sequential reduction by CO and $CH_3OH$.

Figure 38:
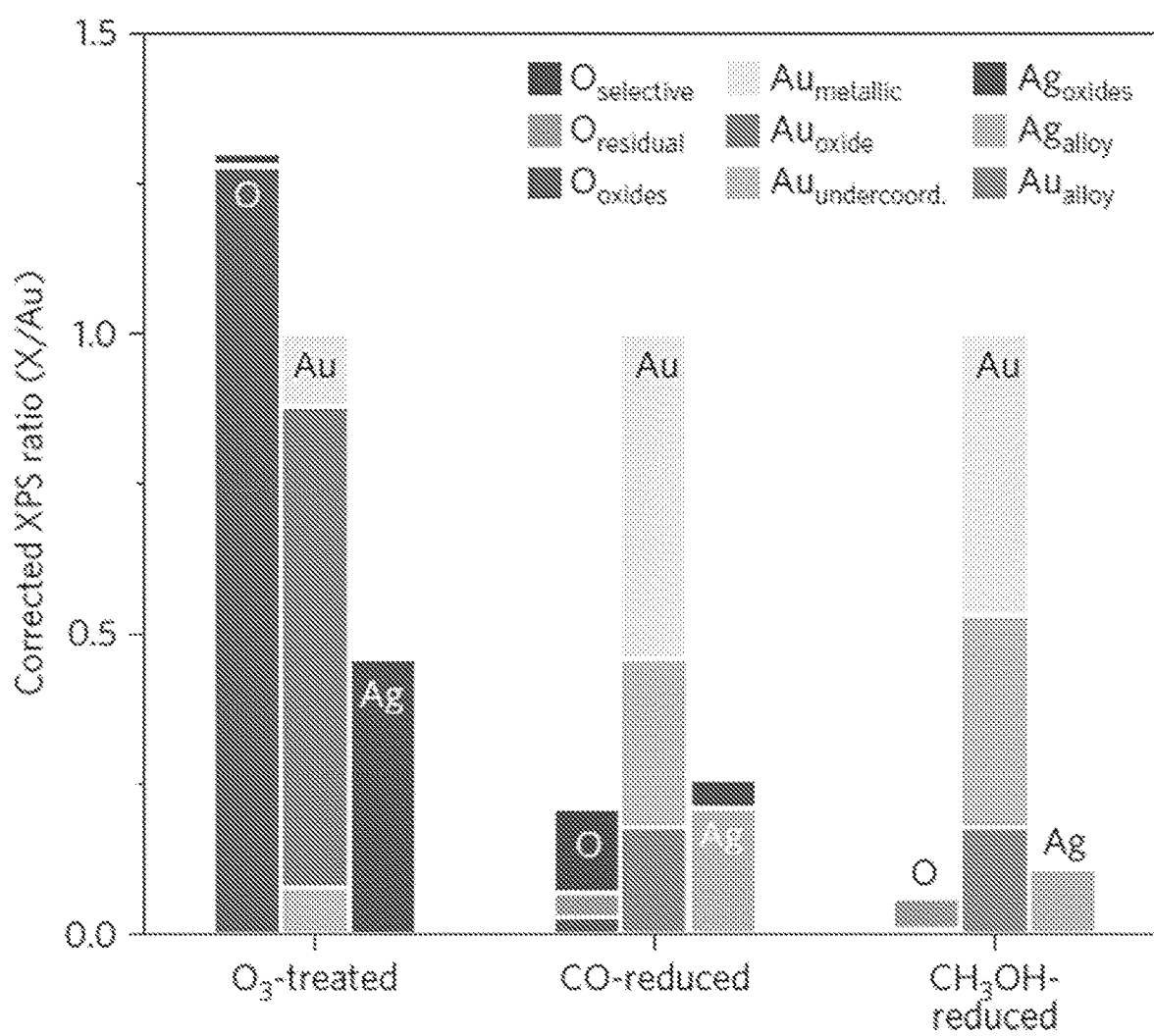
FIG. 38 shows the changes in the relative surface concentrations of Ag, O and Au. Quantification of Au, Ag and O contributions from FIG. 37 expressed as a ratio relative to the total Au XPS signal intensity ($I_x/I_{Au}$). After the $O_3$ treatment, Ag and Au are heavily oxidized. After reduction by CO, the contributions to the AgAu alloy ($Ag_{alloy}$), undercoordinated Au, and selective oxygen ($O_{sel}$) increase. Further reduction by $CH_3OH$ reduces the remaining silver oxides, maintains the $Ag_{alloy}$ character of Ag and further increases the contribution to undercoordinated Au. Only residual oxygen ($O_{res}$) remains after $CH_3OH$ reduction.

Reduction of the $O_3$-treated npAu also leads to a significant rearrangement of gold and silver within the surface region such that the Ag/Au ratio decreases significantly from 0.46 to 0.26 after reduction of the material by CO (FIGS. 37b and 38). A corresponding increase in the abundance of undercoordinated Au ($Au_{u/c}$), metallic Au ($Au^0$), and Ag-alloyed Au ($Au_{alloy}$) is also observed (FIG. 38) (Tyson, C. C. et al. *Phys. Rev. B.* 1992, 45, 8924). Nevertheless, some $Ag_2O$ remains and the ratio of the $Au_{alloy}$ to $Ag_{alloy}$ is found to be ~1. Subsequent reduction by $CH_3OH$ (FIG. 37c) results in a further reduction of silver content in the surface (to an Ag/Au ratio of 0.11), a further increase in the undercoordinated gold sites, and the complete removal of the $Ag_2O$ phase (FIG. 38). In light of the E-TEM results, we attribute the increase in undercoordinated Au sites to the formation and growth of small crystalline particles on the npAu surface (FIG. 36).

This comprehensive investigation of the activation of npAu using ozone treatment followed by exposure to reductants elucidates the key role that catalyst preparation and pretreatment has on the resulting activity. The initial treatment with ozone substantially enriches the surface in Ag by more than a factor of 10 compared with the bulk average and it removes adventitious carbon from the npAu, as demonstrated previously (Stowers, K. J. et al. *J. Catal.* 2013, 308, 131). The treatment with ozone also leads to an excess of oxygen at the surface: this yields an oxidic material that promotes combustion of methanol and other alcohols (Wang, L.-C. et al. *J. Catal.* 2015, 329, 78; Personick, M. L. et al. *ACS Catal.* 2015, 5, 4237). This oxidic state can also be reduced by reaction with CO.

The first state of reduction by CO leads to removal of the oxidic oxygen and redistribution of both Ag and Au. The surface remains enriched in Ag with disordered particles that are on the order of a few nanometres in diameter. The second state of oxygen that persists does not react with CO; rather, it induces selective oxidation of methanol and most likely other alcohols. The reason that this oxygen does not react with CO, but does react with methanol is not known and is a topic for further study. A possible explanation is that the disordered nature of the Ag-containing nanoparticles (FIG. 36a-e) results in strong electron depletion at the surface, leading to the formation of associative oxygen species (supported by the high AP-XPS binding energies) (Kibis, L. S. et al. *Appl. Surf. Sci.* 2010, 257, 404). Further reduction of the second state of oxygen by methanol leads to additional rearrangement of the surface so that metallic nanoparticles are formed and the Ag/Au ratio is lowered. The pattern of compositional changes indicates that Ag segregation is favoured under highly oxidizing conditions but that it recedes from the surface under reducing conditions. Importantly, the Ag distribution does not revert to the bulk distribution of the as-prepared material. The near-surface region of the active material is still enriched in Ag but not to an extent that oxides form that would lead to over-oxidation (that is, combustion) of the methanol.

These results provide insight into how ozone pretreatment leads to the catalytic function of the activated npAu material under steady-state conditions, when both $O_2$ and methanol are present. Highly selective formation of methyl formate from methanol occurs under steady-state flow conditions that do not lead to the accumulation of excess oxygen. The surface is enriched in Ag even after reduction with CO, which leaves oxygen that selectively reacts with methanol, suggesting that under steady-state conditions a Ag—Au alloy is present. Indeed, additional AP-XPS data confirm that the selective oxygen species ($O_{sel}$), which is the active species for methanol activation, is also present on the sample surface after prolonged exposure to steady-state reaction conditions.

Nanoporous gold (npAu) ingots were prepared by free corrosion of $Ag_{70}Au_{30}$ gold ingots in 70% nitric acid (Sigma Aldrich) for 48 h. The initially prepared Ag—Au ingots were homogenized by annealing in argon for 140 h at 875° C. After cutting, rolling and stamping, the samples were annealed for a second time of 4 h at 800° C. After dealloying, the samples were washed thoroughly with deionized water, and dried in air. Nanoporous gold hollow microspheres were prepared by a polystyrene sphere templating method previously reported by our group. Nanoporous gold foils for TEM analysis were prepared by dealloying $Ag_{85}Au_{15}$ leaves in nitric acid. All samples had a residual Ag concentration of ~3 at % after nitric acid leaching, as determined by energy-dispersive spectroscopy analysis.

All npAu catalysts were activated and tested in a quartz tube reactor housed within a temperature-controlled tubular furnace operated at atmospheric pressure. Ultrahigh-purity gases (He, $O_2$) were supplied to the reactor by mass flow controllers (MKS). Ozone treatment was performed by flowing ozone (2-3%) in an $O_2$ gas at 70 ml $min^{-1}$ over the catalyst at room temperature for ~30 min, followed by ramping the temperature to 150° C. at 10° C. $min^{-1}$ and holding for 1 h. The sample was cooled in the ozone mixture and purged with He at room temperature for at least 1 h. Activation and testing of the sample in reaction gas was then immediately performed in 6.5% $CH_3OH$-20% $O_2$ (balance He) at 50 ml $min^{-1}$ using a temperature ramp from 298 K (25° C.) to 425 K (150° C.) at 10° C. $min^{-1}$. Methanol was supplied by a saturated He stream directed through a bubbler, followed by a temperature-controlled condenser. The effluent gas was continuously monitored by an online GC-MS (Agilent 5975C and Agilent 7890A) equipped with HP-PLOT Q and CARBONPLOT columns.

The pulse experiments were carried out in a commercial temporal analysis of products (TAP)-2 reactor. In a typical pulse response experiment a narrow pulse of reactant gas (about $10^{-8}$ mol per pulse, pulse width 0.135 ms) was injected into a packed-bed microreactor using a high-speed, magnetically controlled pulse valve. The microreactor was a quartz tubular reactor with a length of 38 mm and a diameter of 6.35 mm, housing an internal thermocouple. The microreactor sat on top of a high-throughput vacuum chamber ($10^{-8}$-$10^{-9}$ torr) containing a RGA200 mass spectrometer, which was used to detect the effluent from the reactor. The npAu catalyst was sandwiched in a thin-zone configuration in the middle of the microreactor packed among inert quartz particles with diameters between 250 and 300 µm. Pulse sizes were chosen to ensure Knudsen flow throughout the reactor.

Ambient-pressure X-ray photoelectron spectroscopy (AP-XPS) experiments were conducted at Beamline 11.0.2 at the Advanced Light Source at Lawrence Berkeley National Laboratory. A nanoporous gold ingot was previously treated in a flow reactor in 2% $O_3$ (in $O_2$) at 150° C. for 1 h. The treated ingot was loaded onto a ceramic button heater, mounted within the AP-XPS chamber at Beamline 11.0.2.

Environmental-TEM (E-TEM) studies were performed at the Center for Functional Nanomaterials at Brookhaven National Laboratory using an FEI Titan aberration-corrected TEM operating at 300 kV. The instrument has a base pressure of 3-4×$10^{-7}$ torr. The spatial resolution is <180 pm under E-TEM conditions. Ozone-treated npAu foils were placed on a DENS Solutions heated sample holder by dispersion in deionized water. After drying overnight at room temperature, the holder was inserted into the microscope. Gases and vapours were introduced into the microscope using a gas-handling manifold equipped with dosing valves.

OTHER EMBODIMENTS

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the invention that come within known or customary practice within the art to which the invention pertains and may be applied to the essential features hereinbefore set forth, and follows in the scope of the claims.

Other embodiments are within the claims.

What is claimed is:

1. A nanoporous gold catalyst produced by a method comprising the steps of:
   providing nanoporous gold comprising 0.1 to 10% silver by atom; and
   contacting the nanoporous gold with ozone at a temperature of 100° C. or greater for a time sufficient to form the activated nanoporous gold catalyst.

2. A nanoporous gold catalyst comprising from 0.1 to 10% silver by atom, wherein the catalyst is treated with ozone at a temperature of 100° C.-185° C., or wherein the catalyst is active for selective oxidation of alcohols and inactive for oxidation of CO, or wherein at least 80% of the surface silver is oxidized and at least 60% of the surface gold is oxidized.

3. The nanoporous gold catalyst of claim 2, further treated with a mixture of dioxygen and a primary alcohol, or having a ligament width of 10-500 nm.

4. The catalyst of claim 2, wherein the surface layer of the catalyst has a higher Ag/Au atomic ratio relative to the bulk material of the catalyst.

5. The nanoporous gold catalyst of claim 2, wherein the catalyst comprises an oxygen species with a binding energy of 531.5 eV.

6. The nanoporous gold catalyst of claim 2, wherein the catalyst is active for selective oxidation of alcohols and inactive for oxidation of CO.

7. The nanoporous gold catalyst of claim 2, wherein the catalyst is treated with ozone at a temperature of 100°

C.-185° C., and the ozone is present within a mixture comprising one or more gases at a concentration of from 10 to 50 g/Nm$^3$.

8. The nanoporous gold catalyst of claim 2, wherein at least 80% of the surface silver is oxidized and at least 60% of the surface gold is oxidized.

* * * * *